United States Patent
E et al.

(10) Patent No.: US 11,592,449 B2
(45) Date of Patent: Feb. 28, 2023

(54) USE OF LC-MS/MS TO QUANTITATE PROTEIN BIOMARKERS

(71) Applicant: Regeneron Pharmaceuticals, Inc., Tarrytown, NY (US)

(72) Inventors: Sook Yen E, Croton-on-Hudson, NY (US); Haibo Qiu, Hartsdale, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 547 days.

(21) Appl. No.: 16/534,095

(22) Filed: Aug. 7, 2019

(65) Prior Publication Data

US 2020/0064355 A1 Feb. 27, 2020

Related U.S. Application Data

(60) Provisional application No. 62/715,973, filed on Aug. 8, 2018.

(51) Int. Cl.
| | | |
|---|---|---|
| *G01N 33/68* | (2006.01) | |
| *G16H 50/30* | (2018.01) | |
| *G16B 40/10* | (2019.01) | |

(52) U.S. Cl.
CPC ......... *G01N 33/6851* (2013.01); *G16B 40/10* (2019.02); *G16H 50/30* (2018.01)

(58) Field of Classification Search
None
See application file for complete search history.

(56) References Cited

U.S. PATENT DOCUMENTS

2015/0111220 A1    4/2015   Blume et al.

FOREIGN PATENT DOCUMENTS

| EP | 2821076 A1 | 1/2015 |
| WO | WO 2012/037603 A1 | 3/2012 |
| WO | WO 2013/151726 A1 | 10/2013 |
| WO | WO 2015/103645 A2 | 7/2015 |

OTHER PUBLICATIONS

Biognosys AG, "PlasmaDive™ Reference Peptides Kit for Human Plasma," First Edition, Version 1.00, Apr. 2017, 11 pages, Retrieved from https://www.biognosys.com/media.ashx/plasmadiverefpep-manual.pdf.

Cambridge Isotope Laboratories, Inc. and MRM Proteomics, "PeptiQuant™ Biomarker Assessment Kit (BAK-76)," Apr. 23, 2015, 3 pages, retrieved from from https://www.si-science.co.jp/product/data/2015product-2.pdf.

Gallien et al., "Selected reaction monitoring applied to proteomics," J. Mass. Spectrom., 2011., 46, 298-312.

GenBank Accession No. ACN62221.1, complement C1q subcomponent subunit A [Danio rerio], Sep. 3, 2010, 2 pages.

GenBank Accession No. ACN62222.1, complement C1q subcomponent subunit B [Danio rerio], Sep. 3, 2010, 2 pages.

GenBank Accession No. ACN62223.1, complement C1q subcomponent subunit C [Danio rerio], Sep. 3, 2010, 2 pages.

(Continued)

*Primary Examiner* — Xiaoyun R Xu
(74) *Attorney, Agent, or Firm* — Cooley LLP; Matthew Pavao; Robert E. Powers

(57) ABSTRACT

The present disclosure provides methods and compositions for the determining the abundance and/or concentration of protein biomarkers in a biological sample.

18 Claims, 33 Drawing Sheets

Specification includes a Sequence Listing.

(56) References Cited

OTHER PUBLICATIONS

Mayr et al., "Proteomics, Metabolomics, and Immunomics on Microparticles Derived From Human Atherosclerotic Plaques," Circ Cardiovasc Genet., 2009, 2:379-388, and Supplemental Material, 55 pages.

Melis et al., "Complement in therapy and disease Regulating the complement system with antibody-based therapeutics," Molecular Immunology (2015) 67:117-130.

Molloy, "A Semi Quantitative Method for the Analysis of Tryptic Peptides in Human Serum: A Rapid, Targeted UPLC-MS/MS Approach Using Biognosys Plasma Dive Kit," Waters Corporation, Aug. 2018, Retrieved from https://www.waters.com/webassets/cros/library/docs/720006323en.pdf.

Molloy, "Single High-Throughput UPLC-MS-MS Platform for Targeted Metabolomic, Lipidomic and Proteomic Studies (Targeted Multi-Omics)," Water Corporation, 2018, Poster, Retrieved from https://www.waters.com/webassets/cms/library/dots/2018msacl_molloy_multi-omics.pdf.

NCBI Reference Sequence: NP_000482.3, complement C1q subcomponent subunit B precursor [*Homo sapiens*], Jan. 2, 2020, 5 pages.

NCBI Reference Sequence: NP_031598.2, complement C1q subcomponent subunit A precursor [Mus musculus], Jan. 21, 2020, 4 pages.

NCBI Reference Sequence: NP_031600.2, complement C1q subcomponent subunit C precursor [Mus musculus], Dec. 26, 2019, 4 pages.

NCBI Reference Sequence: NP_033907.1, complement C1q subcomponent subunit B precursor [Mus musculus], Dec. 30, 2019, 4 pages.

NCBI Reference Sequence: NP_057075.1, complement C1q subcomponent subunit A precursor [*Homo sapiens*], Nov. 26, 2019, 5 pages.

NCBI Reference Sequence: NP_062135.1, complement C1q subcomponent subunit B precursor [Rattus norvegicus], Dec. 25, 2019, 4 pages.

NCBI Reference Sequence: NP_758957.2, complement C1q subcomponent subunit C isoform 1 precursor [*Homo sapiens*], Dec. 31, 2019, 4 pages.

NCBI Reference Sequence: NP_001008515.1, complement C1q subcomponent subunit A precursor [Rattus norvegicus], Dec. 27, 2019, 4 pages.

NCBI Reference Sequence: NP_001008524.1, complement C1q subcomponent subunit C precursor [Rattus norvegicus], Dec. 24, 2019, 3 pages.

NCBI Reference Sequence: NP_001253737.1, complement C1q subcomponent subunit C precursor [Macaca mulatta], Apr. 29, 2019, 2 pages.

NCBI Reference Sequence: XP_535367.1, complement C1q subcomponent subunit A [Canis lupus familiaris], Sep. 5, 2017, 2 pages.

NCBI Reference Sequence: XP_544507.2, complement C1q subcomponent subunit B [Canis lupus familiaris], Sep. 5, 2017, 2 pages.

NCBI Reference Sequence: XP_003433793.1, complement C1q subcomponent subunit C [Canis lupus familiaris], Sep. 5, 2017, 2 pages.

NCBI Reference Sequence: XP_005544557.1, Predicted: complement C1q subcomponent subunit B [Macaca fascicularis], Jan. 25, 2016, 2 pages.

NCBI Reference Sequence: XP_014985904.1, complement C1q subcomponent subunit A [Macaca mulatta], Apr. 26, 2019, 2 pages.

NCBI Reference Sequence: XP_014985910.1, complement C1q subcomponent subunit B [Macaca mulatta], Apr. 26, 2019, 2 pages.

NCBI Reference Sequence: XP_015296579.1, Predicted: complement C1q subcomponent subunit C [Macaca fascicularis], Jan. 25, 2016, 2 pages.

NCBI Reference Sequence: XP_015296582.1, Predicted: complement C1q subcomponent subunit A [Macaca fascicularis], Jan. 25, 2016, 2 pages.

SEQUENCE LISTING

<160> NUMBER OF SEQ ID NOS: 41

<210> SEQ ID NO 1
<211> LENGTH: 245
<212> TYPE: PRT
<213> ORGANISM: Homo sapiens

<400> SEQUENCE: 1

```
Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240
```

```
Ile Phe Pro Ser Ala
            245

<210> SEQ ID NO 2
<211> LENGTH: 253
<212> TYPE: PRT
<213> ORGANISM: Homo sapiens

<400> SEQUENCE: 2

Met Met Met Lys Ile Pro Trp Gly Ser Ile Pro Val Leu Met Leu Leu
1               5                   10                  15

Leu Leu Leu Gly Leu Ile Asp Ile Ser Gln Ala Gln Leu Ser Cys Thr
            20                  25                  30

Gly Pro Pro Ala Ile Pro Gly Ile Pro Gly Ile Pro Gly Thr Pro Gly
        35                  40                  45

Pro Asp Gly Gln Pro Gly Thr Pro Gly Ile Lys Gly Glu Lys Gly Leu
    50                  55                  60

Pro Gly Leu Ala Gly Asp His Gly Glu Phe Gly Glu Lys Gly Asp Pro
65                  70                  75                  80

Gly Ile Pro Gly Asn Pro Gly Lys Val Gly Pro Lys Gly Pro Met Gly
                85                  90                  95

Pro Lys Gly Gly Pro Gly Ala Pro Gly Ala Pro Gly Pro Lys Gly Glu
            100                 105                 110

Ser Gly Asp Tyr Lys Ala Thr Gln Lys Ile Ala Phe Ser Ala Thr Arg
        115                 120                 125

Thr Ile Asn Val Pro Leu Arg Arg Asp Gln Thr Ile Arg Phe Asp His
    130                 135                 140

Val Ile Thr Asn Met Asn Asn Asn Tyr Glu Pro Arg Ser Gly Lys Phe
145                 150                 155                 160

Thr Cys Lys Val Pro Gly Leu Tyr Tyr Phe Thr Tyr His Ala Ser Ser
                165                 170                 175

Arg Gly Asn Leu Cys Val Asn Leu Met Arg Gly Arg Glu Arg Ala Gln
            180                 185                 190

Lys Val Val Thr Phe Cys Asp Tyr Ala Tyr Asn Thr Phe Gln Val Thr
        195                 200                 205

Thr Gly Gly Met Val Leu Lys Leu Glu Gln Gly Glu Asn Val Phe Leu
    210                 215                 220

Gln Ala Thr Asp Lys Asn Ser Leu Leu Gly Met Glu Gly Ala Asn Ser
225                 230                 235                 240

Ile Phe Ser Gly Phe Leu Leu Phe Pro Asp Met Glu Ala
                245                 250

<210> SEQ ID NO 3
<211> LENGTH: 245
<212> TYPE: PRT
<213> ORGANISM: Homo sapiens

<400> SEQUENCE: 3

Met Asp Val Gly Pro Ser Ser Leu Pro His Leu Gly Leu Lys Leu Leu
1               5                   10                  15

Leu Leu Leu Leu Leu Leu Pro Leu Arg Gly Gln Ala Asn Thr Gly Cys
            20                  25                  30

Tyr Gly Ile Pro Gly Met Pro Gly Leu Pro Gly Ala Pro Gly Lys Asp
        35                  40                  45

Gly Tyr Asp Gly Leu Pro Gly Pro Lys Gly Glu Pro Gly Ile Pro Ala
    50                  55                  60
```

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
        115                 120                 125

His Gln Pro Pro Ala Pro Asn Ser Leu Ile Arg Phe Asn Ala Val Leu
130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
210                 215                 220

Tyr Asp Met Val Gly Ile Gln Gly Ser Asp Ser Val Phe Ser Gly Phe
225                 230                 235                 240

Leu Leu Phe Pro Asp
                245

<210> SEQ ID NO 4
<211> LENGTH: 245
<212> TYPE: PRT
<213> ORGANISM: Macaca fascicularis

<400> SEQUENCE: 4

Met Glu Gly Pro Gln Gly Trp Leu Val Val Cys Val Leu Ala Ile Ser
1               5                   10                  15

Leu Ala Ser Ile Val Thr Gln Asn Val Cys Arg Ala Pro Asp Gly Lys
                20                  25                  30

Asn Gly Val Ala Gly Arg Pro Gly Arg Pro Gly Arg Pro Gly Leu Lys
            35                  40                  45

Gly Glu Arg Gly Glu Pro Gly Ala Pro Gly Ile Arg Thr Gly Ile Gln
        50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Asp Arg Gly Ile
                85                  90                  95

Pro Gly Ile Lys Gly Ile Lys Gly Asn Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Met Val Ile Thr Asn Gln Glu Glu Pro Tyr
130                 135                 140

Gln Asn His Ser Gly Arg Phe Val Cys Thr Val Pro Gly Tyr Tyr Tyr
145                 150                 155                 160

Phe Thr Phe Gln Val Val Ser Glu Arg Glu Ile Cys Leu Ser Ile Val
                165                 170                 175

Ser Ser Ser Arg Gly Gln Val Arg Arg Ser Leu Gly Phe Cys Asp Thr

```
                180                 185                 190
Thr Asn Lys Gly Leu Phe Gln Val Val Ser Gly Gly Met Val Leu Gln
            195                 200                 205
Leu Gln Arg Gly Asp Gln Val Trp Val Glu Lys Asp Pro Arg Lys Gly
        210                 215                 220
Asn Ile Tyr Gln Gly Leu Glu Ala Asp Ser Val Phe Ser Gly Phe Leu
225                 230                 235                 240
Ile Phe Pro Ser Ser
                245

<210> SEQ ID NO 5
<211> LENGTH: 253
<212> TYPE: PRT
<213> ORGANISM: Macaca fascicularis

<400> SEQUENCE: 5

Met Met Met Lys Ile Leu Trp Gly Ser Ile Pro Val Leu Met Leu Leu
1               5                   10                  15
Leu Leu Leu Gly Leu Leu Asp Val Ser Trp Ala Gln Gly Ser Cys Thr
            20                  25                  30
Gly Pro Pro Ala Ile Pro Gly Thr Pro Gly Ile Pro Gly Thr Pro Gly
        35                  40                  45
Ser Asp Gly Gln Pro Gly Thr Pro Gly Ile Lys Gly Glu Lys Gly Leu
    50                  55                  60
Pro Gly Leu Ala Gly Asp His Gly Glu Phe Gly Glu Lys Gly Asp Pro
65                  70                  75                  80
Gly Ile Pro Gly Asn Pro Gly Lys Val Gly Pro Lys Gly Pro Met Gly
                85                  90                  95
Pro Lys Gly Gly Pro Gly Ala Pro Gly Ala Pro Gly Pro Lys Gly Glu
            100                 105                 110
Ser Gly Asp Tyr Lys Ala Thr Gln Lys Ile Ala Phe Ser Ala Thr Arg
        115                 120                 125
Thr Val Asn Thr Pro Leu Arg Arg Asp Gln Thr Ile Arg Phe Asp His
    130                 135                 140
Val Ile Thr Asn Met Asn Asn Asn Tyr Glu Pro Arg Ser Gly Lys Phe
145                 150                 155                 160
Thr Cys Arg Val Pro Gly Leu Tyr Tyr Phe Thr Tyr His Ala Ser Ser
                165                 170                 175
Arg Gly Asn Leu Cys Val Lys Leu Met Arg Gly Arg Glu Arg Pro Gln
            180                 185                 190
Lys Val Val Thr Phe Cys Asp Tyr Ala Tyr Asn Thr Phe Gln Val Thr
        195                 200                 205
Thr Gly Gly Met Val Leu Lys Leu Glu Gln Gly Glu Asn Val Phe Leu
    210                 215                 220
Gln Ala Thr Asp Lys Asn Ser Leu Leu Gly Met Glu Gly Ala Asn Ser
225                 230                 235                 240
Ile Phe Ser Gly Phe Leu Leu Phe Pro Asp Val Glu Ala
                245                 250

<210> SEQ ID NO 6
<211> LENGTH: 245
<212> TYPE: PRT
<213> ORGANISM: Macaca fascicularis

<400> SEQUENCE: 6

Met Asp Val Gly Pro Ser Ser Leu Pro His Leu Gly Leu Lys Leu Leu
```

```
  1               5                  10                 15
Leu Leu Leu Leu Leu Pro Leu Arg Gly Gln Ala Asn Thr Gly Cys
                20                 25                 30

Tyr Gly Ile Pro Gly Met Pro Gly Leu Pro Gly Ala Pro Gly Lys Asp
                35                 40                 45

Gly His Asp Gly Leu Pro Gly Pro Lys Gly Glu Pro Gly Ile Pro Ala
                50                 55                 60

Ile Pro Gly Thr Arg Gly Pro Lys Gly Gln Lys Gly Glu Pro Gly Thr
 65                 70                 75                 80

Pro Gly His Pro Gly Lys Asn Gly Pro Met Gly Pro Pro Gly Met Pro
                    85                 90                 95

Gly Val Pro Gly Pro Met Gly Ile Pro Gly Glu Pro Gly Glu Glu Gly
                   100                105                110

Arg Tyr Lys Gln Lys Tyr Gln Ser Val Phe Thr Val Ala Arg Gln Thr
                   115                120                125

His Gln Pro Pro Ala Pro Asn Ser Leu Ile Arg Phe Asn Ala Val Leu
                   130                135                140

Thr Asn Pro Gln Gly Asp Tyr Asp Thr Ser Thr Gly Lys Phe Thr Cys
145                150                155                160

Lys Val Pro Gly Leu Tyr Tyr Phe Val Tyr His Ala Ser His Thr Ala
                   165                170                175

Asn Leu Cys Val Leu Leu Tyr Arg Gly Gly Val Lys Val Val Thr Phe
                   180                185                190

Cys Gly His Thr Ser Gln Ala Asn Gln Val Asn Ser Gly Gly Val Leu
                   195                200                205

Leu Arg Leu Gln Val Gly Glu Glu Val Trp Leu Gly Val Asn Asp Tyr
                   210                215                220

Tyr Asp Met Val Gly Ile Gln Gly Ser Asp Ser Val Phe Ser Gly Phe
225                230                235                240

Leu Leu Phe Pro Asp
                245

<210> SEQ ID NO 7
<211> LENGTH: 245
<212> TYPE: PRT
<213> ORGANISM: Macaca mulatta

<400> SEQUENCE: 7

Met Glu Gly Pro Gln Gly Trp Leu Val Val Cys Val Leu Ala Ile Ser
  1               5                  10                 15

Leu Ala Ser Ile Val Thr Gln Asn Val Cys Arg Ala Pro Asp Gly Lys
                20                 25                 30

Asn Gly Val Ala Gly Arg Pro Gly Arg Pro Gly Arg Pro Gly Leu Lys
                35                 40                 45

Gly Glu Arg Gly Glu Pro Gly Ala Pro Gly Ile Arg Thr Gly Ile Gln
                50                 55                 60

Gly Leu Lys Gly Asp Gln Gly Glu Pro Gly Pro Ser Gly Asn Pro Gly
 65                 70                 75                 80

Lys Val Gly Tyr Pro Gly Pro Ser Gly Pro Leu Gly Asp Arg Gly Ile
                    85                 90                 95

Pro Gly Ile Lys Gly Ile Lys Gly Asn Pro Gly Asn Ile Lys Asp Gln
                   100                105                110

Pro Arg Pro Ala Phe Ser Ala Ile Arg Arg Asn Pro Pro Met Gly Gly
                   115                120                125
```

-continued

```
Asn Val Val Ile Phe Asp Met Val Ile Thr Asn Gln Glu Glu Pro Tyr
            130                 135                 140
Gln Asn His Ser Gly Arg Phe Val Cys Thr Val Pro Gly Tyr Tyr Tyr
145                 150                 155                 160
Phe Thr Phe Gln Val Val Ser Glu Arg Glu Ile Cys Leu Ser Ile Val
                165                 170                 175
Ser Ser Ser Arg Gly Gln Val Arg Arg Ser Leu Gly Phe Cys Asp Thr
            180                 185                 190
Thr Asn Lys Gly Leu Phe Gln Val Ser Gly Gly Met Val Leu Gln
            195                 200                 205
Leu Gln Arg Gly Asp Gln Val Trp Val Glu Lys Asp Pro Arg Lys Gly
210                 215                 220
Asn Ile Tyr Gln Gly Leu Glu Ala Asp Ser Val Phe Ser Gly Phe Leu
225                 230                 235                 240
Ile Phe Pro Ser Thr
            245

<210> SEQ ID NO 8
<211> LENGTH: 253
<212> TYPE: PRT
<213> ORGANISM: Macaca mulatta

<400> SEQUENCE: 8

Met Met Met Lys Ile Leu Trp Gly Ser Ile Pro Val Leu Met Leu Leu
1               5                   10                  15
Leu Leu Leu Gly Leu Leu Asp Val Ser Trp Ala Gln Gly Ser Cys Thr
            20                  25                  30
Gly Pro Pro Ala Ile Pro Gly Thr Pro Gly Ile Pro Gly Thr Pro Gly
            35                  40                  45
Ser Asp Gly Gln Pro Gly Thr Pro Gly Ile Lys Gly Glu Lys Gly Leu
    50                  55                  60
Pro Gly Leu Ala Gly Asp His Gly Glu Phe Gly Glu Lys Gly Asp Pro
65                  70                  75                  80
Gly Ile Pro Gly Asn Pro Gly Lys Val Gly Pro Lys Gly Pro Met Gly
                85                  90                  95
Pro Lys Gly Gly Pro Gly Ala Pro Gly Ala Pro Gly Pro Lys Gly Glu
            100                 105                 110
Ser Gly Asp Tyr Lys Ala Thr Gln Lys Ile Ala Phe Ser Ala Thr Arg
            115                 120                 125
Thr Ile Asn Thr Pro Leu Arg Arg Asp Gln Thr Ile Arg Phe Asp His
130                 135                 140
Val Ile Thr Asn Met Asn Asn Asn Tyr Glu Pro Arg Ser Gly Lys Phe
145                 150                 155                 160
Thr Cys Arg Val Pro Gly Leu Tyr Tyr Phe Thr Tyr His Ala Ser Ser
                165                 170                 175
Arg Gly Asn Leu Cys Val Lys Leu Met Arg Gly Arg Glu Arg Pro Gln
            180                 185                 190
Lys Val Val Thr Phe Cys Asp Tyr Ala Tyr Asn Thr Phe Gln Val Thr
            195                 200                 205
Thr Gly Gly Met Val Leu Lys Leu Glu Gln Gly Glu Asn Val Phe Leu
            210                 215                 220
Gln Ala Thr Asp Lys Asn Ser Leu Leu Gly Met Glu Gly Ala Asn Ser
225                 230                 235                 240
Ile Phe Ser Gly Phe Leu Leu Phe Pro Asp Val Glu Ala
                245                 250
```

<210> SEQ ID NO 9
<211> LENGTH: 245
<212> TYPE: PRT
<213> ORGANISM: Macaca mulatta

<400> SEQUENCE: 9

Met Asp Val Gly Pro Ser Ser Leu Pro His Leu Gly Leu Lys Leu Leu
1               5                   10                  15

Leu Leu Leu Leu Leu Pro Leu Arg Gly Gln Ala Asn Thr Gly Cys
            20                  25                  30

Tyr Gly Ile Pro Gly Met Pro Gly Leu Pro Gly Ala Pro Gly Lys Asp
        35                  40                  45

Gly His Asp Gly Leu Pro Gly Pro Lys Gly Glu Pro Gly Ile Pro Ala
    50                  55                  60

Ile Pro Gly Thr Arg Gly Pro Lys Gly Gln Lys Gly Glu Pro Gly Thr
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Tyr Gln Ser Val Phe Thr Val Ala Arg Gln Thr
        115                 120                 125

His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Gly Gly Val Lys Val Val Thr Phe
            180                 185                 190

Cys Gly His Thr Ser Gln Ala Asn Gln Val Asn Ser Gly Gly Val Leu
        195                 200                 205

Leu Arg Leu Gln Val Gly Glu Glu Val Trp Leu Gly Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp
            245

<210> SEQ ID NO 10
<211> LENGTH: 245
<212> TYPE: PRT
<213> ORGANISM: Mus musculus

<400> SEQUENCE: 10

Met Glu Thr Ser Gln Gly Trp Leu Val Ala Cys Val Leu Thr Met Thr
1               5                   10                  15

Leu Val Trp Thr Val Ala Glu Asp Val Cys Arg Ala Pro Asn Gly Lys
            20                  25                  30

Asp Gly Ala Pro Gly Asn Pro Gly Arg Pro Gly Arg Pro Gly Leu Lys
        35                  40                  45

Gly Glu Arg Gly Glu Pro Gly Ala Ala Gly Ile Arg Thr Gly Ile Arg
    50                  55                  60

Gly Phe Lys Gly Asp Pro Gly Glu Ser Gly Pro Pro Gly Lys Pro Gly
65                  70                  75                  80

-continued

```
Asn Val Gly Leu Pro Gly Pro Ser Gly Pro Leu Gly Asp Ser Gly Pro
             85                  90                  95

Gln Gly Leu Lys Gly Val Lys Gly Asn Pro Gly Asn Ile Arg Asp Gln
        100                 105                 110

Pro Arg Pro Ala Phe Ser Ala Ile Arg Gln Asn Pro Met Thr Leu Gly
    115                 120                 125

Asn Val Val Ile Phe Asp Lys Val Leu Thr Asn Gln Glu Ser Pro Tyr
130                 135                 140

Gln Asn His Thr Gly Arg Phe Ile Cys Ala Val Pro Gly Phe Tyr Tyr
145                 150                 155                 160

Phe Asn Phe Gln Val Ile Ser Lys Trp Asp Leu Cys Leu Phe Ile Lys
                165                 170                 175

Ser Ser Ser Gly Gly Gln Pro Arg Asp Ser Leu Ser Phe Ser Asn Thr
            180                 185                 190

Asn Asn Lys Gly Leu Phe Gln Val Leu Ala Gly Gly Thr Val Leu Gln
        195                 200                 205

Leu Arg Arg Gly Asp Glu Val Trp Ile Glu Lys Asp Pro Ala Lys Gly
    210                 215                 220

Arg Ile Tyr Gln Gly Thr Glu Ala Asp Ser Ile Phe Ser Gly Phe Leu
225                 230                 235                 240

Ile Phe Pro Ser Ala
                245

<210> SEQ ID NO 11
<211> LENGTH: 253
<212> TYPE: PRT
<213> ORGANISM: Mus musculus

<400> SEQUENCE: 11

Met Lys Thr Gln Trp Gly Glu Val Trp Thr His Leu Leu Leu Leu Leu
1               5                   10                  15

Leu Gly Phe Leu His Val Ser Trp Ala Gln Ser Ser Cys Thr Gly Pro
            20                  25                  30

Pro Gly Ile Pro Gly Ile Pro Gly Val Pro Gly Val Pro Gly Ser Asp
        35                  40                  45

Gly Gln Pro Gly Thr Pro Gly Ile Lys Gly Glu Lys Gly Leu Pro Gly
    50                  55                  60

Leu Ala Gly Asp Leu Gly Glu Phe Gly Glu Lys Gly Asp Pro Gly Ile
65                  70                  75                  80

Pro Gly Thr Pro Gly Lys Val Gly Pro Lys Gly Pro Val Gly Pro Lys
                85                  90                  95

Gly Thr Pro Gly Pro Ser Gly Pro Arg Gly Pro Lys Gly Asp Ser Gly
            100                 105                 110

Asp Tyr Gly Ala Thr Gln Lys Val Ala Phe Ser Ala Leu Arg Thr Ile
        115                 120                 125

Asn Ser Pro Leu Arg Pro Asn Gln Val Ile Arg Phe Glu Lys Val Ile
130                 135                 140

Thr Asn Ala Asn Glu Asn Tyr Glu Pro Arg Asn Gly Lys Phe Thr Cys
145                 150                 155                 160

Lys Val Pro Gly Leu Tyr Tyr Phe Thr Tyr His Ala Ser Ser Arg Gly
                165                 170                 175

Asn Leu Cys Val Asn Leu Val Arg Gly Arg Asp Arg Asp Ser Met Gln
            180                 185                 190

Lys Val Val Thr Phe Cys Asp Tyr Ala Gln Asn Thr Phe Gln Val Thr
```

```
                195                 200                 205
Thr Gly Gly Val Val Leu Lys Leu Glu Gln Glu Val Val His Leu
            210                 215                 220

Gln Ala Thr Asp Lys Asn Ser Leu Leu Gly Ile Glu Gly Ala Asn Ser
225                 230                 235                 240

Ile Phe Thr Gly Phe Leu Leu Phe Pro Asp Met Asp Ala
                245                 250

<210> SEQ ID NO 12
<211> LENGTH: 246
<212> TYPE: PRT
<213> ORGANISM: Mus musculus

<400> SEQUENCE: 12

Met Val Val Gly Pro Ser Cys Gln Pro Pro Cys Gly Leu Cys Leu Leu
1               5                   10                  15

Leu Leu Phe Leu Leu Ala Leu Pro Leu Arg Ser Gln Ala Ser Ala Gly
            20                  25                  30

Cys Tyr Gly Ile Pro Gly Met Pro Gly Met Pro Gly Ala Pro Gly Lys
        35                  40                  45

Asp Gly His Asp Gly Leu Gln Gly Pro Lys Gly Glu Pro Gly Ile Pro
    50                  55                  60

Ala Val Pro Gly Thr Arg Gly Pro Lys Gly Gln Lys Gly Glu Pro Gly
65                  70                  75                  80

Met Pro Gly His Arg Gly Lys Asn Gly Pro Arg Gly Thr Ser Gly Leu
                85                  90                  95

Pro Gly Asp Pro Gly Pro Arg Gly Pro Pro Gly Glu Pro Gly Val Glu
            100                 105                 110

Gly Arg Tyr Lys Gln Lys His Gln Ser Val Phe Thr Val Thr Arg Gln
        115                 120                 125

Thr Thr Gln Tyr Pro Glu Ala Asn Ala Leu Val Arg Phe Asn Ser Val
    130                 135                 140

Val Thr Asn Pro Gln Gly His Tyr Asn Pro Ser Thr Gly Lys Phe Thr
145                 150                 155                 160

Cys Glu Val Pro Gly Leu Tyr Tyr Phe Val Tyr Tyr Thr Ser His Thr
                165                 170                 175

Ala Asn Leu Cys Val His Leu Asn Leu Asn Leu Ala Arg Val Ala Ser
            180                 185                 190

Phe Cys Asp His Met Phe Asn Ser Lys Gln Val Ser Ser Gly Gly Val
        195                 200                 205

Leu Leu Arg Leu Gln Arg Gly Asp Glu Val Trp Leu Ser Val Asn Asp
    210                 215                 220

Tyr Asn Gly Met Val Gly Ile Glu Gly Ser Asn Ser Val Phe Ser Gly
225                 230                 235                 240

Phe Leu Leu Phe Pro Asp
                245

<210> SEQ ID NO 13
<211> LENGTH: 245
<212> TYPE: PRT
<213> ORGANISM: Rattus norvegicus

<400> SEQUENCE: 13

Met Glu Thr Ser Gln Gly Trp Leu Val Ala Cys Val Leu Ala Val Thr
1               5                   10                  15

Leu Val Trp Thr Val Ala Glu Asp Val Cys Arg Ala Pro Asn Gly Lys
```

-continued

```
                20                  25                  30
Asp Gly Val Ala Gly Ile Pro Gly Arg Pro Gly Arg Pro Gly Leu Lys
                35                  40                  45
Gly Glu Arg Gly Glu Pro Gly Ala Ala Gly Ile Arg Thr Gly Ile Arg
 50                  55                  60
Gly Leu Lys Gly Asp Met Gly Glu Ser Gly Pro Gly Lys Pro Gly
 65                  70                  75                  80
Asn Val Gly Phe Pro Gly Pro Thr Gly Pro Leu Gly Asn Ser Gly Pro
                85                  90                  95
Gln Gly Leu Lys Gly Val Lys Gly Asn Pro Gly Asn Ile Arg Asp Gln
                100                 105                 110
Pro Arg Pro Ala Phe Ser Ala Ile Arg Gln Asn Pro Thr Tyr Gly
                115                 120                 125
Asn Val Val Val Phe Asp Lys Val Leu Thr Asn Gln Glu Asn Pro Tyr
 130                 135                 140
Gln Asn Arg Thr Gly His Phe Ile Cys Ala Val Pro Gly Phe Tyr Tyr
 145                 150                 155                 160
Phe Thr Phe Gln Val Ile Ser Lys Trp Asp Leu Cys Leu Ser Ile Val
                165                 170                 175
Ser Ser Ser Arg Gly Gln Pro Arg Asn Ser Leu Gly Phe Cys Asp Thr
                180                 185                 190
Asn Ser Lys Gly Leu Phe Gln Val Leu Ala Gly Gly Thr Val Leu Gln
                195                 200                 205
Leu Gln Arg Gly Asp Glu Val Trp Ile Glu Lys Asp Pro Ala Lys Gly
                210                 215                 220
Arg Ile Tyr Gln Gly Thr Glu Ala Asp Ser Ile Phe Ser Gly Phe Leu
 225                 230                 235                 240
Ile Phe Pro Ser Ala
                245

<210> SEQ ID NO 14
<211> LENGTH: 253
<212> TYPE: PRT
<213> ORGANISM: Rattus norvegicus

<400> SEQUENCE: 14

Met Lys Thr Gln Trp Ser Glu Ile Leu Thr Pro Leu Leu Leu Leu
  1               5                  10                  15
Leu Gly Leu Leu His Val Ser Trp Ala Gln Ser Ser Cys Thr Gly Ser
                 20                  25                  30
Pro Gly Ile Pro Gly Val Pro Gly Ile Pro Gly Val Pro Gly Ser Asp
                 35                  40                  45
Gly Lys Pro Gly Thr Pro Gly Ile Lys Gly Glu Lys Gly Leu Pro Gly
  50                  55                  60
Leu Ala Gly Asp His Gly Glu Leu Gly Glu Lys Gly Asp Ala Gly Ile
 65                  70                  75                  80
Pro Gly Ile Pro Gly Lys Val Gly Pro Lys Gly Pro Val Gly Pro Lys
                 85                  90                  95
Gly Ala Pro Gly Pro Pro Gly Pro Arg Gly Pro Lys Gly Gly Ser Gly
                 100                 105                 110
Asp Tyr Lys Ala Thr Gln Lys Val Ala Phe Ser Ala Leu Arg Thr Val
                 115                 120                 125
Asn Ser Ala Leu Arg Pro Asn Gln Ala Ile Arg Phe Glu Lys Val Ile
 130                 135                 140
```

```
Thr Asn Val Asn Asp Asn Tyr Glu Pro Arg Ser Gly Lys Phe Thr Cys
145                 150                 155                 160

Lys Val Pro Gly Leu Tyr Tyr Phe Thr Tyr His Ala Ser Ser Arg Gly
                165                 170                 175

Asn Leu Cys Val Asn Ile Val Arg Gly Arg Asp Arg Asp Arg Met Gln
            180                 185                 190

Lys Val Leu Thr Phe Cys Asp Tyr Ala Gln Asn Thr Phe Gln Val Thr
        195                 200                 205

Thr Gly Gly Val Val Leu Lys Leu Glu Gln Glu Val Val His Leu
    210                 215                 220

Gln Ala Thr Asp Lys Asn Ser Leu Leu Gly Val Glu Gly Ala Asn Ser
225                 230                 235                 240

Ile Phe Thr Gly Phe Leu Leu Phe Pro Asp Met Asp Val
                245                 250
```

<210> SEQ ID NO 15
<211> LENGTH: 245
<212> TYPE: PRT
<213> ORGANISM: Rattus norvegicus

<400> SEQUENCE: 15

```
Met Val Val Gly Thr Ser Cys Gln Pro Gln His Gly Leu Tyr Leu Leu
1               5                   10                  15

Leu Leu Leu Leu Ala Leu Pro Leu Arg Ser Gln Ala Asn Ala Gly Cys
                20                  25                  30

Tyr Gly Ile Pro Gly Met Pro Gly Leu Pro Gly Thr Pro Gly Lys Asp
            35                  40                  45

Gly His Asp Gly Leu Gln Gly Pro Lys Gly Glu Pro Gly Ile Pro Ala
        50                  55                  60

Ile Pro Gly Thr Gln Gly Pro Lys Gly Gln Lys Gly Glu Pro Gly Met
65                  70                  75                  80

Pro Gly His Arg Gly Lys Asn Gly Pro Met Gly Thr Ser Gly Ser Pro
                85                  90                  95

Gly Asp Pro Gly Pro Arg Gly Pro Pro Gly Glu Pro Gly Glu Glu Gly
            100                 105                 110

Arg Tyr Lys Gln Lys His Gln Ser Val Phe Thr Val Thr Arg Gln Thr
        115                 120                 125

Ala Gln Tyr Pro Ala Ala Asn Gly Leu Val Lys Phe Asn Ser Ala Ile
    130                 135                 140

Thr Asn Pro Gln Gly Asp Tyr Asn Thr Asn Thr Gly Lys Phe Thr Cys
145                 150                 155                 160

Lys Val Pro Gly Leu Tyr Tyr Phe Val His His Thr Ser Gln Thr Ala
                165                 170                 175

Asn Leu Cys Val Gln Leu Leu Leu Asn Asn Ala Lys Val Thr Ser Phe
            180                 185                 190

Cys Asp His Met Ser Asn Ser Lys Gln Val Ser Ser Gly Gly Val Leu
        195                 200                 205

Leu Arg Leu Gln Arg Gly Asp Glu Val Trp Leu Ala Val Asn Asp Tyr
    210                 215                 220

Asn Gly Met Val Gly Thr Glu Gly Ser Asp Ser Val Phe Ser Gly Phe
225                 230                 235                 240

Leu Leu Phe Pro Asp
                245
```

<210> SEQ ID NO 16

```
<211> LENGTH: 245
<212> TYPE: PRT
<213> ORGANISM: Canis lupus

<400> SEQUENCE: 16

Met Glu Ala Pro Trp Gly Trp Leu Ala Leu Cys Val Leu Ala Thr Ser
1               5                   10                  15

Leu Ala Ser Ala Val Thr Gln Asp Val Cys Arg Ala Leu Asp Gly Arg
            20                  25                  30

Asp Gly Ala Ala Gly Thr Pro Gly Arg Pro Gly Arg Pro Gly Leu Lys
        35                  40                  45

Gly Glu Gln Gly Glu Pro Gly Ala Pro Gly Met Arg Thr Gly Ile Arg
50                  55                  60

Gly Leu Lys Gly Asp Gln Gly Asp Pro Gly Pro Gly Asn Pro Gly
65                  70                  75                  80

Asn Met Gly Phe Pro Gly Pro Ser Gly Leu Met Gly Leu Pro Gly Ile
                85                  90                  95

Pro Gly Arg Arg Gly Pro Lys Gly Asn Pro Gly Asn Ile Arg Asp Gln
            100                 105                 110

Pro Arg Pro Ala Phe Ser Ala Ile Arg Arg Asn Pro Pro Thr Gly Gly
        115                 120                 125

Asn Val Val Ile Phe Asp Thr Val Ile Thr Asn Gln Glu Gly Pro Tyr
130                 135                 140

Gln Asn His Ser Gly Arg Phe Ile Cys Ala Val Pro Gly Tyr Tyr Tyr
145                 150                 155                 160

Phe Thr Phe Gln Val Val Ser Lys Trp Asp Ile Cys Leu Ser Ile Val
                165                 170                 175

Ser Ser Gly Arg Ala Gln Ile Arg Arg Ser Leu Gly Phe Cys Asp Thr
            180                 185                 190

Asn Ser Lys Gly Ile Phe Gln Val Val Ser Gly Gly Met Ala Leu Gln
        195                 200                 205

Leu Gln Gln Gly Asp Gln Val Trp Ile Glu Lys Asp Pro Ile Lys Gly
    210                 215                 220

Arg Ile Tyr Gln Gly Pro Glu Ala Asp Ser Ile Phe Ser Gly Phe Leu
225                 230                 235                 240

Ile Phe Pro Ser Leu
                245

<210> SEQ ID NO 17
<211> LENGTH: 250
<212> TYPE: PRT
<213> ORGANISM: Canis lupus

<400> SEQUENCE: 17

Met Lys Thr Pro Arg Gly Gly Ile Leu Ala Leu Leu Leu Pro Leu Leu
1               5                   10                  15

Leu Gly Leu Leu Glu Val Ser Trp Ala Gln Ser Cys Thr Gly His Pro
            20                  25                  30

Ala Ile Pro Gly Ile Pro Gly Ile Pro Gly Ala Pro Gly Thr Asp Gly
        35                  40                  45

Thr Pro Gly Thr Pro Gly Thr Lys Gly Glu Lys Gly Leu Pro Gly Leu
    50                  55                  60

Ala Gly Asp His Gly Glu Phe Gly Glu Lys Gly Asp Pro Gly Ile Pro
65                  70                  75                  80

Gly Thr Pro Gly Lys Val Gly Pro Lys Gly Pro Val Gly Pro Lys Gly
                85                  90                  95
```

```
Ser Pro Gly Pro Pro Gly Ala Arg Gly Ala Lys Gly Glu Ser Gly Asp
            100                 105                 110

Tyr Lys Ala Thr Gln Lys Ile Ala Phe Ser Ala Met Arg Thr Ile Asn
            115                 120                 125

Ile Pro Leu Arg Arg Asp Gln Thr Ile Arg Phe Asp His Ile Val Thr
130                 135                 140

Asn Glu Asn Arg Asn Tyr Glu Pro Arg Ser Gly Lys Phe Thr Cys Asn
145                 150                 155                 160

Val Pro Gly Ile Tyr Tyr Phe Ala Tyr His Ala Ser Ser Arg Gly Asn
                165                 170                 175

Leu Cys Val Asn Val Met Arg Gly Arg Glu Arg Met Gln Lys Val Val
            180                 185                 190

Thr Phe Cys Asp Tyr Val Gln Asn Thr Phe Gln Val Thr Thr Gly Ser
            195                 200                 205

Val Val Leu Lys Leu Ser Gln Gly Glu Asn Val Tyr Leu Gln Ala Thr
        210                 215                 220

Asp Lys Asn Ser Leu Leu Gly Met Glu Gly Ala Asn Ser Ile Phe Ser
225                 230                 235                 240

Gly Phe Leu Leu Phe Pro Asp Ala Glu Ala
                245                 250

<210> SEQ ID NO 18
<211> LENGTH: 245
<212> TYPE: PRT
<213> ORGANISM: Canis lupus

<400> SEQUENCE: 18

Met Asp Thr Gly Pro Ser Ser Trp Pro His Leu Gly Leu Asn Leu Leu
1               5                   10                  15

Leu Leu Leu Leu Ala Leu Pro Leu Gly Gly Gln Ala Ser Thr Gly Cys
            20                  25                  30

Tyr Gly Ile Pro Gly Met Pro Gly Leu Pro Gly Ala Pro Gly Lys Asp
        35                  40                  45

Gly His Asp Gly Leu Pro Gly Pro Lys Gly Glu Pro Gly Ile Pro Ala
    50                  55                  60

Ile Pro Gly Thr Arg Gly Pro Lys Gly Gln Lys Gly Glu Pro Gly Thr
65                  70                  75                  80

Pro Gly Tyr Pro Gly Lys Asn Gly Pro Met Gly Thr Pro Gly Ile Pro
                85                  90                  95

Gly Val Pro Gly Pro Val Gly Pro Pro Gly Glu Pro Gly Glu Glu Gly
            100                 105                 110

Arg Tyr Lys Gln Lys His Gln Ser Val Phe Thr Val Thr Arg Gln Thr
        115                 120                 125

Ala Gln Tyr Pro Leu Ala Asn Asn Leu Val Lys Phe Asn Thr Val Ile
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Thr Ser Leu Thr Ser
                165                 170                 175

Asn Leu Cys Val His Leu Tyr Arg Ser Gly Thr Arg Val Thr Thr Phe
            180                 185                 190

Cys Asp His Met Ser Asn Ser Lys Gln Val Ser Ser Gly Gly Val Leu
        195                 200                 205

Leu Arg Leu Gln Met Gly Glu Gln Val Trp Leu Ala Val Asn Asp Tyr
```

-continued

```
                210                 215                 220
Asn Gly Met Val Gly Thr Glu Gly Ser Asp Ser Val Phe Ser Gly Phe
225                 230                 235                 240

Leu Leu Phe Pro Asp
                245

<210> SEQ ID NO 19
<211> LENGTH: 247
<212> TYPE: PRT
<213> ORGANISM: Danio rerio

<400> SEQUENCE: 19

Met Gln Pro Ser Ala Phe Phe Ala Phe Leu Trp Ala Gly Ala Leu Phe
1               5                   10                  15

Pro Phe Ser Phe Cys Gln Asp Glu Cys Val Lys His Gly Arg Asn Gly
            20                  25                  30

Ala Asp Gly Pro Asn Gly Arg Asp Gly Leu Pro Gly Pro Lys Gly Glu
        35                  40                  45

Lys Gly Glu Pro Ala Leu Gln Val Lys Leu Ser Ser Ile Ala Leu Glu
    50                  55                  60

Glu Leu Lys Gly Asp Met Gly Val Arg Gly Pro Pro Gly Glu Pro Gly
65                  70                  75                  80

Leu Glu Gly Leu Met Gly Ala Ile Gly Pro Arg Gly Pro Leu Gly Pro
                85                  90                  95

Ala Gly Pro Arg Gly Ser Ser Val Gly Ala Asp Gly Ala Lys Ala Ser
            100                 105                 110

Glu Lys Pro Ala Phe Ser Val Leu Arg Asn Glu Ala Ser Gln Ala Gln
        115                 120                 125

Tyr Lys Gln Pro Val Thr Phe Asn Asp Lys Leu Ser Asp Ala Asn Asp
    130                 135                 140

Asp Phe Gln Ile Lys Thr Gly Tyr Phe Thr Cys Lys Val Pro Gly Val
145                 150                 155                 160

Tyr Tyr Phe Val Phe His Ala Ser Ser Glu Gly Arg Leu Cys Leu Arg
                165                 170                 175

Leu Lys Ser Thr Ser Ala Pro Pro Val Ser Leu Ser Phe Cys Asp Phe
            180                 185                 190

Asn Ser Lys Ser Val Ser Leu Val Val Ser Gly Gly Ala Val Leu Thr
        195                 200                 205

Leu Leu Lys Gly Asp Lys Val Trp Ile Glu Pro Phe Ala Gly Asp Gly
    210                 215                 220

Gly Val Gly Gln Met Pro Lys Arg Leu Tyr Ala Val Phe Asn Gly Phe
225                 230                 235                 240

Leu Ile Tyr Arg Asn Ala Glu
                245

<210> SEQ ID NO 20
<211> LENGTH: 242
<212> TYPE: PRT
<213> ORGANISM: Danio rerio

<400> SEQUENCE: 20

Met Leu Phe Ala Leu Met Ser Ala His Val Val Pro Gln Leu Ala Ile
1               5                   10                  15

Met Leu Leu Leu Val Thr Ser Ser Met Ser Glu Thr Cys Ala Gly Asn
            20                  25                  30

Lys Gly Phe Pro Gly Thr Pro Gly Ile Pro Gly Val Pro Gly Thr Asp
```

```
                    35                  40                  45
Gly Lys Asp Gly Ala Lys Gly Glu Lys Gly Asp Pro Gly Glu Asn Glu
                50                  55                  60
Val Gln Met Thr Gly Pro Lys Gly Asp Pro Gly Lys Pro Gly Leu Pro
 65                  70                  75                  80
Gly Arg Pro Gly Val Lys Gly Pro Glu Gly Pro Gln Gly Pro Pro Gly
                            85                  90                  95
Pro Pro Gly Pro Lys Gly Gln Arg Gly Val Leu Ser Gly Lys Val Ala
                100                 105                 110
Pro Asp Gln Tyr Phe Val Phe Ser Tyr Lys Lys Ser Gln Lys Leu Glu
                115                 120                 125
Lys Ile Leu Gln Asp Lys Leu Val Val Phe Asp Val Pro Leu Ile Thr
            130                 135                 140
Gly Ile Asp Gly Val Leu Asp Gly Glu Gly Tyr Phe Asp Val Thr Ile
145                 150                 155                 160
Thr Gly Met Tyr Tyr Ile Ser Tyr Gln Ile Ser Phe Gln Gln Ser Ala
                            165                 170                 175
Cys Leu Lys Ile Gln Ile Gly Ala Glu Glu Lys Val Lys Phe Cys Asp
                180                 185                 190
Ser Pro Lys Leu Ile Leu Gly Thr Ala Ala Ser Val Val Leu Lys Leu
                195                 200                 205
Asn Lys Gly Asp Lys Val Ser Val Gln Ser Thr Gly Glu Ser Thr Val
            210                 215                 220
Phe Ser Arg Asp Thr Asp Cys Thr Phe Thr Gly Phe Met Leu Phe Pro
225                 230                 235                 240
Ile Lys

<210> SEQ ID NO 21
<211> LENGTH: 244
<212> TYPE: PRT
<213> ORGANISM: Danio rerio

<400> SEQUENCE: 21

Met Phe Gly Gly His Leu Ile Leu Val Ser Leu Ser Ala Ser Leu
  1               5                  10                  15

Cys Leu Cys Leu Ala Ser Ala Asp Thr Cys Pro Ala Gly Ala Met Pro
                20                  25                  30

Gly Leu Pro Gly Ile Pro Gly Phe Pro Gly Arg Asp Gly Arg Gln Gly
                35                  40                  45

Met Lys Gly Glu Lys Gly Asp Leu Gly Ile Pro Ile Lys Pro Gly Asp
            50                  55                  60

Thr Val Lys Lys Gly Glu Arg Gly Ala Phe Gly Leu Lys Gly Pro Pro
 65                  70                  75                  80

Gly Lys Arg Gly Pro His Gly Asp Pro Gly Ile Met Gly Pro Pro Gly
                            85                  90                  95

Pro Pro Gly Glu Pro Gly Glu Ala Gly Leu Val Asp Val Ser Gly Ser
                100                 105                 110

Gln Leu Gln Ser Ala Phe Ser Val Ser Arg His Thr Arg Ile Pro Pro
                115                 120                 125

Asp Ala Asn Lys Val Ile Arg Phe Ser Lys Val Ile Thr Asn Pro Gln
            130                 135                 140

Gly His Phe Ser Thr Asp Glu Ser Lys Phe Val Cys Lys Ile Pro Gly
145                 150                 155                 160

Thr Tyr Tyr Phe Val Leu His Ala Ser Ser His Asp Lys Lys Leu Cys
```

```
            165                 170                 175
Val Ile Leu Val His Asp Asp Lys Asn Leu Val Ser Phe Cys Asp His
            180                 185                 190

Thr Gln Arg Gly Ser Gln Gln Val Ser Ser Gly Gly Leu Ser Leu Tyr
        195                 200                 205

Leu Lys Glu Asn Glu Lys Val Trp Leu Met Thr Asn Ala Leu Asn Gly
    210                 215                 220

Met Tyr Ala Thr Ala Asp Arg Ala Asp Ser Val Phe Ser Gly Phe Leu
225                 230                 235                 240

Ile His Ala His
```

<210> SEQ ID NO 22
<211> LENGTH: 13
<212> TYPE: PRT
<213> ORGANISM: Macaca fascicularis

<400> SEQUENCE: 22

```
Val Gly Tyr Pro Gly Pro Ser Gly Pro Leu Gly Ala Arg
1               5                   10
```

<210> SEQ ID NO 23
<211> LENGTH: 11
<212> TYPE: PRT
<213> ORGANISM: Macaca fascicularis

<400> SEQUENCE: 23

```
Asp Gln Pro Arg Pro Ala Phe Ser Ala Ile Arg
1               5                   10
```

<210> SEQ ID NO 24
<211> LENGTH: 28
<212> TYPE: PRT
<213> ORGANISM: Macaca fascicularis

<400> SEQUENCE: 24

```
Asn Pro Pro Met Gly Gly Asn Val Val Ile Phe Asp Thr Val Ile Thr
1               5                   10                  15

Asn Gln Glu Glu Pro Tyr Gln Asn His Ser Gly Arg
            20                  25
```

<210> SEQ ID NO 25
<211> LENGTH: 30
<212> TYPE: PRT
<213> ORGANISM: Macaca fascicularis

<400> SEQUENCE: 25

```
Phe Val Cys Thr Val Pro Gly Tyr Tyr Tyr Phe Thr Phe Gln Val Leu
1               5                   10                  15

Ser Gln Trp Glu Ile Cys Leu Ser Ile Val Ser Ser Ser Arg
            20                  25                  30
```

<210> SEQ ID NO 26
<211> LENGTH: 10
<212> TYPE: PRT
<213> ORGANISM: Macaca fascicularis

<400> SEQUENCE: 26

```
Ser Leu Gly Phe Cys Asp Thr Thr Asn Lys
1               5                   10
```

<210> SEQ ID NO 27

```
<211> LENGTH: 26
<212> TYPE: PRT
<213> ORGANISM: Macaca fascicularis

<400> SEQUENCE: 27

Gly Leu Phe Val Val Ser Gly Gly Met Val Leu Gln Leu Gln Gln Gly
1               5                   10                  15

Asp Gln Val Trp Val Glu Lys Asp Pro Lys
            20                  25

<210> SEQ ID NO 28
<211> LENGTH: 22
<212> TYPE: PRT
<213> ORGANISM: Macaca fascicularis

<400> SEQUENCE: 28

Gly His Ile Tyr Gln Gly Ser Glu Ala Asp Ser Val Phe Ser Gly Phe
1               5                   10                  15

Leu Ile Phe Pro Ser Ala
            20

<210> SEQ ID NO 29
<211> LENGTH: 7
<212> TYPE: PRT
<213> ORGANISM: Macaca fascicularis

<400> SEQUENCE: 29

Ile Ala Phe Ser Ala Thr Arg
1               5

<210> SEQ ID NO 30
<211> LENGTH: 8
<212> TYPE: PRT
<213> ORGANISM: Macaca fascicularis

<400> SEQUENCE: 30

Thr Ile Asn Val Pro Leu Arg Arg
1               5

<210> SEQ ID NO 31
<211> LENGTH: 15
<212> TYPE: PRT
<213> ORGANISM: Macaca fascicularis

<400> SEQUENCE: 31

Phe Asp His Val Ile Thr Asn Met Asn Asn Tyr Glu Pro Arg
1               5                   10                  15

<210> SEQ ID NO 32
<211> LENGTH: 14
<212> TYPE: PRT
<213> ORGANISM: Macaca fascicularis

<400> SEQUENCE: 32

Val Pro Gly Leu Tyr Tyr Phe Thr Tyr His Ala Ser Ser Arg
1               5                   10

<210> SEQ ID NO 33
<211> LENGTH: 9
<212> TYPE: PRT
<213> ORGANISM: Macaca fascicularis

<400> SEQUENCE: 33

Gly Asn Leu Cys Val Asn Leu Met Arg
```

```
<210> SEQ ID NO 34
<211> LENGTH: 14
<212> TYPE: PRT
<213> ORGANISM: Macaca fascicularis

<400> SEQUENCE: 34

Leu Glu Gln Gly Glu Asn Val Phe Leu Gln Ala Thr Asp Lys
1               5                   10

<210> SEQ ID NO 35
<211> LENGTH: 9
<212> TYPE: PRT
<213> ORGANISM: Macaca fascicularis

<400> SEQUENCE: 35

Phe Gln Ser Val Phe Thr Val Thr Arg
1               5

<210> SEQ ID NO 36
<211> LENGTH: 13
<212> TYPE: PRT
<213> ORGANISM: Macaca fascicularis

<400> SEQUENCE: 36

Gln Thr His Gln Pro Pro Ala Pro Asn Ser Leu Ile Arg
1               5                   10

<210> SEQ ID NO 37
<211> LENGTH: 18
<212> TYPE: PRT
<213> ORGANISM: Macaca fascicularis

<400> SEQUENCE: 37

Phe Asn Ala Val Leu Thr Asn Pro Gln Gly Asp Tyr Asp Thr Ser Thr
1               5                   10                  15

Gly Lys

<210> SEQ ID NO 38
<211> LENGTH: 23
<212> TYPE: PRT
<213> ORGANISM: Macaca fascicularis

<400> SEQUENCE: 38

Val Pro Gly Leu Tyr Tyr Phe Val Tyr His Ala Ser His Thr Ala Asn
1               5                   10                  15

Leu Cys Val Leu Leu Tyr Arg
            20

<210> SEQ ID NO 39
<211> LENGTH: 10
<212> TYPE: PRT
<213> ORGANISM: Macaca fascicularis

<400> SEQUENCE: 39

Val Val Thr Phe Cys Gly His Thr Ser Lys
1               5                   10

<210> SEQ ID NO 40
<211> LENGTH: 12
<212> TYPE: PRT
<213> ORGANISM: Macaca fascicularis
```

```
<400> SEQUENCE: 40

Thr Asn Gln Val Asn Ser Gly Gly Val Leu Leu Arg
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Modified Peptide
<220> FEATURE:
<221> NAME/KEY: MOD_RES
<222> LOCATION: (5)..(5)
<223> OTHER INFORMATION: Carbamidomethylation

<400> SEQUENCE: 41

Ser Leu Gly Phe Cys Asp Thr Thr Asn Lys
1               5                   10
```

USE OF LC-MS/MS TO QUANTITATE PROTEIN BIOMARKERS

RELATED APPLICATIONS

This application claims priority to, and the benefit of, U.S. Provisional Application No. 62/715,973, filed on Aug. 8, 2018, the contents of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Aug. 6, 2019, is named "REGE-015-001US_SeqList_ST25.txt" and is 50,295 bytes in size.

BACKGROUND OF THE INVENTION

C1q is an important, druggable protein involved in the complement system of the innate immune system. There are currently immuno-based methods for determining the concentration of C1q in biological samples derived from humans. However, there exists limited immunoreagents for assaying the abundance of C1q in samples derived from non-human primates, an important model organism in preclinical research and trials. Thus, there is a need in the art for methods and compositions directed towards determining C1q concentration in samples derived from human, non-human primate and other model organisms that are rapid, specific and accurate, and that do not require the costly and time-consuming development of immunoreagents. The present disclosure addresses these needs.

SUMMARY OF THE INVENTION

The present disclosure provides an assay comprising: (1) contacting a biological sample with at least one proteolytic enzyme to produce at least one peptide fragment of the protein C1q present in the biological sample; and (2) performing selected reaction monitoring mass spectrometry (SRM-MS) to measure the abundance of the at least one C1q peptide fragment, wherein the abundance of the at least one C1q peptide fragment determines the concentration of C1q in the biological sample.

The preceding assay can further comprise between step (1) and step (2), adding to the biological sample at least one labeled, synthetic C1q peptide fragment comprising an amino acid sequence identical to the amino acid sequence of the at least one C1q peptide fragment.

Measuring the abundance of the at least one C1q peptide fragment in the preceding assay can comprise comparing a signal corresponding to the at least one C1q peptide generated by SRM-MS to a standard curve.

The present disclosure provides an assay comprising: (1) contacting a biological sample with at least one proteolytic enzyme to produce at least one peptide fragment of the protein C1q present in the biological sample; (2) performing selected reaction monitoring mass spectrometry (SRM-MS) to generate a signal corresponding to the at least one C1q peptide fragment; and (3) determining the abundance of the at least one C1q peptide fragment by comparing the signal to a standard curve, wherein the abundance of the at least one C1q peptide fragment determines the concentration of C1q in the biological sample.

The preceding assay can further comprise between step (1) and step (2), adding to the biological sample at least one labeled, synthetic peptide fragment comprising an amino acid sequence identical to the amino acid sequence of the at least one C1q peptide fragment, and between step (2) and step (3), performing SRM-MS to generate a signal corresponding to the at least one labeled, synthetic peptide.

The biological sample can be a blood sample. The biological sample can be a human sample. The biological sample can be a non-human primate sample.

The at least one peptide fragment can comprise at least 5 amino acids. The at least one peptide fragment can comprise a peptide selected from Table 2.

The at least one peptide fragment can comprise SLGFCDTTNK (SEQ ID NO: 26), IAFSATR (SEQ ID NO: 29) or QTHQPPAPNSLIR (SEQ ID NO: 36). The at least one peptide fragment can comprise at least two of SLGFCDTTNK (SEQ ID NO: 26), IAFSATR (SEQ ID NO: 29) or QTHQPPAPNSLIR (SEQ ID NO: 36). The at least one peptide fragment can comprise each of SLGFCDTTNK (SEQ ID NO: 26), IAFSATR (SEQ ID NO: 29) and QTHQPPAPNSLIR (SEQ ID NO: 36).

The selected reaction monitoring mass spectrometry can be LC-SRM-MS/MS.

The at least one proteolytic enzyme can be trypsin.

A standard curve can be produced using a method comprising: (a) preparing at least two C1q concentration standards by mixing known quantities of purified C1q protein and C1q-depleted serum; (b) adding to the at least two C1q concentration standards at least one labeled, synthetic peptide fragment with an amino acid sequence identical to an at least one peptide fragment of C1q that is expected to be produced following contacting the C1q concentration standard with a proteolytic enzyme; (c) contacting the at least two labeled C1q concentration standards with a proteolytic enzyme to produce at least one peptide fragment of C1q; (d) performing selected reaction monitoring mass spectrometry to determine the strength of the signal that corresponds to the at least one peptide fragment of C1q and the strength of the signal that corresponds to the at least one labeled, synthetic peptide fragment in each of the at least two labeled C1q concentration standards; and (e) determining a standard curve using the signals and the known quantities of C1q protein.

The present disclosure provides a composition comprising at least one isolated synthetic peptide, said composition comprising at least one isolated synthetic peptide with an amino acid sequence selected from the protein C1q.

A composition comprising at least one isolated synthetic peptide, said composition comprising at least one isolated synthetic peptide with an amino acid sequence selected from the protein C1q, wherein the amino acid sequence selected from the protein C1q is the sequence of a C1q peptide fragment generated by contacting C1q with at least one proteolytic enzyme.

The C1q protein can be from a human. The C1q protein can be from a non-human primate.

The at least one isolated synthetic peptide can comprise at least 5 amino acids.

The amino acid sequence selected from the protein C1q can be the sequence of a C1q peptide fragment generated by contacting C1q with at least one proteolytic enzyme. The at least one proteolytic enzyme can be trypsin.

The at least one isolated synthetic peptide can be labeled.

The at least one isolated synthetic peptide can comprise a peptide selected from Table 2.

The at least one isolated synthetic peptide can comprise SLGFCDTTNK (SEQ ID NO: 26), IAFSATR (SEQ ID NO: 29) or QTHQPPAPNSLIR (SEQ ID NO: 36). The cysteine in the synthetic peptide SLGFCDTTNK (SEQ ID NO: 26) can be modified. The modification can be carbamidomethylation.

The present disclosure provides a composition comprising at least one transition ion pair, said composition comprising at least one transition ion pair of the protein C1q, wherein the at least one transition ion pair consists of a precursor ion with a corresponding m/z and a fragment ion with a corresponding ion m/z.

The C1q protein can be from a human. The C1q protein can be from a non-human primate.

The present disclosure provides a composition comprising at least one transition ion pair, said composition comprising at least one transition ion pair of the protein C1q, wherein the at least one transition ion pair consists of a precursor ion with a corresponding m/z and a fragment ion with a corresponding ion m/z, and wherein the transition ion pair is selected from precursor SLGFC(Cam)DTTNK (SEQ ID NO: 41) transition pair 571.8-942.3, precursor IAFSATR (SEQ ID NO: 29) transition pair 383.1-581.1 and precursor QTHQPPAPNSLIR (SEQ ID NO: 36) transition pair 487.0-350.3. Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION OF THE INVENTION

Figure 1:
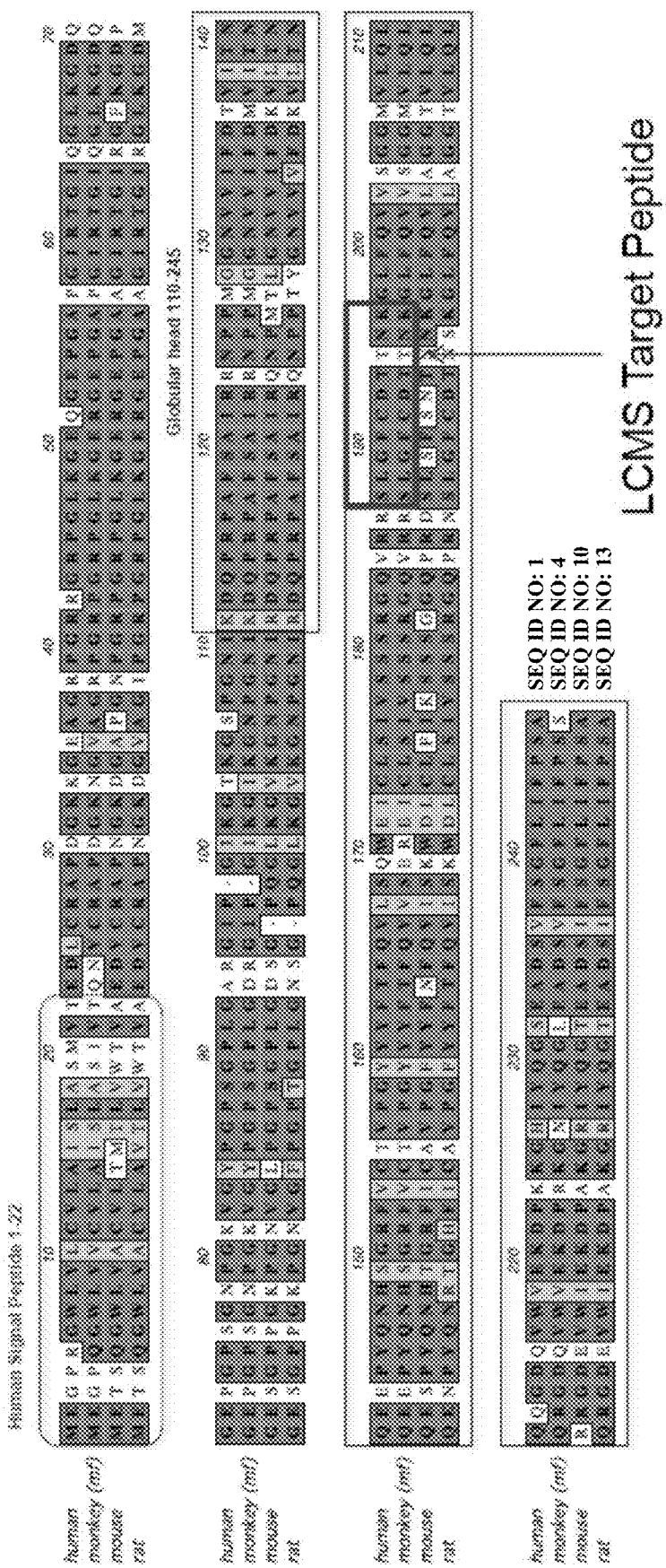
FIG. 1 is the amino acid sequence alignment of the A subunit of C1q from human, monkey, mouse and rat.

The present disclosure provides methods and compositions for determining the abundance and/or concentration of protein biomarkers in a biological sample. In some aspects, this protein biomarker is the protein C1q. In some aspects, the methods of the present disclosure comprise liquid chromatography selected reaction monitoring mass spectrometry (LC-SRM-MS) analysis.

The complement component 1q (C1q) is a protein complex involved in the complement system, which is part of the innate immune system. C1q together with C1r and C1s form the C1 complex. C1q is a 400 kDa protein consisting of 18 polypeptide subunits: six A-subunits, six B-subunits, and six C-subunits. Complement inhibitors have been successfully used in treating several diseases. C1q-targeted monoclonal antibodies have potential as therapy for autoimmune diseases involving the classical complement pathway. The development of C1q-targeting treatment approaches requires methods for determining the concentration of C1q levels in biological samples during laboratory research and clinical trials. To date, determining the C1q abundance in human samples requires the use of immunoassays, such as ELISA. Furthermore, there exists limited immunoreagents for assaying C1q in non-human primate samples, which are an important aspect of pre-clinical research and trials. Thus, there exists a need for an improved assay for determining C1q concentration in biological samples derived from humans, non-human primates and other model organisms.

Liquid chromatography selected reaction monitoring mass spectrometry (LC-SRM-MS) methods are highly desirable because LC-SRM-MS methods provide both absolute structural specificity for the target protein and relative or absolute measurement of the target protein concentration when suitable internal standards are utilized.

Methods of the Present Disclosure

Various methods of the present disclosure are described in full detail herein.

The present disclosure provides a method comprising an assay comprising: (1) contacting a biological sample with at least one proteolytic enzyme to produce at least one peptide fragment of the protein C1q present in the biological sample; and (2) performing selected reaction monitoring mass spectrometry (SRM-MS) to measure the abundance of the at least one C1q peptide fragment, wherein the abundance of the at least one C1q peptide fragment determines the concentration of C1q in the biological sample.

In some aspects, the preceding method can further comprise between step (1) and step (2), adding to the biological sample at least one labeled synthetic C1q peptide fragment comprising an amino acid sequence identical to the amino acid sequence of the at least one C1q peptide fragment.

The present disclosure also provides a method comprising an assay comprising: (1) contacting a biological sample with at least one proteolytic enzyme to produce at least one peptide fragment of the protein C1q present in the biological sample; (2) performing selected reaction monitoring mass spectrometry (SRM-MS) to generate a signal corresponding to the at least one C1q peptide fragment; and (3) determining the abundance of the at least one C1q peptide fragment by comparing the signal to a standard curve, wherein the abundance of the at least one C1q peptide fragment determines the concentration of C1q in the biological sample.

In some aspects, the preceding method can further comprise between step (1) and step (2), adding to the biological sample at least one labeled, synthetic peptide fragment comprising an amino acid sequence identical to the amino acid sequence of the at least one C1q peptide fragment, and between step (2) and step (3), performing SRM-MS to generate a signal corresponding to the at least one labeled, synthetic peptide.

In some aspects, the biological sample can be a blood sample. In preferred aspects, the biological sample can be a serum sample. In some aspects, the biological sample can be a human sample. Alternatively, the biological sample can be a non-human primate sample. The non-human primate can be *Macaca fascicularis* or *Macaca mulatta*.

In some aspects, the C1q protein can be human C1q protein. In other aspects, the C1q protein is *Macaca fascicularis* C1q protein. In yet another aspect, the C1q protein can be *Macaca mulatta* C1q protein. The C1q protein can comprise any of the sequences show in Table 1.

TABLE 1

Sequences of C1q proteins

| Species | Subunit | NCBI ref # | Sequence | SEQ ID NO |
|---|---|---|---|---|
| Human (*Homo sapiens*) | A | NP_057075 | MEGPRGWLVLCVLAISLASMVTEDLCRAPD GKKGEAGRPGRRGRPGLKGEQGEPGAPGIR TGIQGLKGDQGEPGPSGNPGKVGYPGPSGP LGARGIPGIKGTKGSPGNIKDQPRPAFSAI RRNPPMGGNVVIFDTVITNQEEPYQNHSGR FVCTVPGYYYFTFQVLSQWEICLSIVSSSR GQVRRSLGFCDTTNKGLFQVVSGGMVLQLQ QGDQVWVEKDPKKGHIYQGSEADSVFSGFL IFPSA | 1 |
| | B | NP_000482 | MMMKIPWGSIPVLMLLLLLGLIDISQAQLS CTGPPAIPGIPGIPGTPGPDGQPGTPGIKG EKGLPGLAGDHGEFGEKGDPGIPGNPGKVG PKGPMGPKGGPGAPGAPGPKGESGDYKATQ KIAFSATRTINVPLRRDQTIRFDHVITNMN NNYEPRSGKFTCKVPGLYYFTYHASSRGNL CVNLMRGRERAQKVVTFCDYAYNTFQVTTG GMVLKLEQGENVFLQATDKNSLLGMEGANS IFSGFLLFPDMEA | 2 |
| | C | NP_758957 | MDVGPSSLPHLGLKLLLLLLLLPLRGQANT GCYGIPGMPGLPGAPGKDGYDGLPGPKGEP GIPAIPGIRGPKGQKGEPGLPGHPGKNGPM GPPGMPGVPGPMGIPGEPGEEGRYKQKFQS | 3 |

TABLE 1-continued

Sequences of C1q proteins

| Species | Subunit | NCBI ref # | Sequence | SEQ ID NO |
|---|---|---|---|---|
| | | | VFTVTRQTHQPPAPNSLIRFNAVLTNPQGD YDTSTGKFTCKVPGLYYFVYHASHTANLCV LLYRSGVKVVTFCGHTSKTNQVNSGGVLLR LQVGEEVWLAVNDYYDMVGIQGSDSVFSGF LLFPD | |
| Cynomolgus monkey (Macaca fascicularis) | A | XP_015296582 | MEGPQGWLVVCVLAISLASIVTQNVCRAPD GKNGVAGRPGRPGRPGLKGERGEPGAPGIR TGIQGLKGDQGEPGPSGNPGKVGYPGPSGP LGDRGIPGIKGIKGNPGNIKDQPRPAFSAI RRNPPMGGNVVIFDMVITNQEEPYQNHSGR FVCTVPGYYYFTFQVVSEREICLSIVSSSR GQVRRSLGFCDTTNKGLFQVVSGGMVLQLQ RGDQVWVEKDPRKGNIYQGLEADSVFSGFL IFPSS | 4 |
| | B | XP_005544557 | MMMKILWGSIPVLMLLLLLGLLDVSWAQGS CTGPPAIPGTPGIPGTPGSDGQPGTPGIKG EKGLPGLAGDHGEFGEKGDPGIPGNPGKVG PKGPMGPKGGPGAPGAPGPKGESGDYKATQ KIAFSATRTVNTPLRRDQTIRFDHVITNMN NNYEPRSGKFTCRVPGLYYFTYHASSRGNL CVKLMRGRERPQKVVTFCDYAYNTFQVTTG GMVLKLEQGENVFLQATDKNSLLGMEGANS IFSGFLLFPDVEA | 5 |
| | C | XP_015296579 | MDVGPSSLPHLGLKLLLLLLLLPLRGQANT GCYGIPGMPGLPGAPGKDGHDGLPGPKGEP GIPAIPGTRGPKGQKGEPGTPGHPGKNGPM GPPGMPGVPGPMGIPGEPGEEGRYKQKYQS VFTVARQTHQPPAPNSLIRFNAVLTNPQGD YDTSTGKFTCKVPGLYYFVYHASHTANLCV LLYRGGVKVVTFCGHTSQANQVNSGGVLLR LQVGEEVWLGVNDYYDMVGIQGSDSVFSGF LLFPD | 6 |
| Rhesus monkey (Macaca mulatta) | A | XP_014985904 | MEGPQGWLVVCVLAISLASIVTQNVCRAPD GKNGVAGRPGRPGRPGLKGERGEPGAPGIR TGIQGLKGDQGEPGPSGNPGKVGYPGPSGP LGDRGIPGIKGIKGNPGNIKDQPRPAFSAI RRNPPMGGNVVIFDMVITNQEEPYQNHSGR FVCTVPGYYYFTFQVVSEREICLSIVSSSR GQVRRSLGFCDTTNKGLFQVVSGGMVLQLQ RGDQVWVEKDPRKGNIYQGLEADSVFSGFL IFPST | 7 |
| | B | XP_014985910 | MMMKILWGSIPVLMLLLLLGLLDVSWAQGS CTGPPAIPGTPGIPGTPGSDGQPGTPGIKG EKGLPGLAGDHGEFGEKGDPGIPGNPGKVG PKGPMGPKGGPGAPGAPGPKGESGDYKATQ KIAFSATRTINTPLRRDQTIRFDHVITNMN NNYEPRSGKFTCRVPGLYYFTYHASSRGNL CVKLMRGRERPQKVVTFCDYAYNTFQVTTG GMVLKLEQGENVFLQATDKNSLLGMEGANS IFSGFLLFPDVEA | 8 |
| | C | NP_001253737 | MDVGPSSLPHLGLKLLLLLLLLPLRGQANT GCYGIPGMPGLPGAPGKDGHDGLPGPKGEP GIPAIPGTRGPKGQKGEPGTPGHPGKNGPM GPPGMPGVPGPMGIPGEPGEEGRYKQKYQS VFTVARQTHQPPAPNSLIRFNAVLTNPQGD YDTSTGKFTCKVPGLYYFVYHASHTANLCV LLYRGGVKVVTFCGHTSQANQVNSGGVLLR LQVGEEVWLGVNDYYDMVGIQGSDSVFSGF LLFPD | 9 |
| Mouse (Mus musculus) | A | NP_031598 | METSQGWLVACVLTMTLVWTVAEDVCRAPN GKDGAPGNPGRPGRPGLKGERGEPGAAGIR TGIRGFKGDPGESGPPGKPGNVGLPGPSGP LGDSGPQGLKGVKGNPGNIRDQPRPAFSAI RQNPMTLGNVVIFDKVLTNQESPYQNHTGR | 10 |

TABLE 1-continued

Sequences of C1q proteins

| Species | Subunit | NCBI ref # | Sequence | SEQ ID NO |
|---|---|---|---|---|
| | | | FICAVPGFYYFNFQVISKWDLCLFIKSSSG GQPRDSLSFSNTNNKGLFQVLAGGTVLQLR RGDEVWIEKDPAKGRIYQGTEADSIFSGFL IFPSA | |
| | B | NP_033907 | MKTQWGEVWTHLLLLLLGFLHVSWAQSSCT GPPGIPGIPGVPGVPGSDGQPGTPGIKGEK GLPGLAGDLGEFGEKGDPGIPGTPGKVGPK GPVGPKGTPGPSGPRGPKGDSGDYGATQKV AFSALRTINSPLRPNQVIRFEKVITNANEN YEPRNGKFTCKVPGLYYFTYHASSRGNLCV NLVRGRDRDSMQKVVTFCDYAQNTFQVTTG GVVLKLEQEEVVHLQATDKNSLLGIEGANS IFTGFLLFPDMDA | 11 |
| | C | NP_031600 | MVVGPSCQPPCGLCLLLLFLLALPLRSQAS AGCYGIPGMPGMPGAPGKDGHDGLQGPKGE PGIPAVPGTRGPKGQKGEPGMPGHRGKNGP RGTSGLPGDPGPRGPPGEPGVEGRYKQKHQ SVFTVTRQTTQYPEANALVRFNSVVTNPQG HYNPSTGKFTCEVPGLYYFVYYTSHTANLC VHLNLNLARVASFCDHMFNSKQVSSGGVLL RLQRGDEVWLSVNDYNGMVGIEGSNSVFSG FLLFPD | 12 |
| Rat (Rattus norvegicus) | A | NP_001008515 | METSQGWLVACVLAVTLVVVTVAEDVCRAP NGKDGVAGIPGRPGRPGLKGERGEPGAAGI RTGIRGLKGDMGESGPPGKPGNVGFPGPTG PLGNSGPQGLKGVKGNPGNIRDQPRPAFSA IRQNPPTYGNVVVFDKVLTNQENPYQNRTG HFICAVPGFYYFTQVISKWDLCLSIVSSS RGQPRNSLGFCDTNSKGLFQVLAGGTVLQL QRGDEVWIEKDPAKGRIYQGTEADSIFSGF LIFPSA | 13 |
| | B | NP_062135 | MKTQWSEILTPLLLLLLGLLHVSWAQSSCT GSPGIPGVPGIPGVPGSDGKPGTPGIKGEK GLPGLAGDHGELGEKGDAGIPGIPGKVGPK GPVGPKGAPGPPGPRGPKGGSGDYKATQKV AFSALRTVNSALRPNQAIRFEKVITNVNDN YEPRSGKFTCKVPGLYYFTYHASSRGNLCV NIVRGRDRDRMQKVLTFCDYAQNTFQVTTG GVVLKLEQEEVVHLQATDKNSLLGVEGANS IFTGFLLFPDMDV | 14 |
| | C | NP_001008524 | MVVGTSCQPQHGLYLLLLLLALPLRSQANA GCYGIPGMPGLPGTPGKDGHDGLQGPKGEP GIPAIPGTQGPKGQKGEPGMPGHRGKNGPM GTSGSPGDPGPRGPPGEPGEEGRYKQKHQS VFTVTRQTAQYPAANGLVKFNSAITNPQGD YNTNTGKFTCKVPGLYYFVHHTSQTANLCV QLLLNNAKVTSFCDHMSNSKQVSSGGVLLR LQRGDEVWLAVNDYNGMVGTEGSDSVFSGF LLFPD | 15 |
| Dog (Canis lupus familiaris) | A | XP_535367 | MEAPWGWLALCVLATSLASAVTQDVCRALD GRDGAAGTPGRPGRPGLKGEQGEPGAPGMR TGIRGLKGDQGDPGPPGNPGNMGFPGPSGL MGLPGIPGRRGPKGNPGNIRDQPRPAFSAI RRNPPTGGNVVIFDTVITNQEGPYQNHSGR FICAVPGYYYFTQVVSKWDICLSIVSSGR AQIRRSLGFCDTNSKGIFQVVSGGMALQLQ QGDQVWIEKDPIKGRIYQGPEADSIFSGFL IFPSL | 16 |
| | B | XP_544507 | MKTPRGGILALLLPLLLGLLEVSWAQSCTG HPAIPGIPGIPGAPGTDGTPGTPGTKGEKG LPGLAGDHGEFGEKGDPGIPGTPGKVGPKG PVGPKGSPGPPGARGAKGESGDYKATQKIA FSAMRTINIPLRRDQTIRFDHIVTNENRNY EPRSGKFTCNVPGIYYFAYHASSRGNLCVN VMRGRERMQKVVTFCDYVQNTFQVTTGSVV LKLSQGENVYLQATDKNSLLGMEGANSIFS GFLLFPDAEA | 17 |

TABLE 1-continued

Sequences of C1q proteins

| Species | Subunit | NCBI ref # | Sequence | SEQ ID NO |
|---|---|---|---|---|
| | C | XP_003433793 | MDTGPSSWPHLGLNLLLLLLALPLGGQAST GCYGIPGMPGLPGAPGKDGHDGLPGPKGEP GIPAIPGTRGPKGQKGEPGTPGYPGKNGPM GTPGIPGVPGPVGPPGEPGEEGRYKQKHQS VFTVTRQTAQYPLANNLVKFNTVITNPQGD YDTSTGKFTCKVPGLYYFVYHTSLTSNLCV HLYRSGTRVTTFCDHMSNSKQVSSGGVLLR LQMGEQVWLAVNDYNGMVGTEGSDSVFSGF LLFPD | 18 |
| Zebrafish (Danio rerio) | A | ACN62221 | MQPSAFFAFLWAGALFPFSFCQDECVKHGR NGADGPNGRDGLPGPKGEKGEPALQVKLSS IALEELKGDMGVRGPPGEPGLEGLMGAIGP RGPLGPAGPRGSSVGADGAKASEKPAFSVL RNEASQAQYKQPVTFNDKLSDANDDFQIKT GYFTCKVPGVYYFVFHASSEGRLCLRLKST SAPPVSLSFCDFNSKSVSLVVSGGAVLTLL KGDKVWIEPFAGDGGVGQMPKRLYAVFNGF LIYRNAE | 19 |
| | B | ACN62222 | MLFALMSAHVVPQLAIMLLLVTSSMSETCA GNKGFPGTPGIPGVPGTDGKDGAKGEKGDP GENEVQMTGPKGDPGKPGLPGRPGVKGPEG PQGPPGPPGPKGQRGVLSGKVAPDQYFVFS YKKSQKLEKILQDKLVVFDVPLITGIDGVL DGEGYFDVTITGMYYISYQISFQQSACLKI QIGAEEKVKFCDSPKLILGTAASVVLKLNK GDKVSVQSTGESTVFSRDTDCTFTGFMLFP IK | 20 |
| | C | ACN62223 | MFGGHLILVSLLSASLCLCLASADTCPAGA MPGLPGIPGFPGRDGRQGMKGEKGDLGIPI KPGDTVKKGERGAFGLKGPPGKRGPHGDPG IMGPPGPPGEPGEAGLVDVSGSQLQSAFSV SRHTRIPPDANKVIRFSKVITNPQGHFSTD ESKFVCKIPGTYYFVLHASSHDKKLCVILV HDDKNLVSFCDHTQRGSQQVSSGGLSLYLK ENEKVWLMTNALNGMYATADRADSVFSGFL IHAH | 21 |

In some aspects of the preceding methods, the at least one peptide fragment of the protein C1q comprises at least 3, at least 4, at least 5, at least 6, at least 7, at least 8, at least 9, at least 10 or at least 20 amino acids.

In some aspects of the preceding methods, the at least one peptide fragment of the protein C1q comprises a peptide selected from Table 2. In other aspects, the at least one peptide fragment comprises a tryptic peptide of the protein C1q.

TABLE 2

C1q peptide sequences

| Peptide Sequence | Subunit of C1q | SEQ ID NO |
|---|---|---|
| VGYPGPSGPLGAR | A | 22 |
| DQPRPAFSAIR* | A | 23 |
| NPPMGGNVVIFDTVITNQEEPYQNHSGR | A | 24 |
| FVCTVPGYYYFTFQVLSQWEICLSIVSSSR | A | 25 |
| SLGFCDTTNK* | A | 26 |
| GLFVVSGGMVLQLQQGDQVWVEKDPK | A | 27 |

TABLE 2-continued

C1q peptide sequences

| Peptide Sequence | Subunit of C1q | SEQ ID NO |
|---|---|---|
| GHIYQGSEADSVFSGFLIFPSA | A | 28 |
| IAFSATR* | B | 29 |
| TINVPLRR | B | 30 |
| FDHVITNMNNNYEPR* | B | 31 |
| VPGLYYFTYHASSR* | B | 32 |
| GNLCVNLMR | B | 33 |
| LEQGENVFLQATDK* | B | 34 |
| FQSVFTVTR | C | 35 |
| QTHQPPAPNSLIR* | C | 36 |
| FNAVLTNPQGDYDTSTGK* | C | 37 |
| VPGLYYFVYHASHTANLCVLLYR* | C | 38 |

TABLE 2-continued

C1q peptide sequences

| Peptide Sequence | Subunit of C1q | SEQ ID NO |
|---|---|---|
| VVTFCGHTSK | C | 39 |
| TNQVNSGGVLLR | C | 40 |

*denotes human/monkey C1q common peptide.

In some aspects of the preceding methods, the at least one peptide fragment of the protein C1q comprises SLGFCDTTNK (SEQ ID NO: 26), IAFSATR (SEQ ID NO: 29) or QTHQPPAPNSLIR (SEQ ID NO: 36). In other aspects, the at least one peptide fragment comprises at least two of SLGFCDTTNK (SEQ ID NO: 26), IAFSATR (SEQ ID NO: 29) or QTHQPPAPNSLIR (SEQ ID NO: 36). In still other aspects, the at least one peptide fragment comprises each of SLGFCDTTNK (SEQ ID NO: 26), IAFSATR (SEQ ID NO: 29) and QTHQPPAPNSLIR (SEQ ID NO: 36).

Thus, the present disclosure encompasses a method comprising an assay comprising: (1) contacting a biological sample with at least one proteolytic enzyme to produce at least one peptide fragment of the protein C1q present in the biological sample, wherein the at least one peptide fragment comprises each of SLGFCDTTNK (SEQ ID NO: 26), IAFSATR (SEQ ID NO: 29) and QTHQPPAPNSLIR (SEQ ID NO: 36); (2) performing SRM-MS to generate a signal corresponding to the at least one C1q peptide fragment, wherein the SRM-MS signals are according to transition ion pairs comprising each of precursor SLGFCDTTNK (SEQ ID NO: 26) transition pair 571.8-942.3, precursor IAFSATR (SEQ ID NO: 29) transition pair 383.1-581.1, and precursor QTHQPPAPNSLIR (SEQ ID NO: 36) transition pair 487.0-350.3; and (3) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises each of SLGFCDTTNK (SEQ ID NO: 26), IAFSATR (SEQ ID NO: 29) and QTHQPPAPNSLIR (SEQ ID NO: 36); (2) adding to the biological sample at least one labeled, synthetic peptide fragment comprising an amino acid sequence identical to the amino acid sequence of each of SLGFCDTTNK (SEQ ID NO: 26), IAFSATR (SEQ ID NO: 29) and QTHQPPAPNSLIR (SEQ ID NO: 36); (3) performing SRM-MS to generate a signal corresponding to the at least one C1q peptide fragment, wherein the SRM-MS signals are according to transition ion pairs comprising each of precursor SLGFCDTTNK (SEQ ID NO: 26) transition pair 571.8-942.3, precursor IAFSATR (SEQ ID NO: 29) transition pair 383.1-581.1, and precursor QTHQPPAPNSLIR (SEQ ID NO: 36) transition pair 487.0-350.3, and a signal corresponding to the at least one labeled, synthetic peptide; and (4) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises SLGFCDTTNK (SEQ ID NO: 26); (2) performing selected reaction monitoring mass spectrometry (SRM-MS) to generate a signal corresponding to the at least one C1q peptide fragment, wherein the SRM-MS signals are according to transition ion pairs comprising precursor SLGFC(Cam)DTTNK (SEQ ID NO: 41) transition pair 571.8-942.3; and (3) determining the abundance of the at least one C1q peptide fragment by comparing the normalized signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises SLGFCDTTNK (SEQ ID NO: 26); (2) adding to the biological sample at least one labeled, synthetic peptide fragment comprising an amino acid sequence identical to the amino acid sequence of SLGFCDTTNK (SEQ ID NO: 26); (3) performing selected reaction monitoring mass spectrometry (SRM-MS) to generate a signal corresponding to the at least one C1q peptide fragment, wherein the SRM-MS signals are according to transition ion pairs comprising precursor SLGFC(Cam)DTTNK (SEQ ID NO: 41) transition pair 571.8-942.3, and a signal corresponding to the at least one labeled, synthetic peptide; and (4) determining the abundance of the at least one C1q peptide fragment by comparing the normalized signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprising IAFSATR (SEQ ID NO: 29); (2) performing selected reaction monitoring mass spectrometry (SRM-MS) to generate a signal corresponding to the at least one C1q peptide fragment, wherein the SRM-MS signals are according to transition ion pairs comprising precursor IAFSATR (SEQ ID NO: 29) transition pair 383.1-581.1; and (3) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprising IAFSATR (SEQ ID NO: 29); (2) adding to the biological sample at least one labeled, synthetic peptide fragment comprising an amino acid sequence identical to the amino acid sequence of IAFSATR (SEQ ID NO: 29); (3) performing selected reaction monitoring mass spectrometry (SRM-MS) to generate a signal corresponding to the at least one C1q peptide fragment, wherein the SRM-MS signals are according to transition ion pairs comprising precursor IAFSATR (SEQ ID NO: 29) transition pair 383.1-581.1, and a signal corresponding to the at least one labeled, synthetic peptide; and (4) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises QTHQPPAPNSLIR (SEQ ID NO: 36); (2) performing selected reaction monitoring mass spectrometry (SRM-MS) to generate a signal corresponding to the at least one C1q peptide fragment, wherein the SRM-MS signals are according to transition ion pairs comprising precursor QTHQPPAPNSLIR (SEQ ID NO: 36) transition pair 487.0-350.3; and (3) determining the abundance of the at least one C1q peptide fragment by comparing the signal to a standard curve, wherein the abundance of the at least C1q peptide fragment determines the concentration of C1q in the biological sample.

The present disclosure also encompasses a method comprising an assay comprising: (1) contacting a biological sample with at least one proteolytic enzyme to produce at least one peptide fragment of the protein C1q present in the biological sample, wherein the at least one peptide fragment comprises QTHQPPAPNSLIR (SEQ ID NO: 36); (2) adding to the biological sample at least one labeled, synthetic peptide fragment comprising an amino acid sequence identical to the amino acid sequence of QTHQPPAPNSLIR (SEQ ID NO: 36); (3) performing selected reaction monitoring mass spectrometry (SRM-MS) to generate a signal corresponding to the at least one C1q peptide fragment, wherein the SRM-MS signals are according to transition ion pairs comprising precursor QTHQPPAPNSLIR (SEQ ID NO: 36) transition pair 487.0-350.3, and a signal corresponding to the at least one labeled, synthetic peptide; and (4) determining the abundance of the at least one C1q peptide fragment by comparing the signal to a standard curve, wherein the abundance of the at least C1q peptide fragment determines the concentration of C1q in the biological sample.

In some aspects of the methods of the present disclosure, the selected reaction monitoring mass spectrometry is LC-SRM-MS/MS.

In some aspects of the methods of the present disclosure, the at least one proteolytic enzyme is trypsin. Other suitable proteolytic enzymes will be known to those of skill in the art, including, but not limited to Glu-C protease, Lys-N protease, Lys-C protease, Asp-N protease or chymotrypsin.

In some aspects of the methods of the present disclosure, a standard curve can be produced using a method comprising: (a) preparing at least two C1q concentration standards by mixing known quantities of purified C1q protein and C1q-depleted serum; (b) adding to the at least two C1q concentration standards at least one labeled, synthetic peptide fragment with an amino acid sequence identical to an at least one peptide fragment of C1q that is expected to be produced following contacting the C1q concentration standard with a proteolytic enzyme; (c) contacting the at least two labeled C1q concentration standards with a proteolytic enzyme to produce at least one peptide fragment of C1q; (d) performing selected reaction monitoring mass spectrometry to determine the strength of the signal that corresponds to the at least one peptide fragment of C1q and the strength of the signal that corresponds to the at least one labeled, synthetic peptide fragment in each of the at least two labeled C1q concentration standards; and (e) determining a standard curve using the signals and the known quantities of C1q protein.

In some aspects, a standard curve can be produced using at least three, or at least four, or at least five, or at least six, or at least seven, or at least eight, or at least nine or at least ten C1q concentration standards. In some aspects, preparing a C1q concentration standard can comprise diluting, or serially diluting, purified C1q protein in C1q-depleted serum, wherein the dilution factor can be 1:1, 1:1.5, or 1:2, or 1:2.5, or 1:3, or 1:3.5, or 1:4, or 1:5, or 1:6, or 1:7, or 1:8, or 1:9, or 1:10, or 1:100, or 1:1000, or any dilution factor within the range of 1:1 to 1:10000.

In some aspects of the methods of the present disclosure, at least one labeled, synthetic peptide fragment can be added to a biological sample prior to contacting the biological sample with a proteolytic enzyme.

In some aspects of the present disclosure, the at least one labeled, synthetic peptide fragment can be used for troubleshooting the methods of the present disclosure.

In some aspects of the present disclosure, the signal that correspond to the at least one labeled, synthetic peptide fragment can be used to normalize the signal of the at least one peptide fragment of the protein C1q to which the labeled, synthetic peptide fragment corresponds.

In some aspects of the methods of the present disclosure, a C1q standard curve can be used to measure the C1q abundance in biological samples. The abundance of the C1q peptides in predetermined, standard samples can be defined and the results compared to the LC-SRM-MS results from a corresponding C1q peptide found in a biological sample. This allows for the calculation of the abundance of the peptide in the biological sample. Thus, by knowing the abundance of a peptide in a sample, the abundance of the protein it corresponds to is determined.

Compositions of the Present Disclosure

Various compositions of the present disclosure are described in full detail herein.

The present disclosure provides a composition comprising at least one isolated synthetic peptide, said composition comprising at least one isolated synthetic peptide with an amino acid sequence selected from the protein C1q.

Synthetic peptides can be generated using any method known in the art. These methods can include recombinant expression techniques such as expression in bacteria or in vitro expression in eukaryotic cell lysate. These methods can also include solid phase synthesis.

The synthetic peptides can be isotopically labeled. The isotopes with which they can be labeled include $^{13}C$, $^{2}H$, $^{15}N$ and $^{18}O$. A labeled peptide can comprise at least one $^{13}C$ labeled and/or $^{15}N$ labeled Lysine residue, or at least one $^{13}C$ labeled and/or $^{15}N$ labeled Arginine residue. The peptides can also include a polar solvent. Polar solvents can include water and mixtures of ethanol and water.

In some aspects of compositions of the present disclosure, the C1q protein can be human C1q protein. In other aspects, the C1q protein is *Macaca fascicularis* C1q protein. In yet another aspect, the C1q protein can be *Macaca mulatta*. The C1q protein can comprise any of the sequences show in Table 1.

In some aspects of a composition of the present disclosure, the at least one isolated synthetic peptide comprises at least 3, at least 4, at least 5, at least 6, at least 7, at least 8, at least 9, at least 10 or at least 20 amino acids.

In some aspects of a composition of the present disclosure, an isolated synthetic peptide comprises a sequence of a C1q peptide fragment generated by contacting C1q with a proteolytic enzyme. In preferred aspects, the proteolytic enzyme is trypsin. Thus, in preferred aspects, an isolated synthetic peptide is a tryptic peptide of C1q.

In some aspects of a composition of the present disclosure, an isolated synthetic peptide is labeled. The isolated synthetic peptides can be isotopically labeled. The isotopes with which they can be labeled include, but are not limited to, $^{13}C$, $^{2}H$, $^{15}N$ and $^{18}O$. The peptides can also include a polar solvent. Polar solvents can include water, mixtures of ethanol and water and acetonitrile.

In some aspects of a composition of the present disclosure, the isolated synthetic peptide comprises a peptide selected from Table 2. In other aspects, the composition comprises any two peptides described in Table 2. In other aspects, the composition included, any 3, 4, 5, 6, 7, 8, 9, 10, 11, 12, 13, 14, 15, 16, 17, 18, or 19 peptides described in Table 2.

In a preferred aspect, a composition of the present disclosure can comprise at least one isolated synthetic peptide comprising SLGFCDTTNK (SEQ ID NO: 26), IAFSATR (SEQ ID NO: 29) or QTHQPPAPNSLIR (SEQ ID NO: 36). A composition can comprise at least one isolated synthetic peptide comprising at least two of SLGFCDTTNK (SEQ ID NO: 26), IAFSATR (SEQ ID NO: 29) or QTHQPPAPNSLIR (SEQ ID NO: 36). In yet other aspects, a composition can comprise at least one isolated synthetic peptide comprising each of SLGFCDTTNK (SEQ ID NO: 26), IAFSATR (SEQ ID NO: 29) or QTHQPPAPNSLIR (SEQ ID NO: 36).

In some aspects of the compositions of the present disclosure, the cysteine in the synthetic peptide SLGFCDTTNK (SEQ ID NO: 26) can be modified. The modification can be carbamidomethylation.

The present disclosure provides a composition comprising at least one transition ion pair, said composition comprising at least one transition ion pair of the protein C1q, wherein the at least one transition ion pair consists of a precursor ion with a corresponding m/z and a fragment ion with a corresponding ion m/z.

In some aspects of compositions of the present disclosure, the C1q protein can be human C1q protein. In other aspects, the C1q protein is *Macaca fascicularis* C1q protein. In yet another aspect, the C1q protein can be *Macaca mulatta*. The C1q protein can comprise any of the sequences show in Table 1.

The present disclosure provides a composition comprising at least one transition ion pair, said composition comprising at least one transition ion pair of the protein C1q, wherein the at least one transition ion pair consists of a precursor ion with a corresponding m/z and a fragment ion with a corresponding ion m/z, and wherein the transition ion pair is selected from precursor SLGFC(Cam)DTTNK (SEQ ID NO: 41) transition pair 571.8-942.3, precursor IAFSATR (SEQ ID NO: 29) transition pair 383.1-581.1 and precursor QTHQPPAPNSLIR (SEQ ID NO: 36) transition pair 487.0-350.3.

Definitions

As used herein, "m/z" indicates the mass-to-charge ratio of an ion.

As used herein, "MS/MS" represents tandem mass spectrometry, which is a type of mass spectrometry involving multiple stages of mass analysis with some form of fragmentation occurring in between the stages.

As used herein, "LC-SRM-MS" is an acronym for "selected reaction monitoring" and may be used interchangeably with "LC-MRM-MS" or "LC-SRM-MS/MS".

LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadrupoles are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio in LC-SRM-MS is often superior to conventional tandem mass spectrometry (MS/MS) experiments that do not selectively target (filter) particular analytes but rather aim to survey all analytes in the sample.

LC-SRM-MS mass spectrometry involves the fragmentation of gas phase ions and occurs between the different stages of mass analysis. There are many methods used to fragment the ions and these can result in different types of fragmentation and thus different information about the structure and composition of the molecule. The transition ions observed in an LC-SRM-MS spectrum result from several different factors, which include, but are not limited to, the primary sequence, the amount of internal energy, the means of introducing the energy, and charge state. Transitions must carry at least one charge to be detected. An ion is categorized as either a, b or c if the charge is on a transition comprising the original N terminus of the peptide, whereas the ion is categorized as either x, y or z if the charge is on a transition comprising the original C terminus of the peptide. A subscript indicates the position of residues in the transition (e.g., first peptide residue in $x_1$ from C terminus, second peptide residues in $y_2$ from C terminus, and third peptide residues in $z_3$ from C terminus, etc.).

In a generic peptide repeat unit represented —N—C(O)—C—, an x ion and an a ion resulting from cleavage of the carbonyl-carbon bond (i.e., C(O)—C). The x ion is an acylium ion, and the a ion is an iminium ion. A y ion and a b ion result from cleavage of the carbonyl-nitrogen bond (i.e., C(O)—N, also known as the amide bond). In this case, the y ion is an ammonium ion and the b ion is an acylium ion. Finally, a z ion and a c ion result from cleavage of the nitrogen-carbon (i.e., C—N) bond. The z ion is a carbocation and the c ion is an ammonium ion.

Superscripts are sometimes used to indicate neutral losses in addition to the backbone fragmentation, for example, * for loss of ammonia and ° for loss of water. In addition to protons, c ions and y ions may abstract an additional proton from the precursor peptide. In electrospray ionization, tryptic peptides may carry more than one charge.

Internal transitions arise from double backbone cleavage. These may be formed by a combination of b-type and y-type cleavage (i.e., cleavage producing b and y ions). Internal cleavage ions may also be formed by a combination of a-type and y-type cleavage. An internal transition with a single side chain formed by a combination of a-type and y-type cleavage is called an iminium ion (sometimes also referred to as an imonium or immonium ion). These ions are labeled with the one letter code for the corresponding amino acid.

Low energy CID (i.e., collision induced dissociation in a triple quadrupole or an ion trap) involves the fragmentation of a peptide carrying a positive charge, primarily along its backbone, to generate primarily a, b and y ions.

One or more liquid chromatography (LC) purification steps are performed prior to a subsequent LC-SRM-MS analysis step. Traditional LC analysis relies on the chemical interactions between sample components and column packing materials, where laminar flow of the sample through the column is the basis for separation of the analyte of interest from the test sample. The skilled artisan will understand that separation in such columns is a diffusional process. A variety of column packing materials are available for chromatographic separation of samples, and selection of an appropriate separation protocol is an empirical process that depends on the sample characteristics, the analyte of interest, the interfering substances present and their characteristics, etc. Various packing chemistries can be used depending on the needs (e.g., structure, polarity, and solubility of compounds being purified). In various aspects the columns are polar, ion exchange (both cation and anion), hydrophobic interaction, phenyl, C-2, C-8, C-18 columns, polar coating on porous polymer, or others that are commercially available. During chromatography, the separation of materials is affected by variables such as choice of eluent (also known as a "mobile phase"), choice of gradient elution and the gradient conditions, temperature, etc. In certain aspects, an analyte may be purified by applying a sample to a column under conditions where the analyte of interest is reversibly retained by the column packing material, while one or more other materials are not retained. In these aspects, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample.

The following parameters are used to specify an LC-SRM-MS assay of a protein under a particular LC-SRM-MS system: (1) a tryptic peptide of the protein; (2) the retention time (RT) of the peptide; (3) the m/z value of the peptide precursor ion; (4) the declustering potential used to ionize the precursor ion; (5) the m/z value of a fragment ion generated from the peptide precursor ion; and (6) the collision energy (CE) used to fragment the peptide precursor ion that is optimized for the particular peptide.

As used herein, "ISP" refers to "internal standard peptides".

To facilitate accurate quantification of the peptide transitions by the methods disclosed herein, a set of isotopically-labeled synthetic versions of the peptides of interest may be added in known amounts to the sample for use as internal standards. Since the isotopically-labeled peptides have physical and chemical properties identical to the corresponding surrogate peptide, they co-elute from the chromatographic column and are easily identifiable on the resultant mass spectrum. The addition of the labeled standards may occur before or after proteolytic digestion. Methods of synthesizing isotopically-labeled peptides will be known to those of skill in the art. Thus, in some aspects, the experimental samples contain internal standard peptides. Other aspects may utilize external standards or other expedients for peptide quantification.

As used herein, a "tryptic peptide" refers to the peptide that is formed by the treatment of a protein with trypsin.

As used herein, the term "standard curve" may be used interchangeably with the term "calibration curve".

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present disclosure, the preferred materials and methods are described herein. It is to be understood that the terminology used herein is for the purpose of describing particular aspects only, and is not intended to be limiting.

EXAMPLES

Example 1—Determining a C1q Concentration Standard Curve Using the Methods of the Present Disclosure The methods of the present disclosure were used to generate standard curves, also referred to as a calibration curves, using a set of C1q reference solutions of known C1q concentrations, including C1q standard and quality control (QC) samples. The sensitivity and accuracy of the methods of the present disclosure were also tested.

The calibration curves were generated using C1q standard samples that were prepared and applied using the following guidelines:

Purified C1q protein was diluted in the same biological matrix as experimental samples, The set of C1Q reference solutions tested consisted of a double blank, a blank, and at least 6 non-zero concentrations of C1q;

The lower limit of quantitation (LLOQ) is defined the concentration of C1q protein at which the measured response of the LLOQ sample is at least 5 times compared to the response of the blank sample, such that the accuracy is within 25% of the nominal concentration and the coefficient of variation is less than 25%;

The upper limit of quantitation (ULOQ) is defined such that the accuracy is within 20% of the nominal concentration, and the coefficient of variation is less than 20%.

The calibration curves were generated using C1q QC samples that were prepared and applied using the following guidelines:

At least 3 concentrations of QC samples were prepared and used for calibration;

Each QC sample was prepared in duplicate;

The QC samples covered the low, medium and high quantitation range of the assay, and the low QC (LQC) sample was within 3 times the concentration of LLOQ;

The accuracy of at least 67% of QC samples was within 20% of nominal concentration;

The accuracy of at least 50% of QC samples at each level was within 20% of nominal concentration;

The minimum number of QC samples was equal to the greater of at least 5% of the number of unknown samples or 6 total QC samples;

The QC samples were prepared with a C1q stock solution that was separate from the stock solution for the preparation of C1q reference solutions.

Materials:

Purified Human Complement Protein C1q (Quidel, Item #A400)

Complement C1q-Depleted Serum, Human (Sigma-Aldrich, Cat #234401-1ML)

SLGFC(Cam)DTTNK (SEQ ID NO: 41) (New England Peptide)

IAFSATR (SEQ ID NO: 29) (New England Peptide)

QTHQPPAPNSLIR (SEQ ID NO: 36) (New England Peptide)

Bispecific monoclonal antibody drug candidate

Sequencing grade modified trypsin supplied with resuspension buffer (Promega, Cat #. V5117)

UltraPure 1.0 M Tris-HCl pH 7.5 (Invitrogen, Cat #15567-027)

UltraPure 1.0 M Tris-HCl pH 8.0 (Invitrogen, Cat #15568-025)

UltraPure 1.0 M Tris-HCl pH 8.5 (Alfa Aesar, Cat #J61038)

Urea (Sigma Aldrich, Cat #U5128-100G)

TCEP HCL (Thermo Scientific; Cat #20491)

Iodoacetamide (Sigma-Aldrich; Cat #A3221-10VL)

Formic acid (Thermo Scientific; Cat #28905)

Acetonitrile (Fisher Chemical, Cat #A955-4)

ACQUITY UPLC BEH130 C18 column, 1.7 μm, 2.1 mm×50 mm (Waters, Part #1860035554)

96 well plate, 0.5 mL, Polypropylene (Agilent, Part #5042-1386)

25 mL Disposable Reagent Reservoir (VistaLab, Part #3054-1004)

TripleQuad Mass Spectrometer (Agilent, Model #6495)

1290 Infinity II LC System (Agilent, Model #1290)

Sample Preparation

A 200 μg/mL C1q stock solution was prepared in C1q-deplete human serum and assay dilution buffer (ADB) containing 20 μg/mL of the bispecific monoclonal antibody drug candidate. The C1q stock solution was serially diluted 1 to 3, six times to prepare six C1q standard solutions (L6-L1). The LLOQ (lower limit of quantitation), low QC, medium QC, high QC, and ULOQ (upper limit of quantitation) samples were prepared in ADB independently from C1q stock solution. An aliquot of ADB was reserved as an L0 (blank) sample. The concentrations of the C1q standard and QC solutions are listed in Table 3.

TABLE 3

The concentrations of C1q standard and QC solutions.

| Level/QC | Concentration (μg/mL) |
|---|---|
| L1/LLOQ | 0.27 |
| L2 | 0.82 |
| L3 | 2.47 |
| L4 | 7.41 |
| L5 | 22.22 |
| L6/ULOQ | 66.67 |
| LQC | 0.78 |
| MQC | 6.25 |
| HQC | 50 |

The following isotope-labelled internal standard peptides (ISPs) were reconstituted to 6-12 mM in 30% acetonitrile in 0.1% formic acid to create isotope-labelled ISP solutions: SLGFC(Cam)DTTNK (SEQ ID NO: 41), IAFSATR (SEQ ID NO: 29), and QTHQPPAPNSLIR (SEQ ID NO: 36).

Each C1q sample was diluted by 50 times in 100 mM Tris-HCl, pH 7.5 and 20 μg/mL of the bispecific antibody. 5 μL of each diluted C1q sample was then denatured and reduced in 20 μL of 8 M urea and 10 mM tris(2-carboxyethyl)phosphine (TCEP) at 56° C. with shaking for 30 minutes. 5 μL of 50 mM iodoacetamide was then added to each sample, and the samples were then incubated in the dark at 25° C. with shaking for 30 minutes. 10 μL of the appropriate isotope-labelled ISP solution was then added to each sample. After addition of the ISPs, 100 μL of 0.01 μg/μL trypsin was also added to each sample. The samples were then incubated at 37° C. in the dark with shaking for 4 hours. 5 μL of 20% of formic acid was added to the samples to quench the tryptic digestion reaction. The samples were mixed and centrifuged at 4680 rpm for 5 minutes before being analyzed by LC-SRM-MS/MS.

LC-SIM-MS Analysis

The LC-SRM-MS analysis was performed on a TripleQuad Mass Spectrometer (Agilent, Model #6495) with a 1290 Infinity II LC system (Agilent, Model #1290). The LC gradient used is described in Table 4, wherein Buffer A consisted of 0.1% formic acid in water, and Buffer B consisted of 0.1% formic acid in acetonitrile.

TABLE 4

LC gradient

| Time (minute) | Buffer A (%) | Buffer B (%) | Flow (mL/minute) |
|---|---|---|---|
| 0.5 | 97 | 3 | 0.4 |
| 8.0 | 75 | 25 | 0.4 |
| 8.1 | 10 | 90 | 0.4 |
| 10.5 | 10 | 90 | 0.4 |
| 10.6 | 97 | 3 | 0.4 |
| 13.0 | 97 | 3 | 0.4 |

The SRM-MS analysis simultaneously monitored native C1q peptide fragments and isotope-labelled peptides in the samples. Peak areas for two transitions (native and heavy label) were collected and reported for both native and isotope-labelled C1q peptides. For each C1q standard and QC samples, the data output for C1q protein analyzed by LC-SRM-MS yielded six measurements consisting of two transition measurements (native and heavy label) from each of three selected peptides set forth in Table 5 below.

TABLE 5

The m/z transition and collision energy of C1q target peptides.

| C1q sub-unit | Peptide sequence | SEQ ID NO | m/z transition | Collision energy (V) |
|---|---|---|---|---|
| A | SLGFC(Cam)DTTNK | 41 | 571.8 > 942.3 | 18 |
| B | IAFSATR | 29 | 383.1 > 581.1 | 10 |
| C | QTHQPPAPNSLIR | 36 | 487.0 > 350.3 | 13 |

Each of the three peptides in Table 5 are from a different subunit of C1q. The peptide fragment derived from subunit B was used as the quantitation peptide (herein referred to as the subunit B peptide), and the peptide fragments derived from subunits A (herein referred to as the subunit A peptide) and C (herein referred to as the subunit C peptide) were used as confirmatory peptides. The isotope-labelled ISPs have amino acid sequences that are identical to each of the three selected peptides and are herein referred to as the isotope-labeled subunit A control peptide, the isotope-labeled subunit B control peptide, and the isotope-labeled subunit C control peptide.

Figure 2:
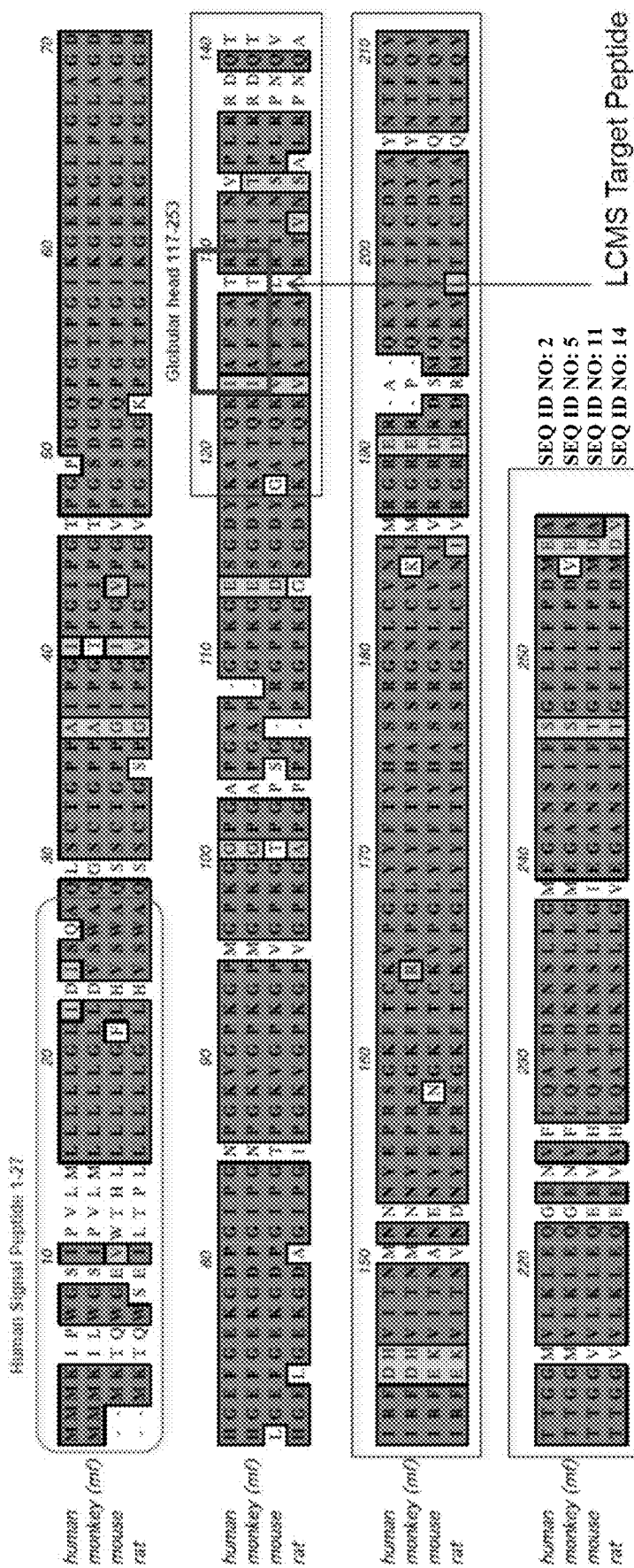
FIG. 2 is the amino acid sequence alignment of the B subunit of C1q from human, monkey, mouse and rat.
Figure 3:
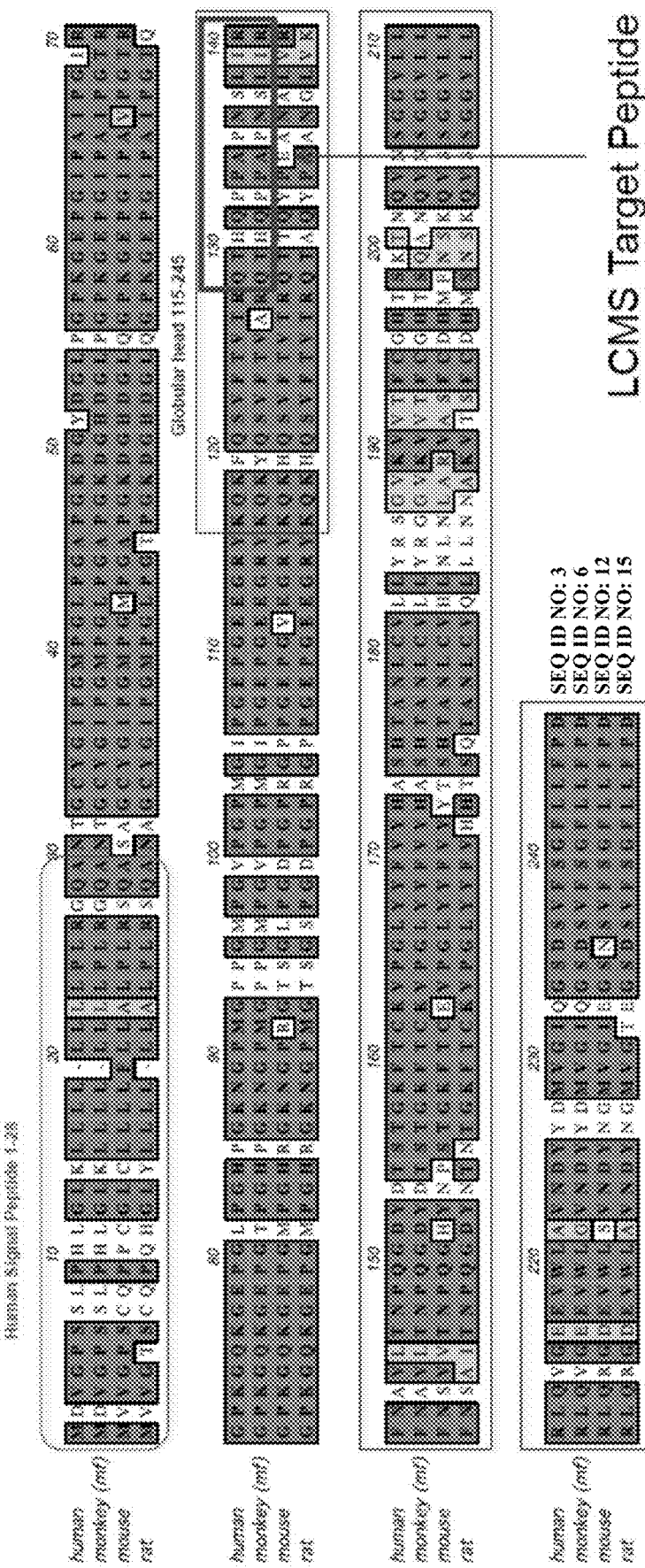
FIG. 3 is the amino acid sequence alignment of the C subunit of C1q from human, monkey, mouse and rat.

The three peptides listed in Table 5 were selected based previous results which had shown that these peptides were the best peptides for quantifying C1q concentration in a LC-SRM-MS/MS assay. The selection of these peptides was partly based on conservation of the peptide sequence between humans and monkey (*Macaca fascicularis*). FIG. 1 shows a sequence alignment of subunit A of human, monkey (*Macaca fascicularis*), mouse and rat C1q highlighting the subunit A peptide. FIG. 2 shows a sequence alignment of subunit B of human, monkey (*Macaca fascicularis*), mouse and rat C1q highlighting the subunit B peptide. FIG. 3 shows a sequence alignment of subunit C of human, monkey (*Macaca fascicularis*), mouse and rat C1q highlighting the subunit C peptide. Multiple tryptic peptides from each of the A, B and C subunits of C1q were initially tested. The tested peptides are listed in Table 2.

Results

Each C1q standard sample and each C1q QC sample were analyzed using LC-SRM-MS/MS. For each sample, 6 signals were recorded: the signal corresponding to the native subunit A peptide, the signal corresponding to the native subunit B peptide, the signal corresponding to the native subunit C peptide, the signal corresponding to the isotope-labeled subunit A control peptide, the signal corresponding to the isotope-labeled subunit B control peptide and the signal corresponding to the isotope-labeled subunit C control peptide. The data for isotope-labelled peptides were used as internal controls for assay performance troubleshooting purposes.

Figure 4:
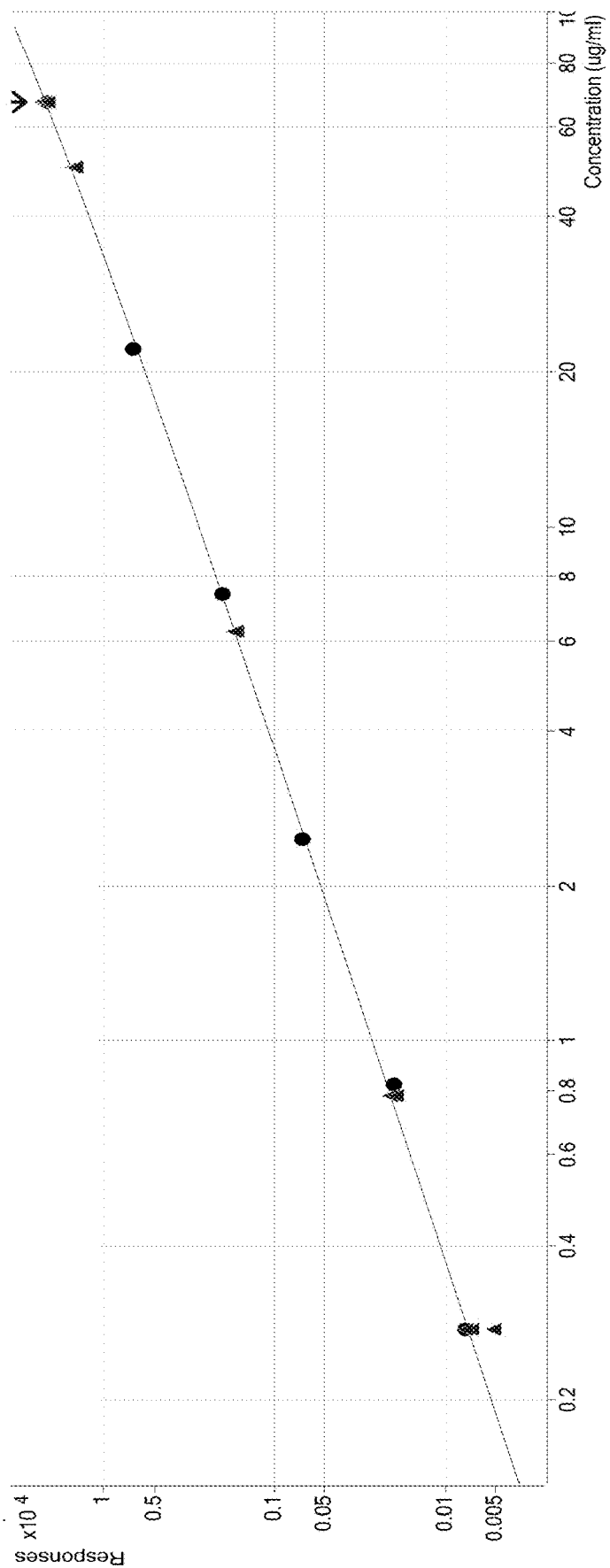
FIG. 4 is a calibration curve generated using the methods of the present disclosure and a peptide derived from the A subunit of the C1q protein.
Figure 5:
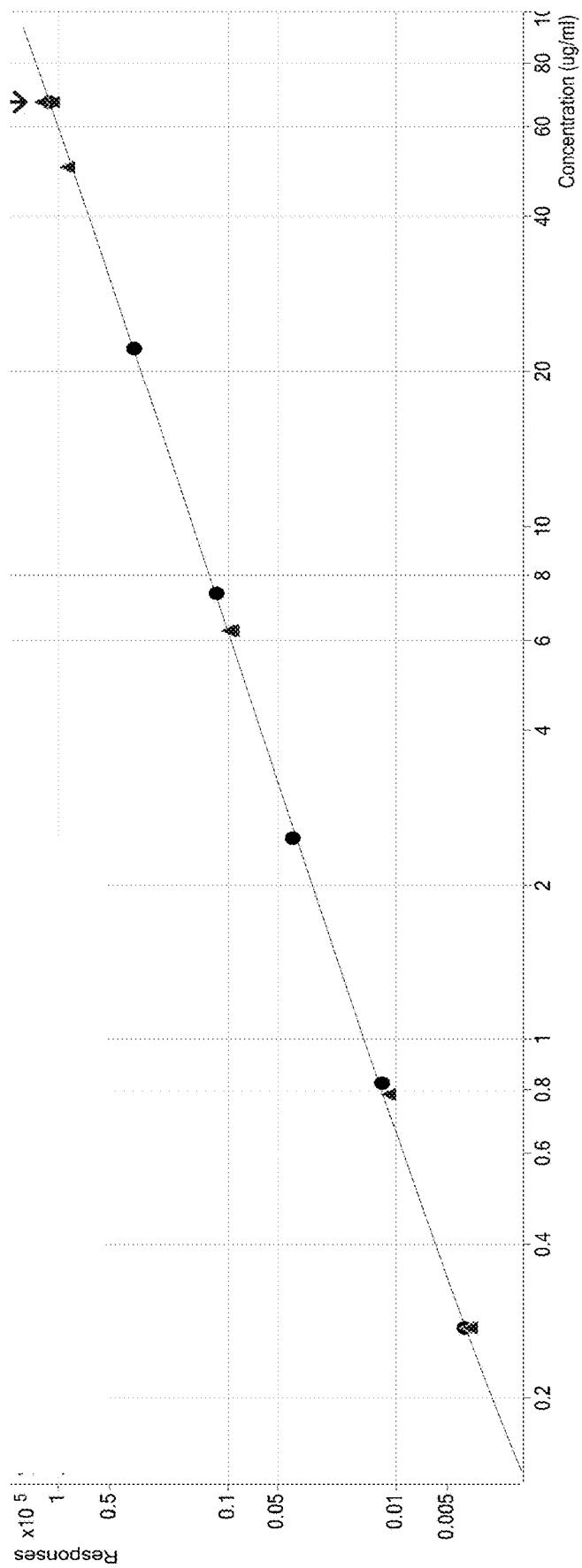
FIG. 5 is a calibration curve generated using the methods of the present disclosure and peptide derived from the B subunit of the C1q protein.
Figure 6:
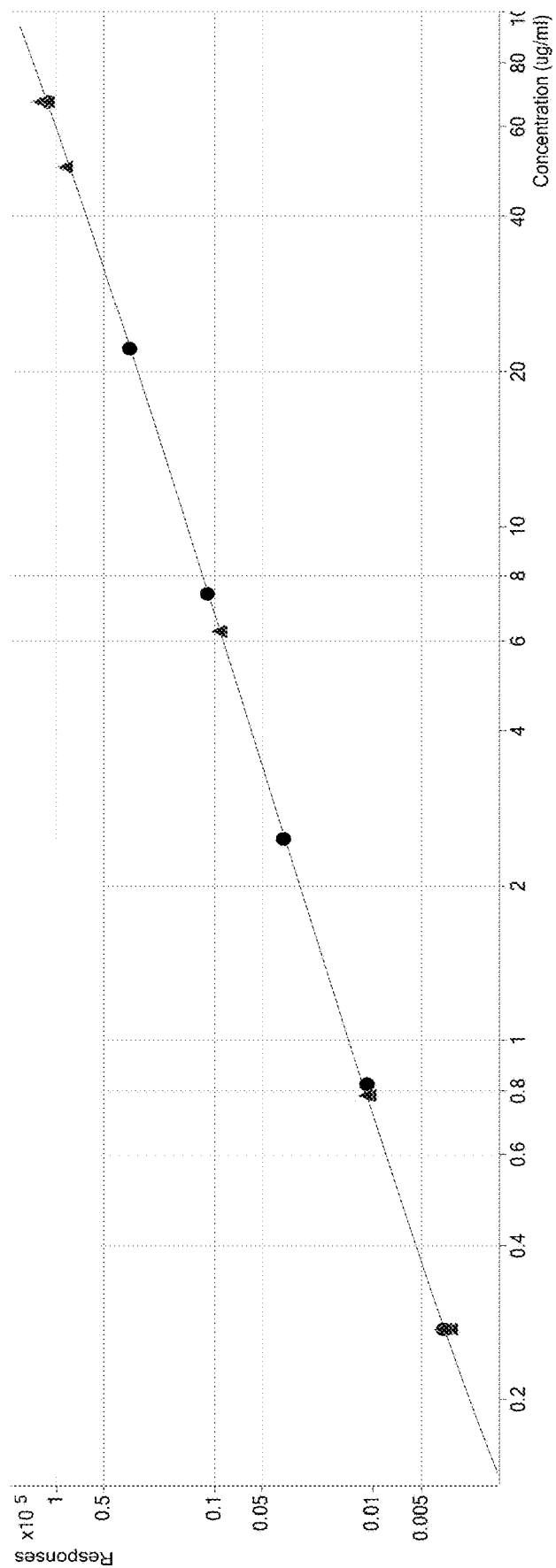
FIG. 6 is a calibration curve generated using the methods of the present disclosure and a peptide derived from the C subunit of the C1q protein.
Figure 7A:
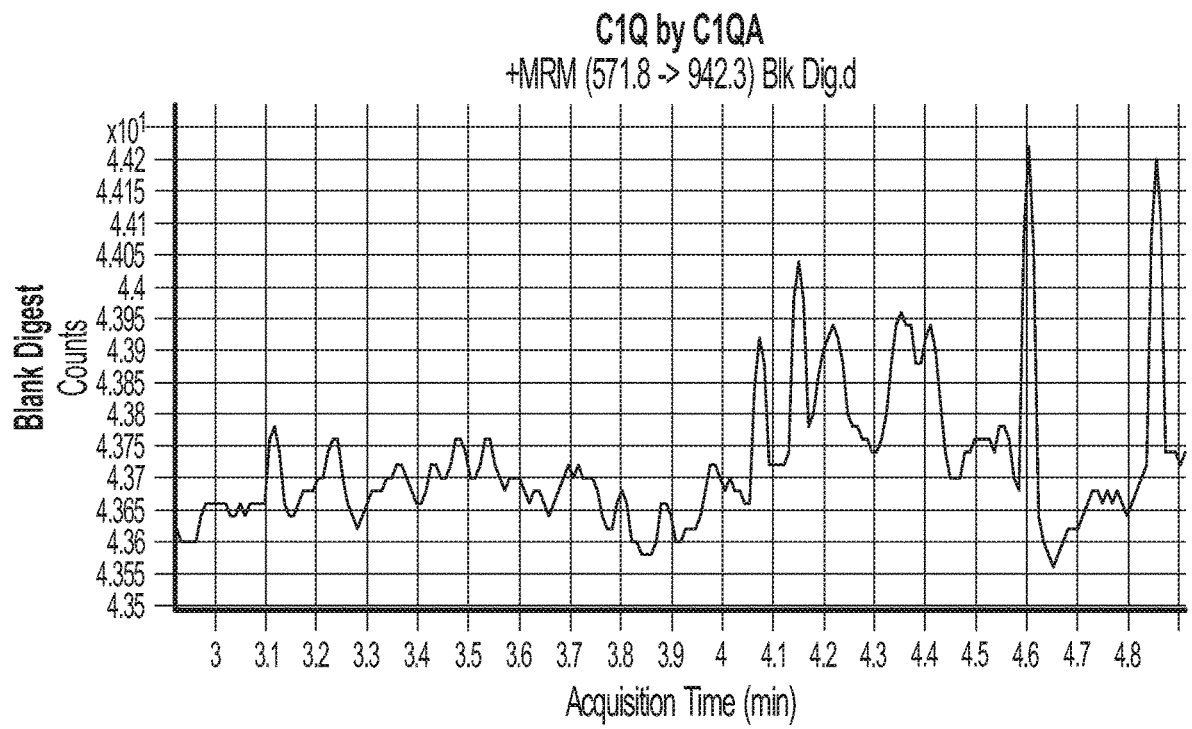
FIG. 7A, FIG. 7B, FIG. 7C, FIG. 7D, FIG. 7E and FIG. 7F are a series of LC-SRM-MS/MS chromatograms of selected peptides derived from the A, B, and C subunits of C1q in blank digest, double blank, blank, and Lower Limit of Quantitation (LLOQ) samples.
Figure 7A:
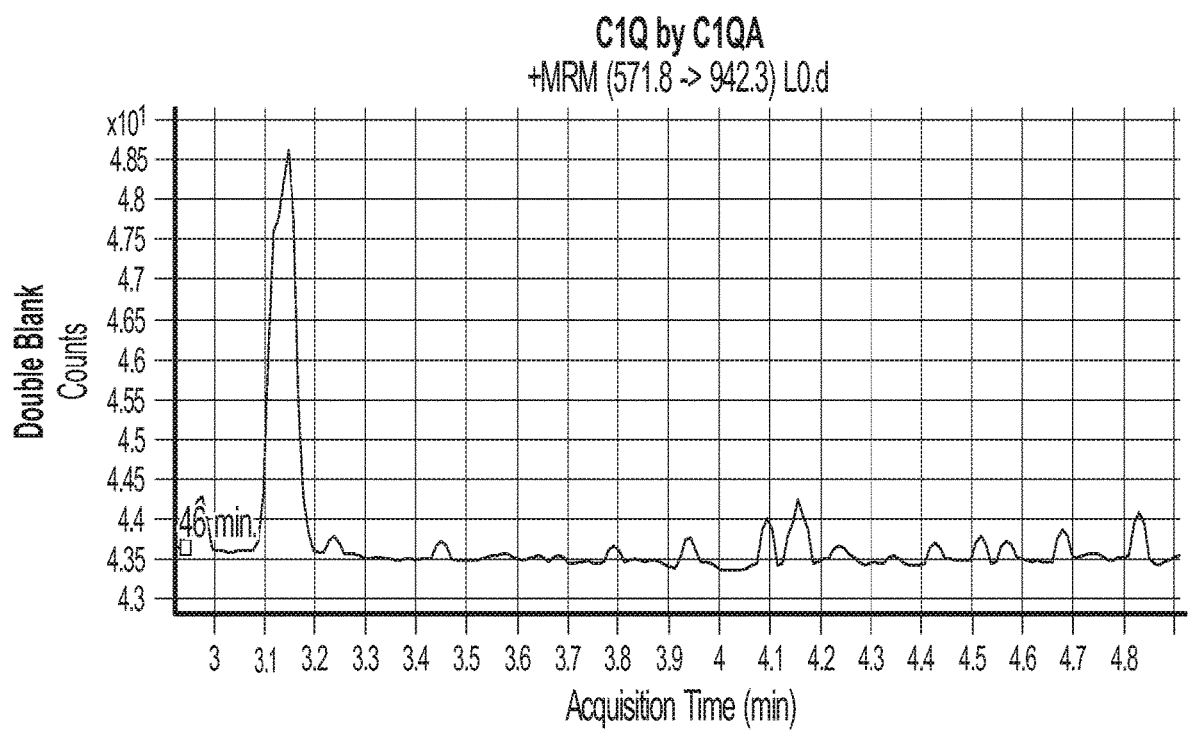
Figure 7B:
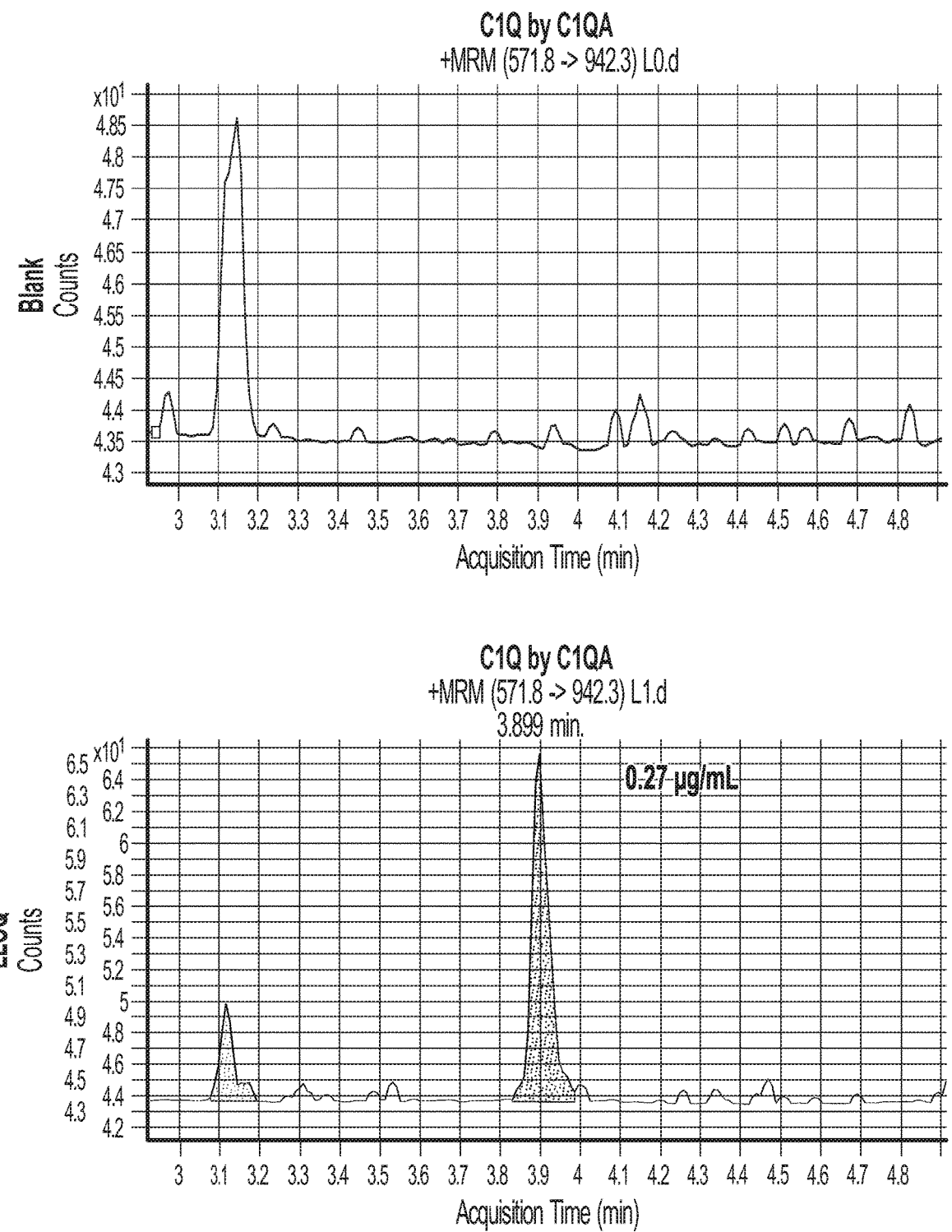
Figure 7C:
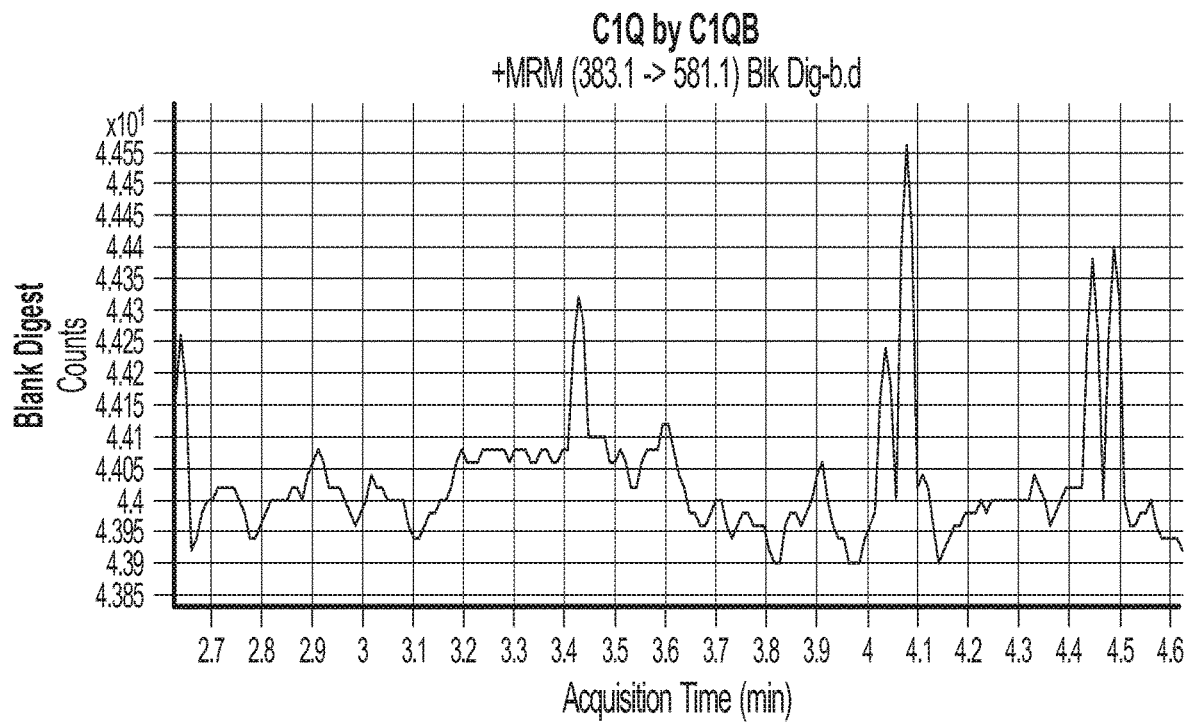
Figure 7C:
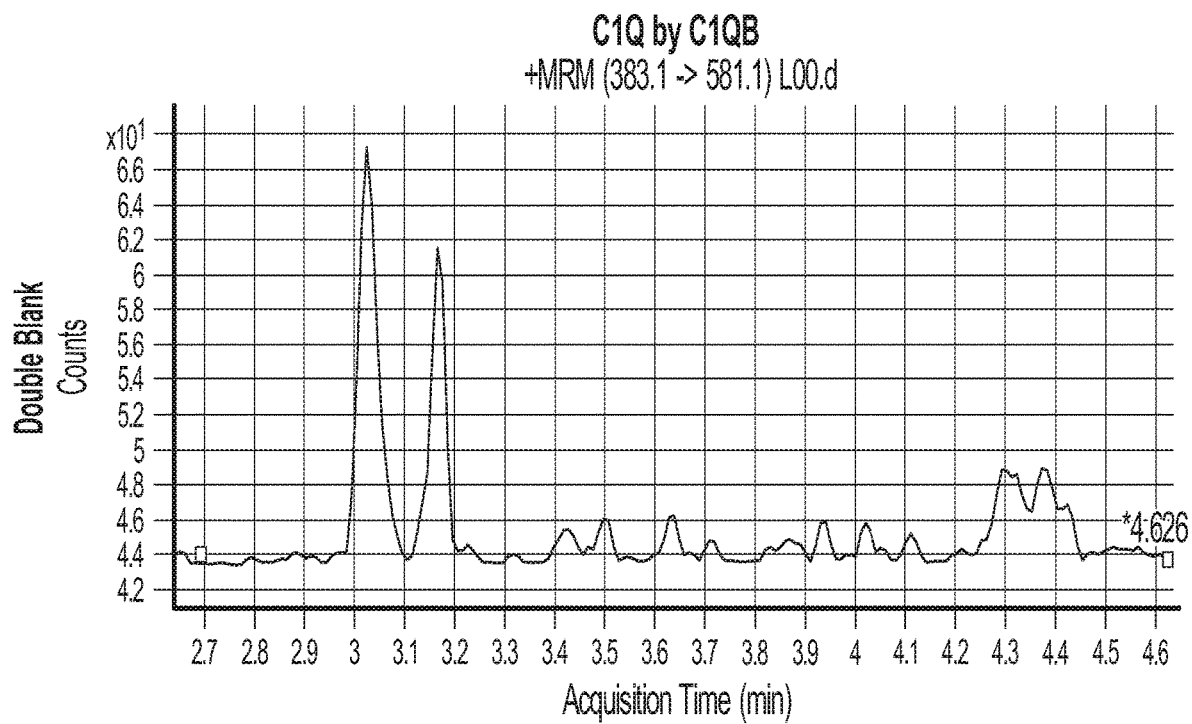
Figure 7D:
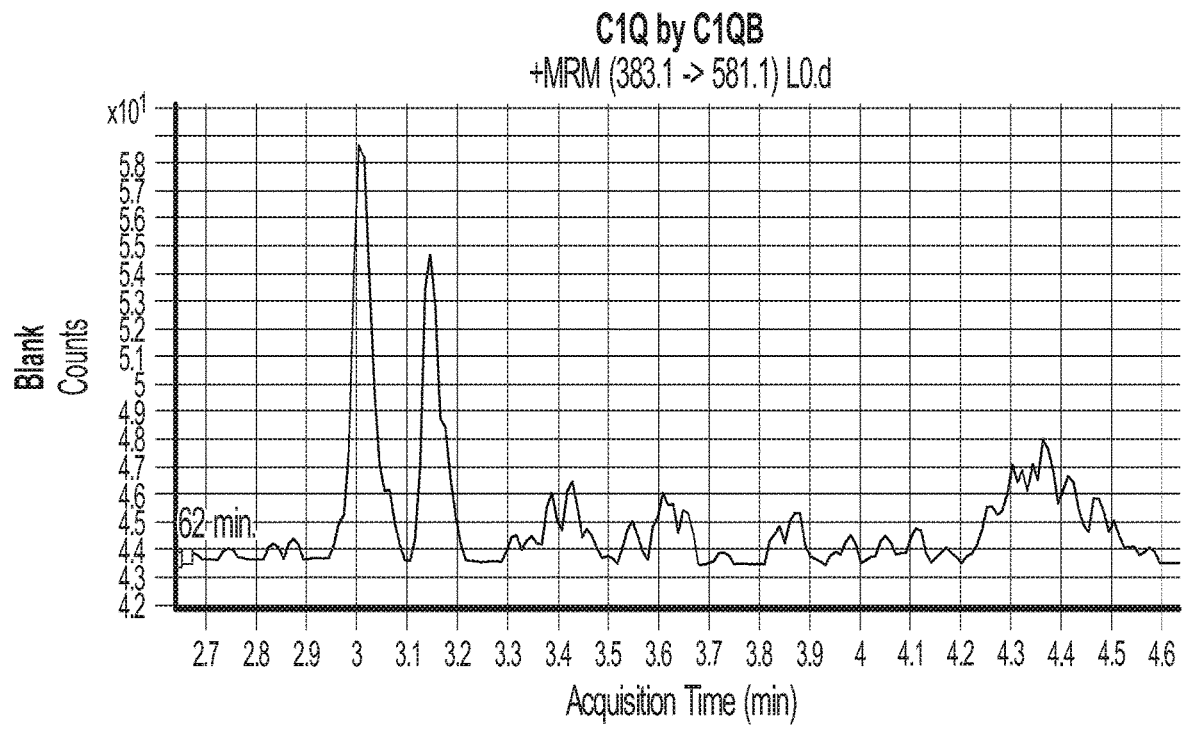
Figure 7D:
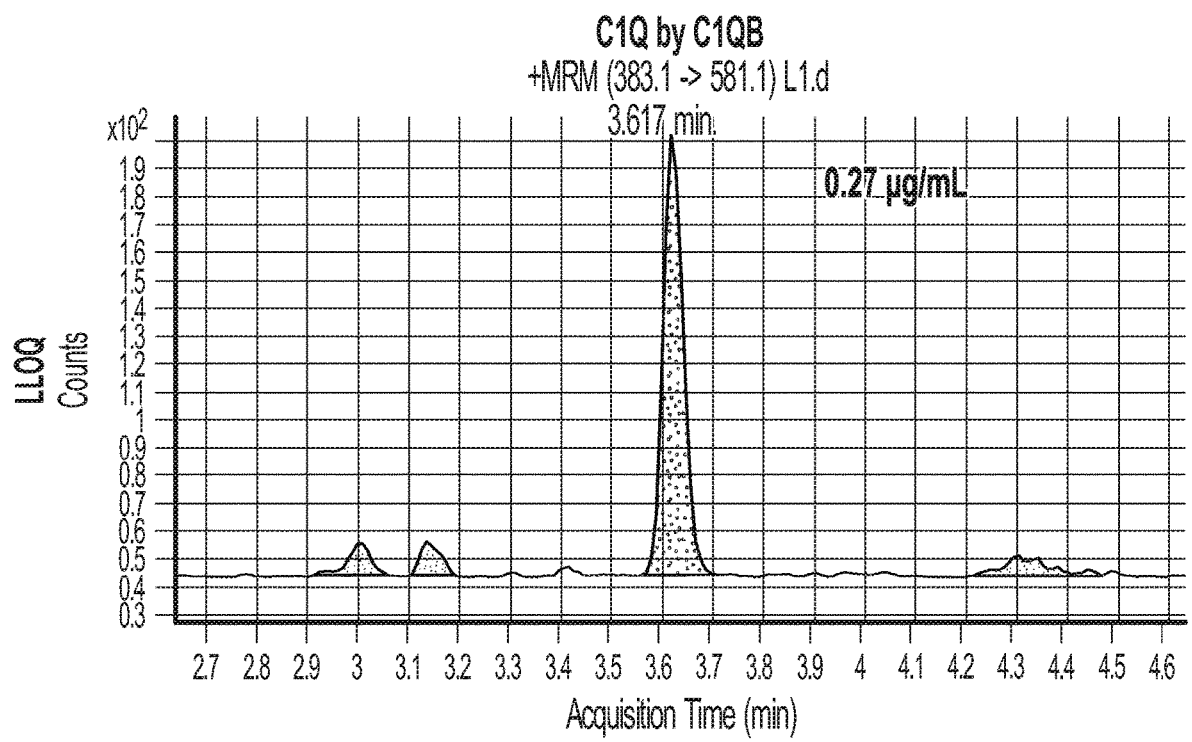
Figure 7E:
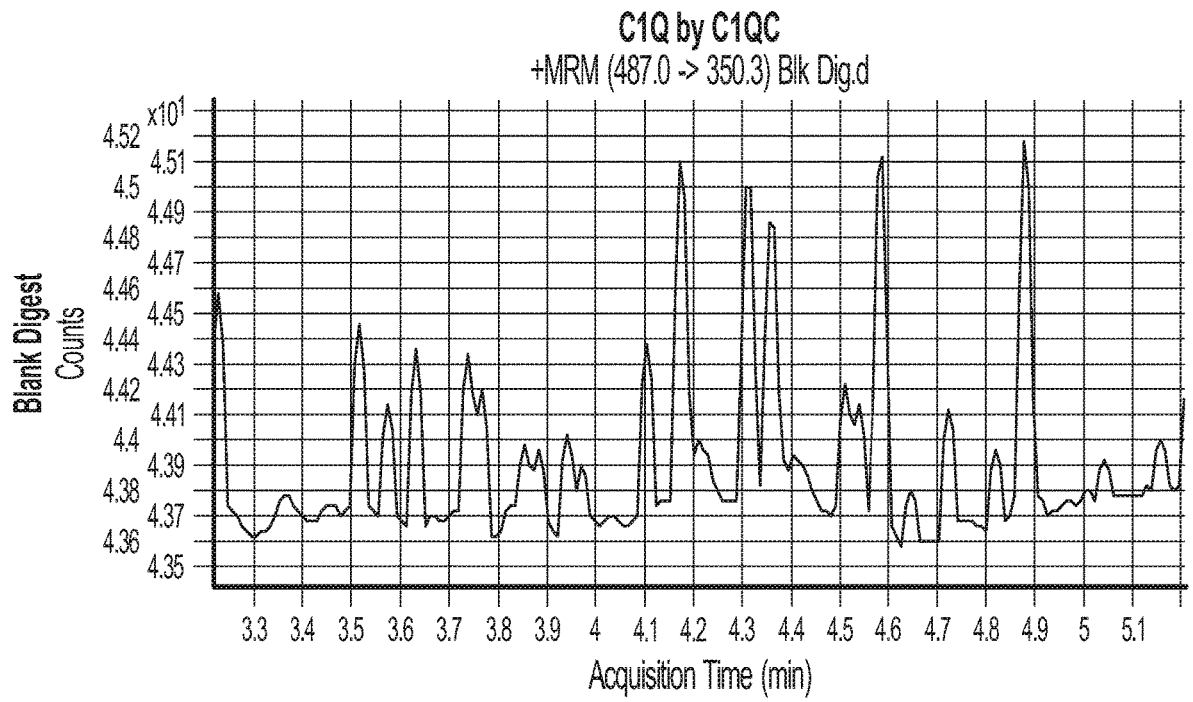
Figure 7E:
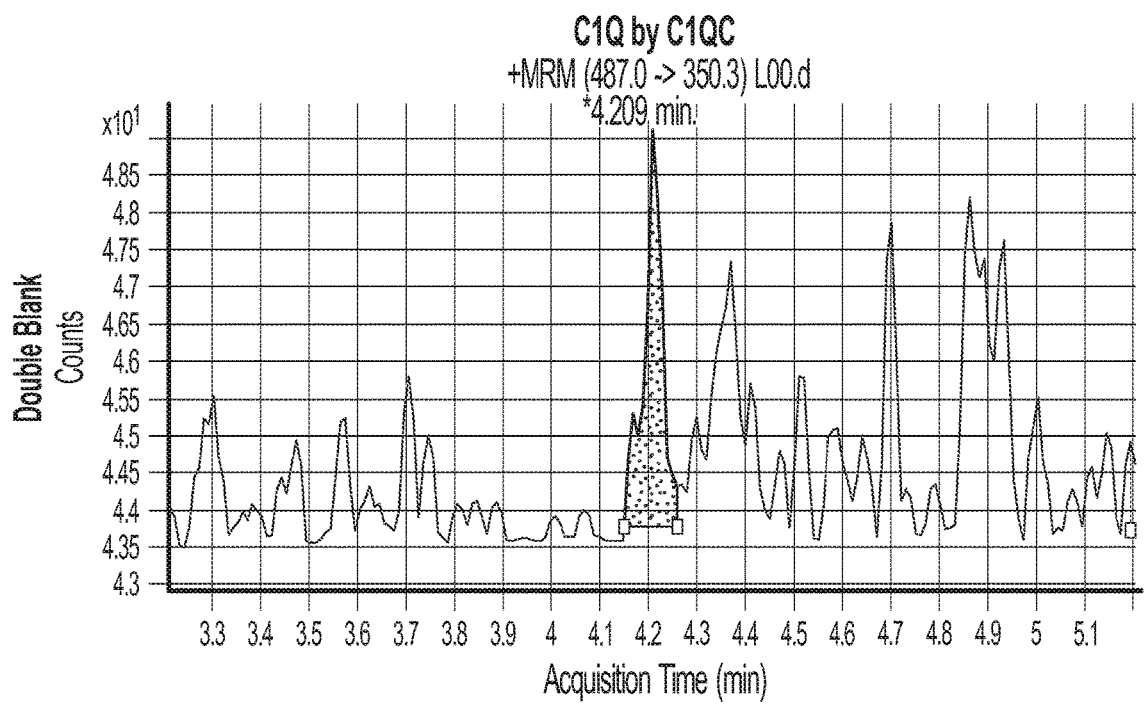
Figure 7F:
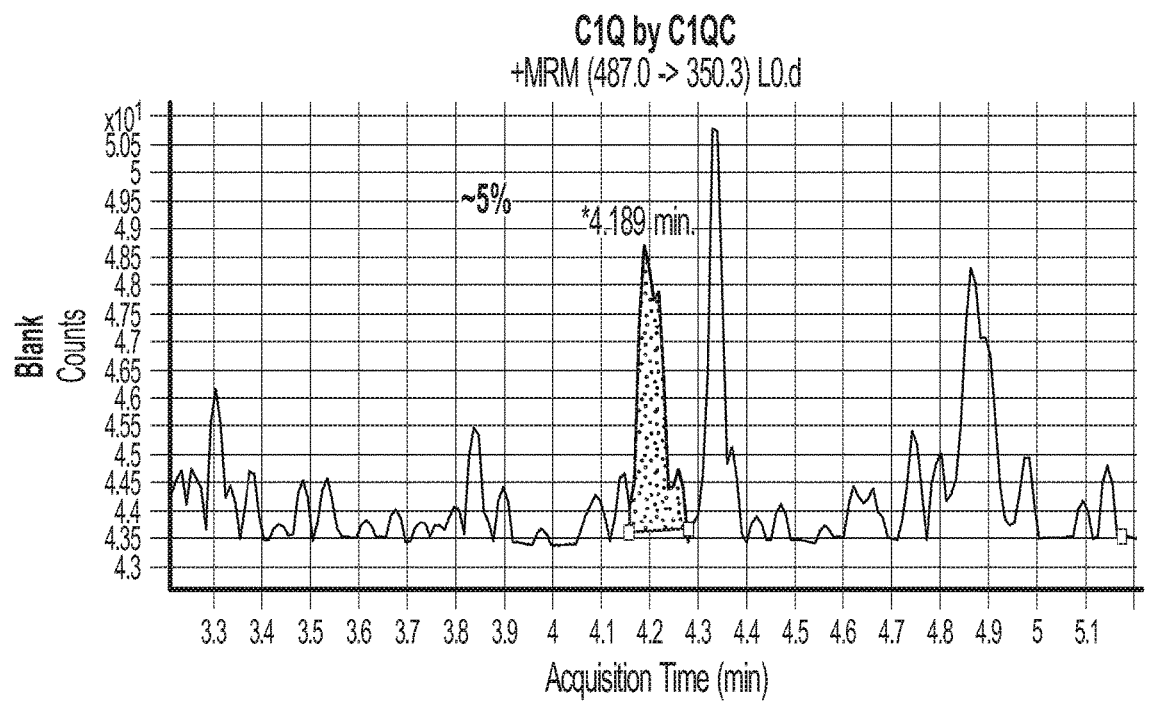
Figure 7F:
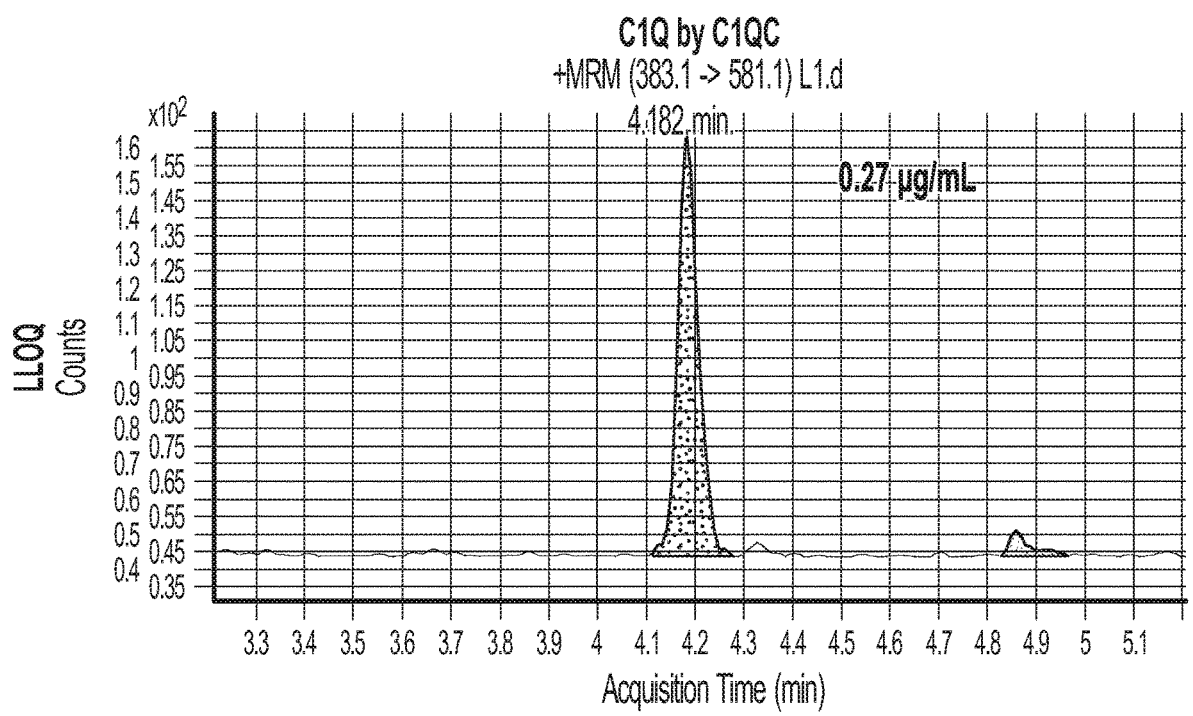

For each of the three selected peptides (the subunit A peptide, the subunit B peptide, and the subunit C peptide), a calibration curve was generated by plotting the normalized LC-SRM-MS signal recorded from C1q standard samples against the corresponding nominal concentrations of those samples. FIG. 4 shows the calibration curve generated using the signal corresponding to the subunit A peptide. FIG. 5 shows the calibration curve generated using the signal corresponding to the subunit B peptide. FIG. 6 shows the calibration curve generated using the signal corresponding to the subunit C peptide. For FIGS. 4-6, the black dots represent C1q standard samples at concentrations L1-L6. The blue triangles represent C1q QC samples at LLOQ, LQC, MQC, HQC, and ULOQ concentrations.

After generating the calibration curve, the concentrations of QC samples were then determined by comparing the LC-SRM-MS/MS signal of each of the three target peptides in the QC samples to the corresponding calibration curve. The accuracy of the assay was assessed by comparing the determined concentrations to the nominal concentrations of the QC samples. The results of the comparison is shown in Tables 6-8.

TABLE 6

Assay accuracy using target peptide SLGFC(Cam)DTTNK (SEQ ID NO: 41) derived from C1q A subunit.

| Standards | L1 | L2 | L3 | L4 | L5 | L6 |
|---|---|---|---|---|---|---|
| Nominal Conc. (μg/mL) | 0.27 | 0.82 | 2.47 | 7.41 | 22.22 | 66.67 |
| Accuracy (%) | 103 | 91 | 104 | 100 | 104 | 99 |

| QC (N = 3) | | LLOQ | LQC | MQC | HQC | ULOQ |
|---|---|---|---|---|---|---|
| Nominal Conc. (μg/mL) | | 0.27 | 0.78 | 6.25 | 50 | 66.67 |
| Accuracy (%) - Set1 | | 96 | 99 | 97 | 95 | 97 |
| Accuracy (%) - Set2 | | 102 | 94 | 100 | 96 | 102 |
| Accuracy (%) - Set3 | | 71 | 101 | 101 | 97 | 104 |
| % RSD (N = 3) | | 19% | 4% | 2% | 1% | 4% |

TABLE 7

Assay accuracy using target peptide IAFSATR (SEQ ID NO: 29) derived from C1q B subunit.

| Standard | L1 | L2 | L3 | L4 | L5 | L6 |
|---|---|---|---|---|---|---|
| Nominal Conc. (μg/mL) | 0.27 | 0.82 | 2.47 | 7.41 | 22.22 | 66.67 |
| Accuracy (%) | 101 | 95 | 106 | 98 | 99 | 100 |

| QC (N = 3) | | LLOQ | LQC | MQC | HQC | ULOQ |
|---|---|---|---|---|---|---|
| Nominal Conc. (μg/mL) | | 0.27 | 0.78 | 6.25 | 50 | 66.67 |
| Accuracy (%) - Set1 | | 98 | 95 | 97 | 105 | 96 |
| Accuracy (%) - Set2 | | 94 | 94 | 100 | 106 | 111 |
| Accuracy (%) - Set3 | | 99 | 94 | 95 | 109 | 113 |
| % RSD (N = 3) | | 3% | 1% | 3% | 2% | 9% |

TABLE 8

Calibration of C1q assay based on target peptide QTHQPPAPNSLIR (SEQ ID NO: 36) derived from C1q C subunit.

| Standard | L1 | L2 | L3 | L4 | L5 | L6 |
|---|---|---|---|---|---|---|
| Nominal Conc. (μg/mL) | 0.27 | 0.82 | 2.47 | 7.41 | 22.22 | 66.67 |
| Accuracy (%) | 101 | 95 | 103 | 100 | 101 | 100 |

| QC (N = 3) | | LLOQ | LQC | MQC | HQC | ULOQ |
|---|---|---|---|---|---|---|
| Nominal Conc. (μg/mL) | | 0.27 | 0.78 | 6.25 | 50 | 66.67 |
| Accuracy (%)—Set1 | | 98 | 98 | 99 | 106 | 99 |
| Accuracy (%)—Set2 | | 104 | 101 | 103 | 105 | 110 |
| Accuracy (%)—Set3 | | 93 | 97 | 102 | 107 | 111 |
| % RSD (N = 3) | | 6% | 2% | 2% | 1% | 6% |

These results demonstrate that the assay is both accurate and sensitive. They also demonstrate that using the peptide IAFSATR (SEQ ID NO: 29) derived from subunit B of C1q provided the best results, as there was a high response recorded by LC-SRM-MS/MS and the signal was free of background interference.

LLOQ and Limit of Detection (LOD)

Figure 8A:
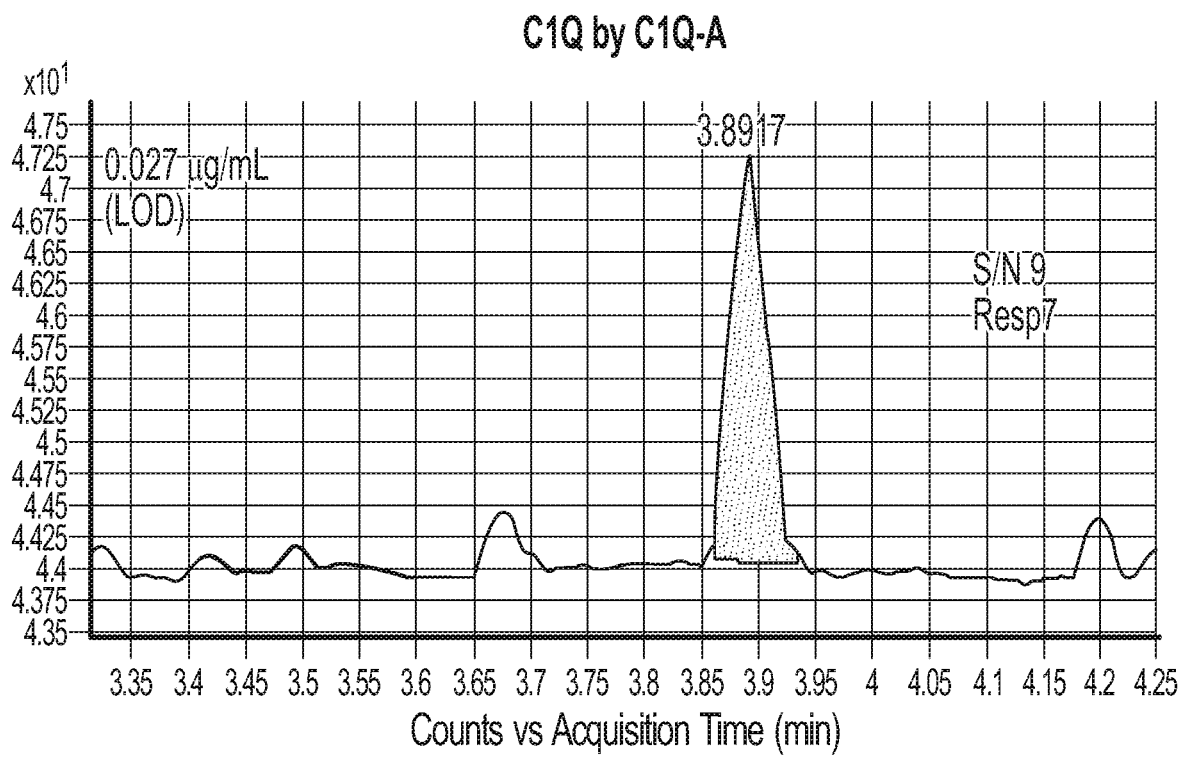
FIG. 8A, FIG. 8B and FIG. 8C are a series of LC-SRM-MS/MS chromatograms of selected peptides derived from the A, B, and C subunits of C1q in Limit of Detection (LOD) and LLOQ samples showing the signal to noise and response values for the highlighted peaks.
Figure 8A:
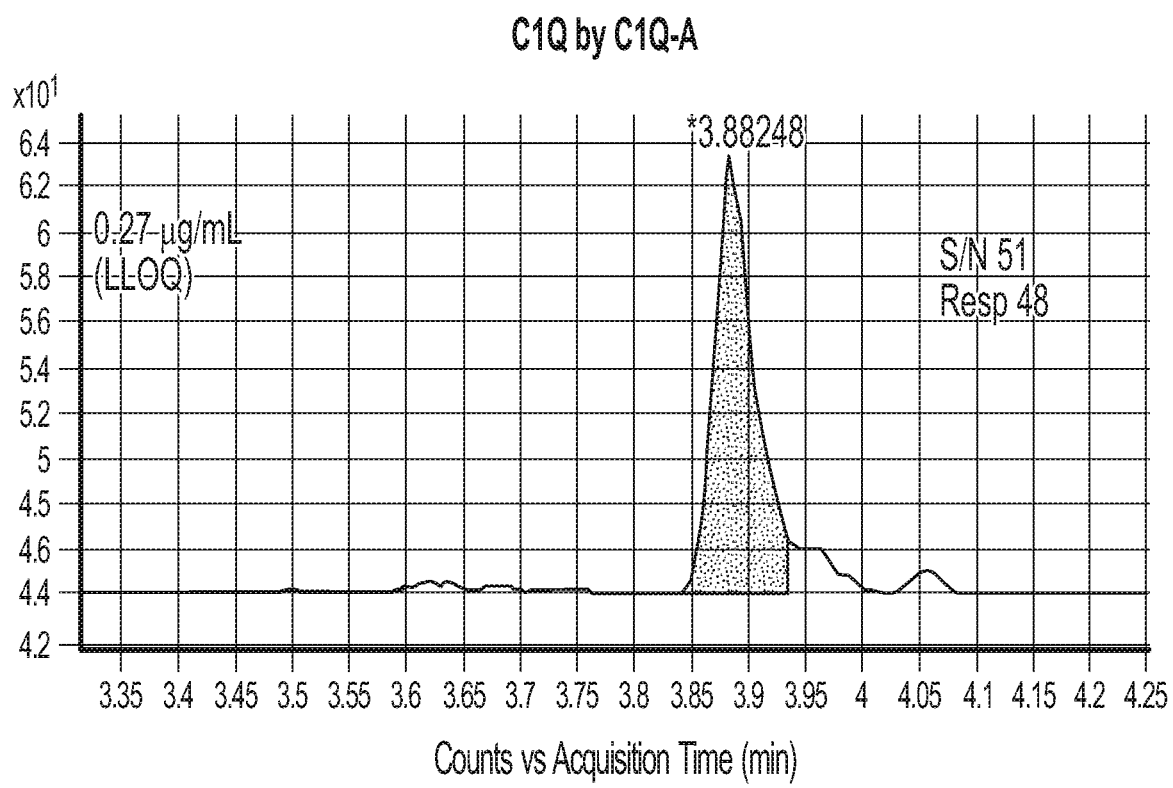
Figure 8B:
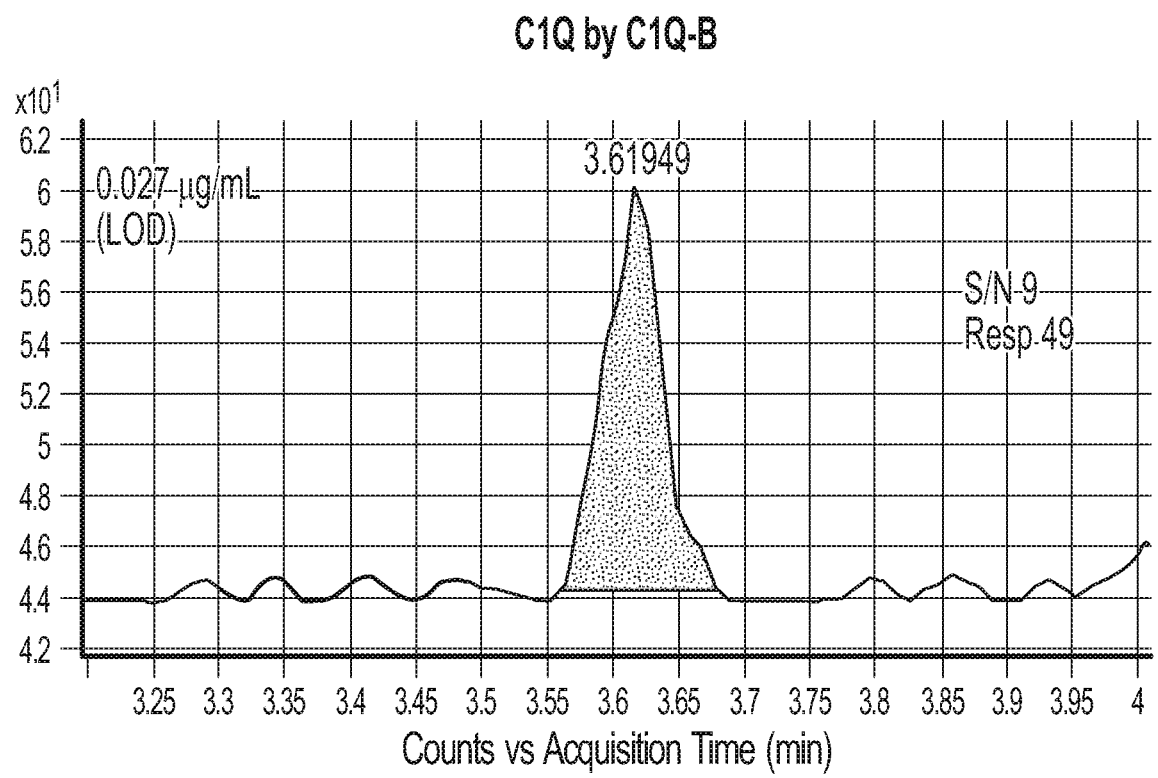
Figure 8B:
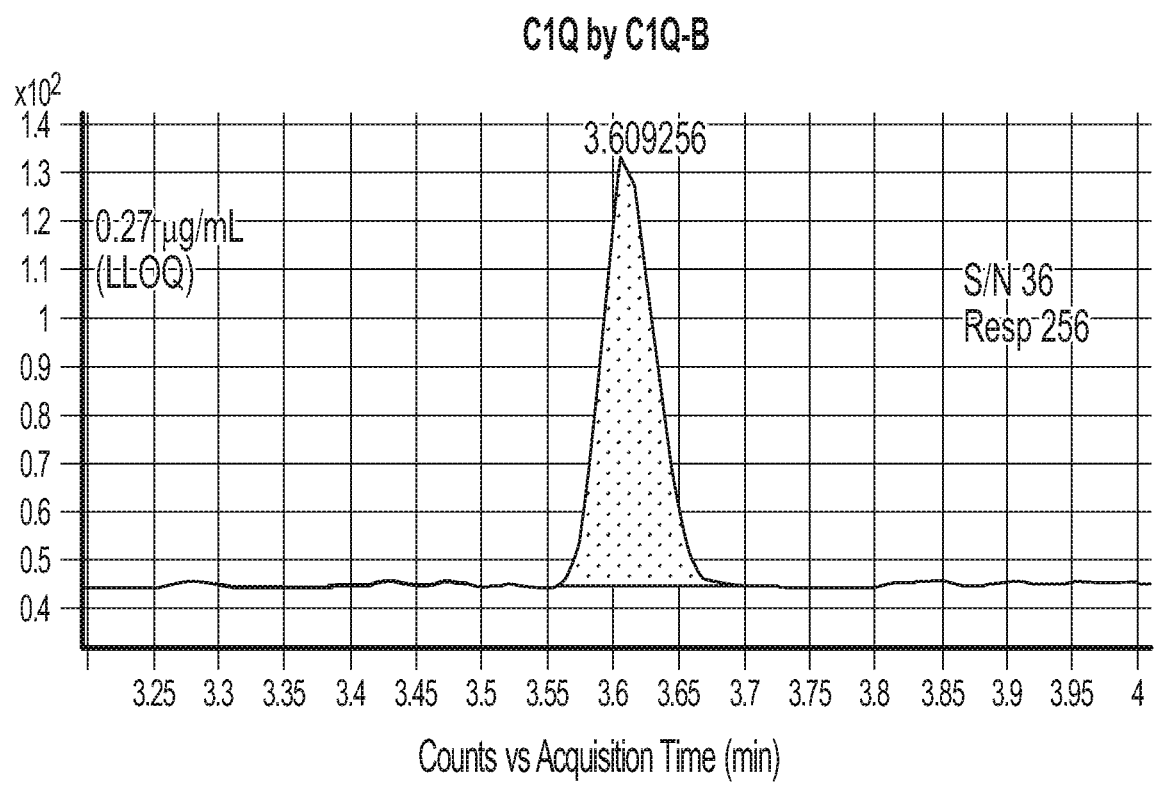
Figure 8C:
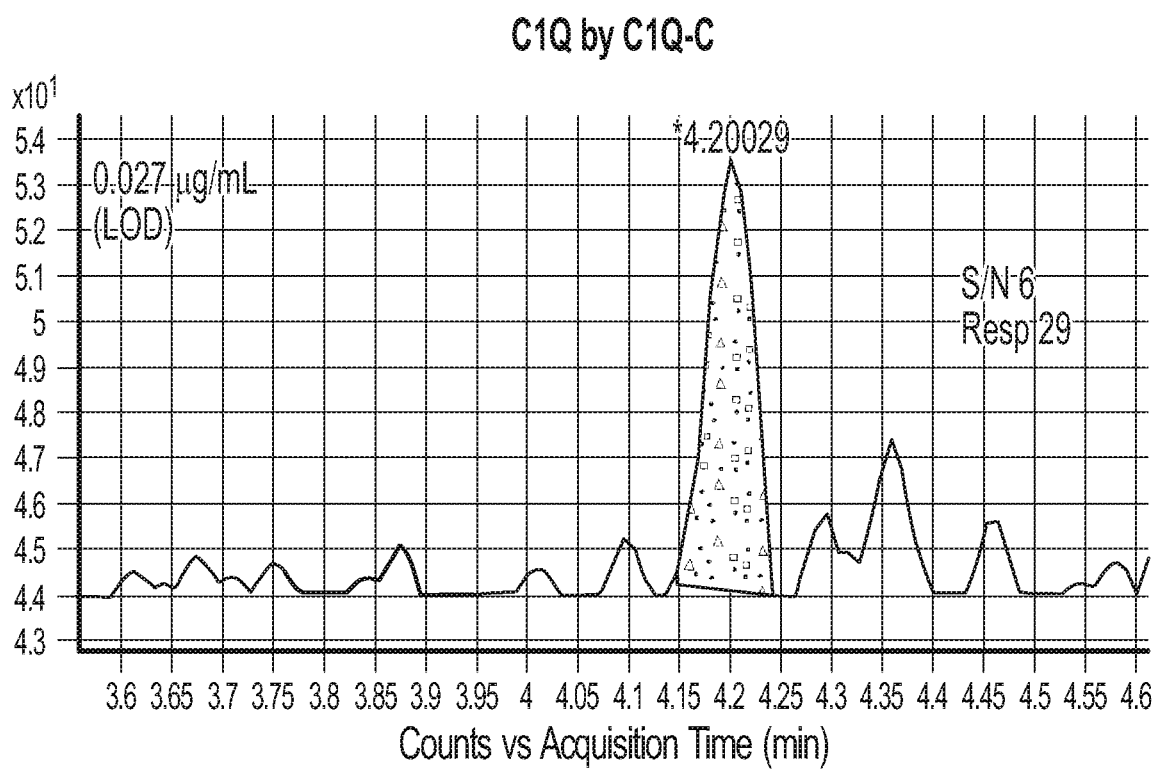
Figure 8C:
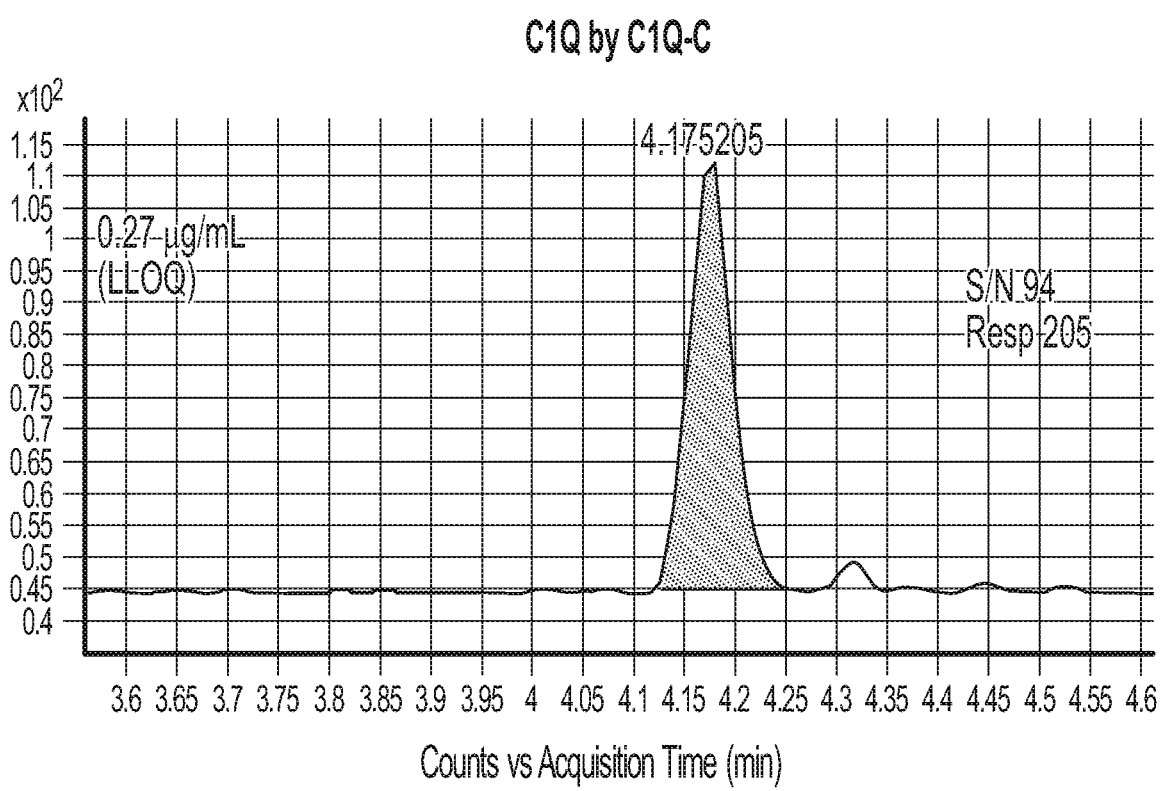
Figure 9A:
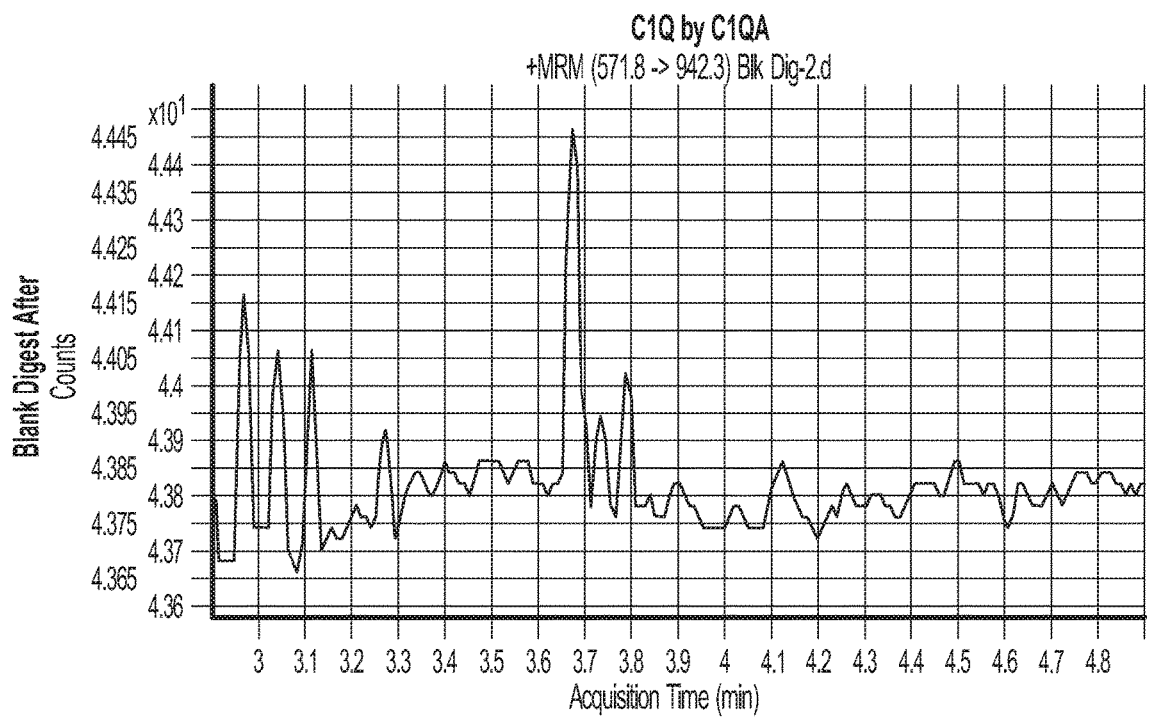
FIG. 9A, FIG. 9B, FIG. 9C, FIG. 9D and FIG. 9E are a series of LC-SRM-MS/MS chromatograms of selected peptides derived from the A, B, and C subunits of C1q in blank digest samples before and after analyzing a ULOQ sample.
Figure 9A:
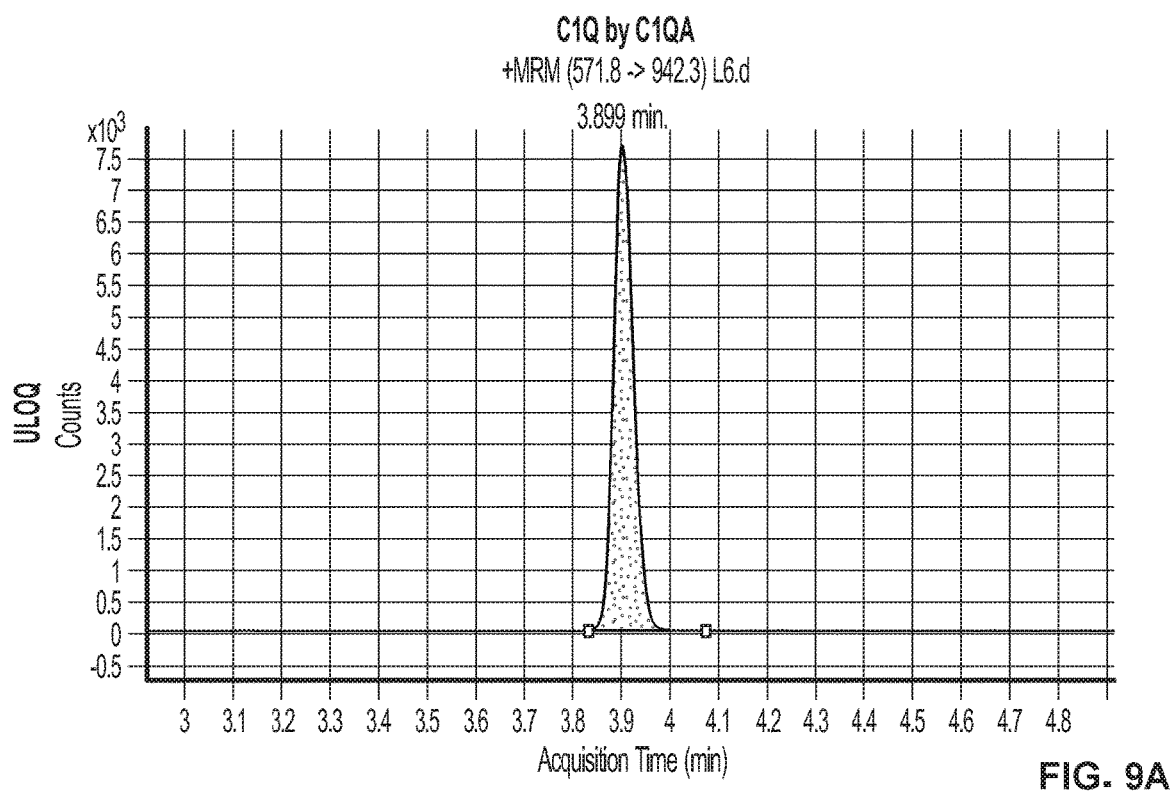
Figure 9B:
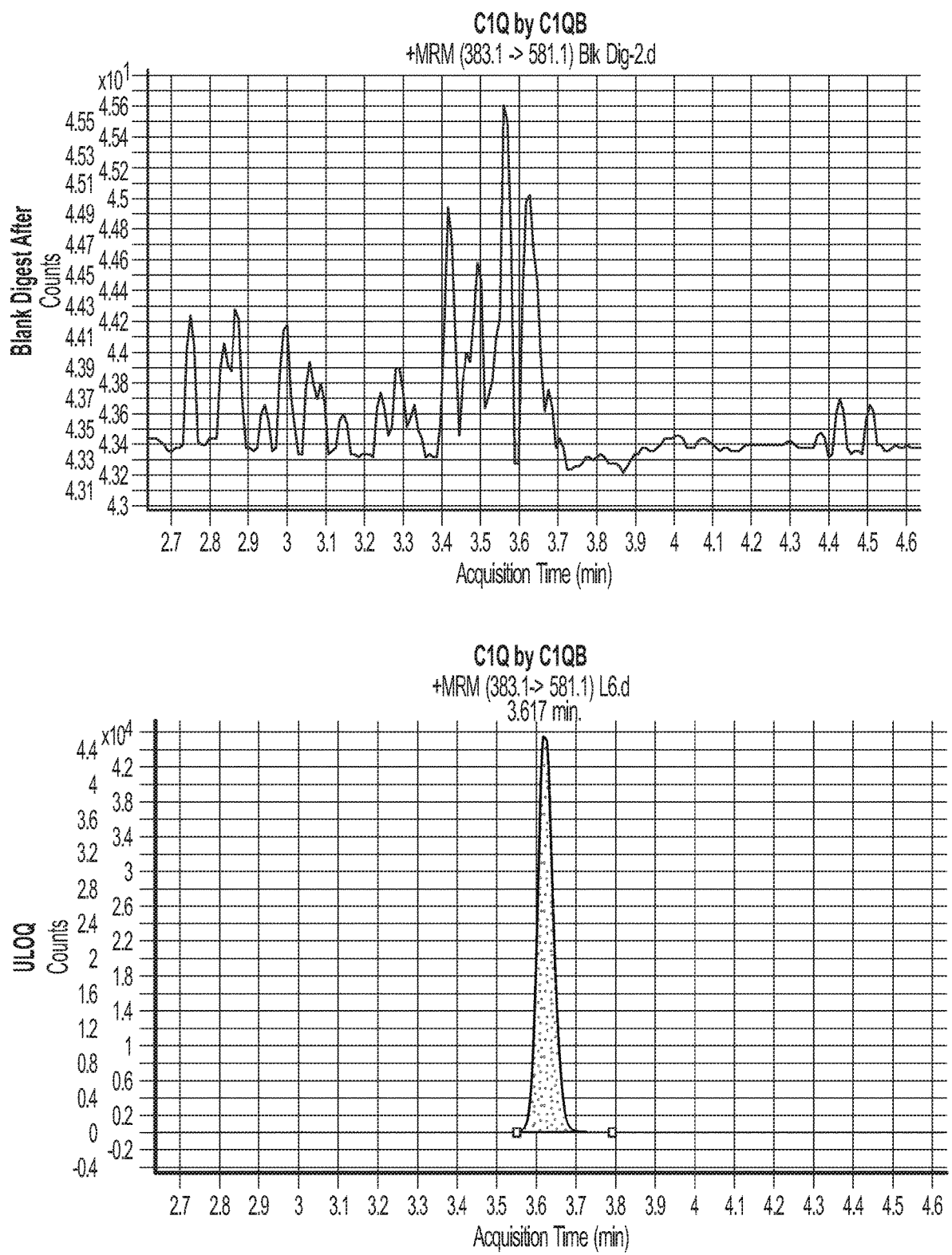
Figure 9C:
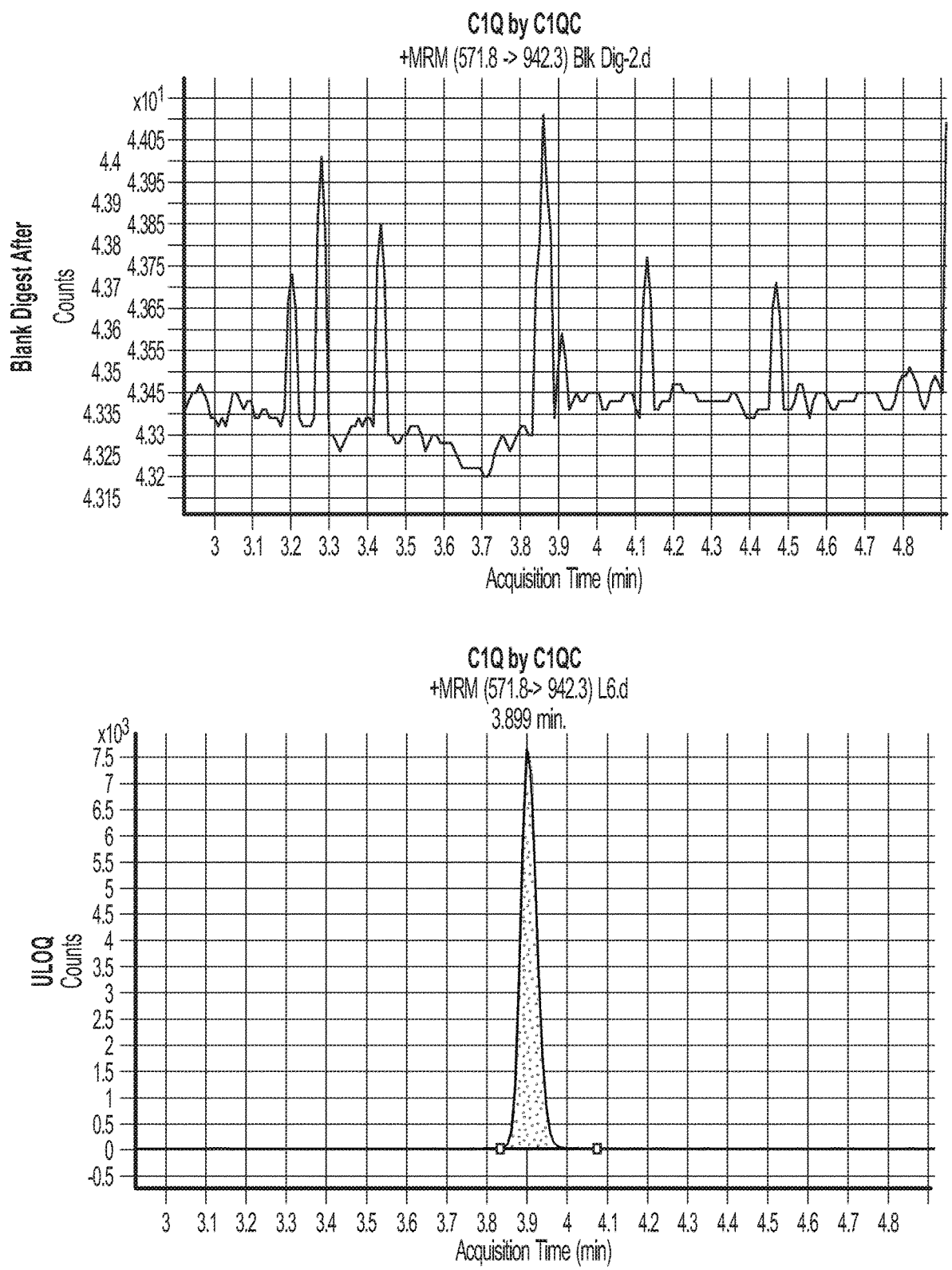
Figure 9D:
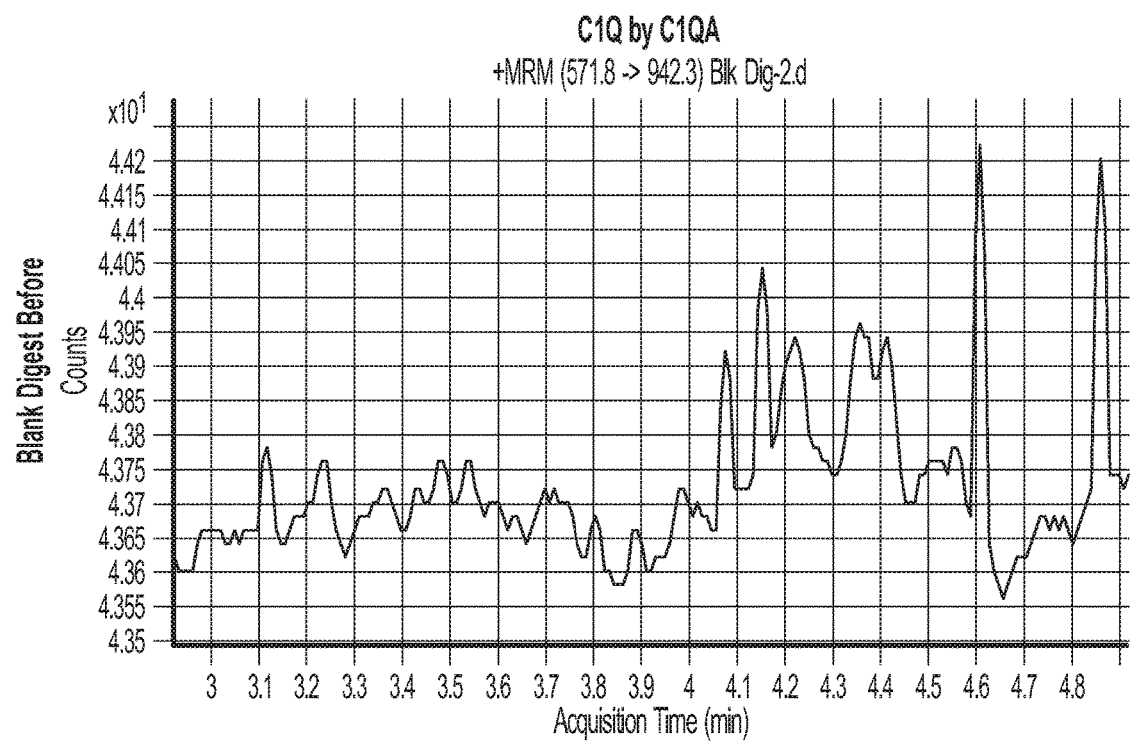
Figure 9D:
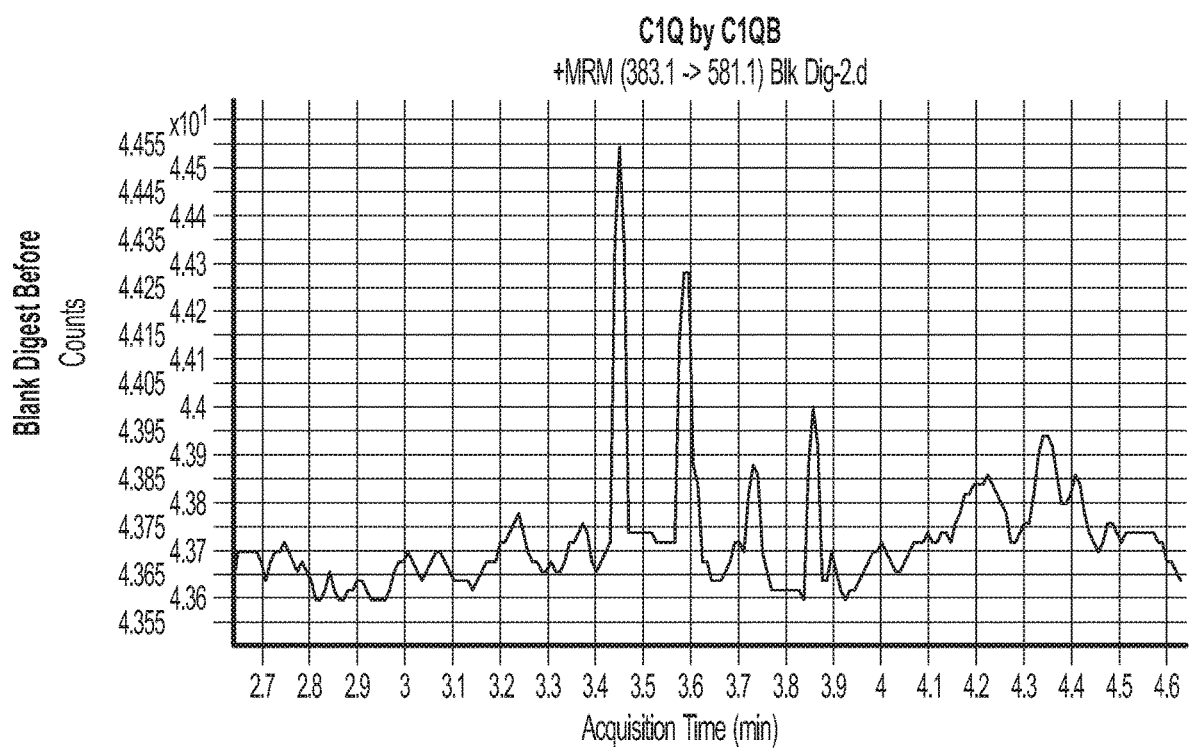
Figure 9E:
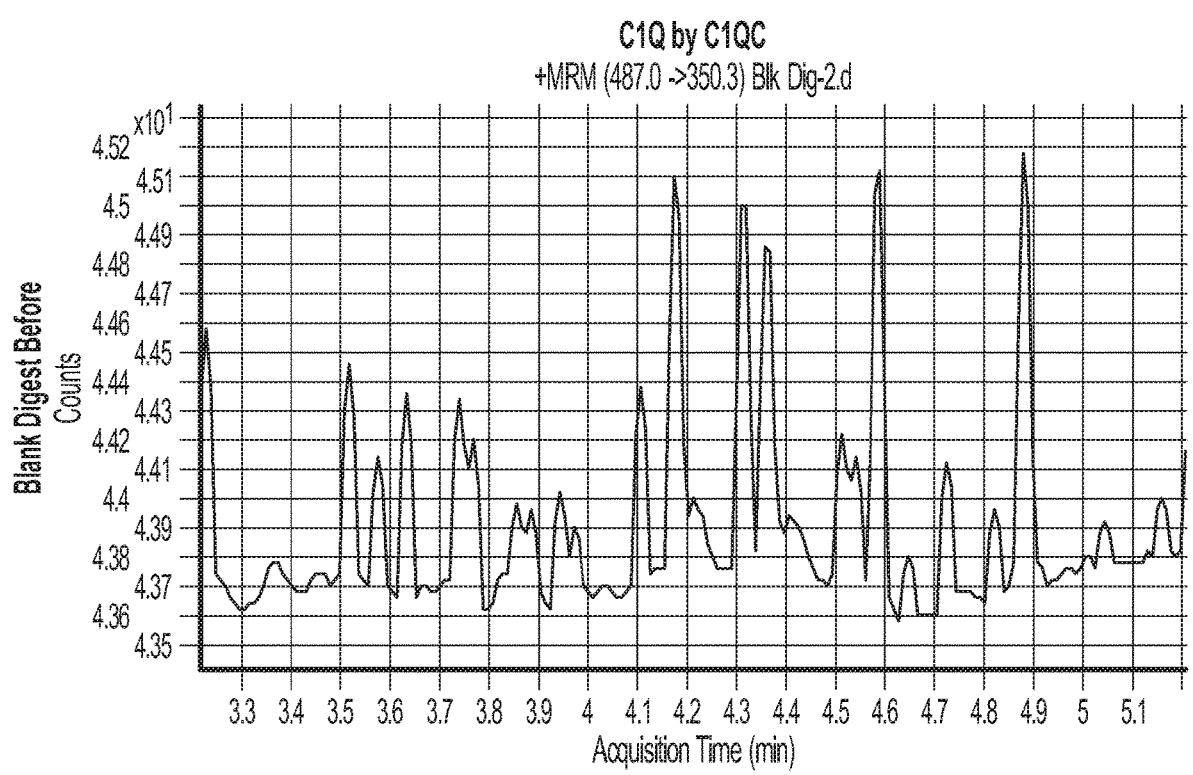
Figure 10A:
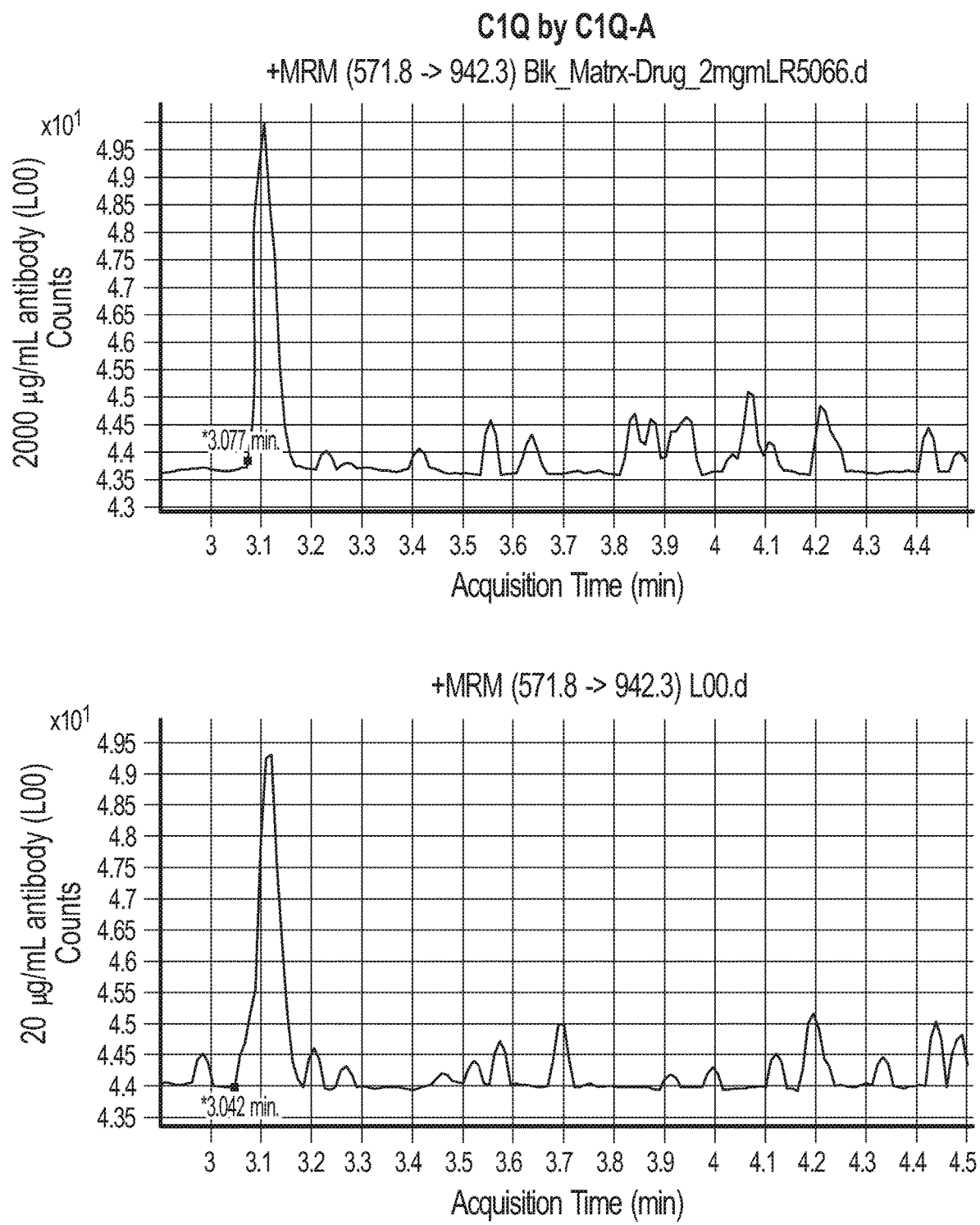
FIG. 10A, FIG. 10B, FIG. 10C, FIG. 10D, FIG. 10E and FIG. 10F show the LC-SRM-MS/MS chromatograms of selected peptides derived from the A, B, and C subunits of C1q in Double Blank (L00) standard solutions supplemented with 2000 µg/mL bispecific antibody, 20 µg/mL bispecific antibody or no bispecific antibody, and a LLOQ sample.
Figure 10B:
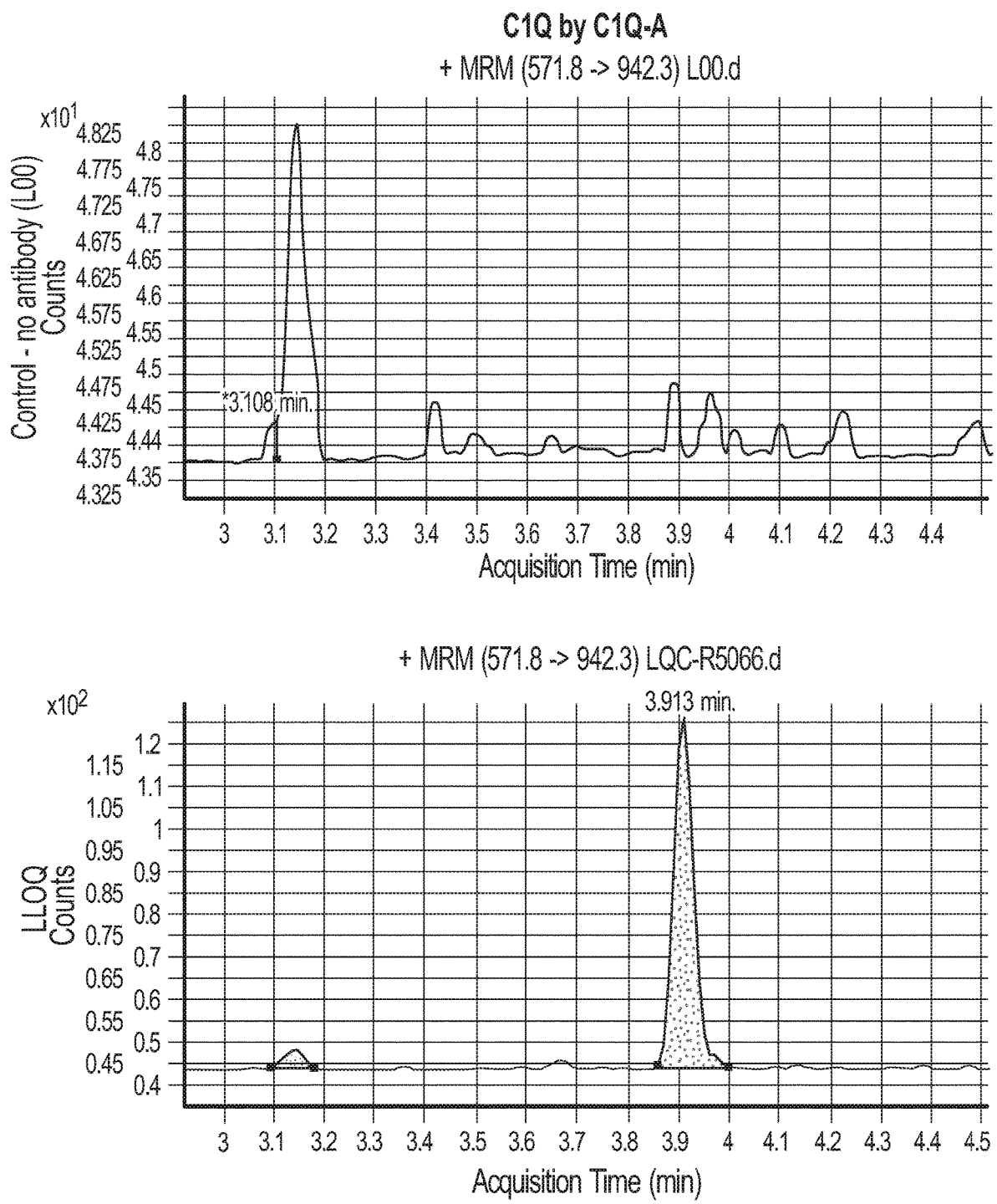
Figure 10C:
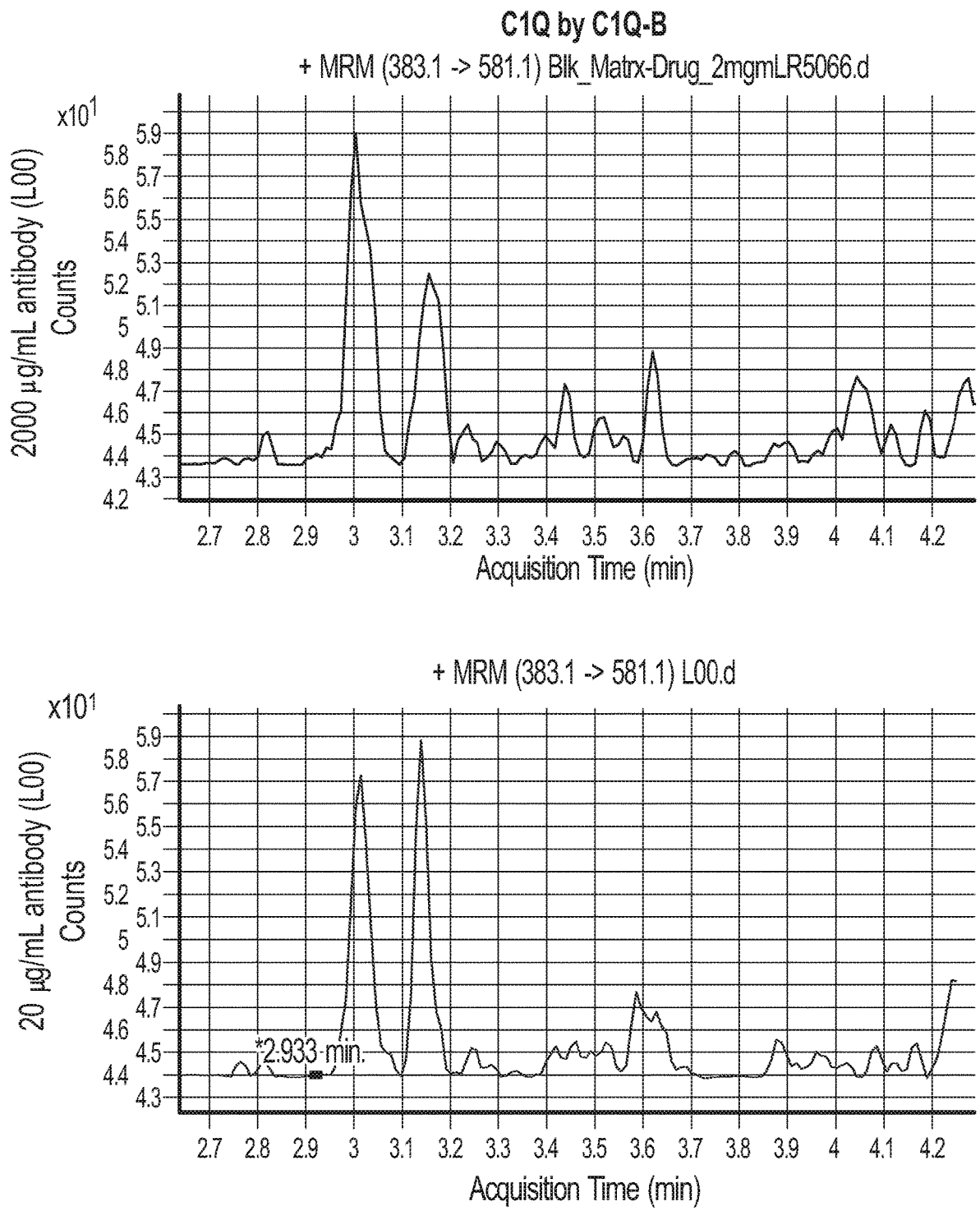
Figure 10D:
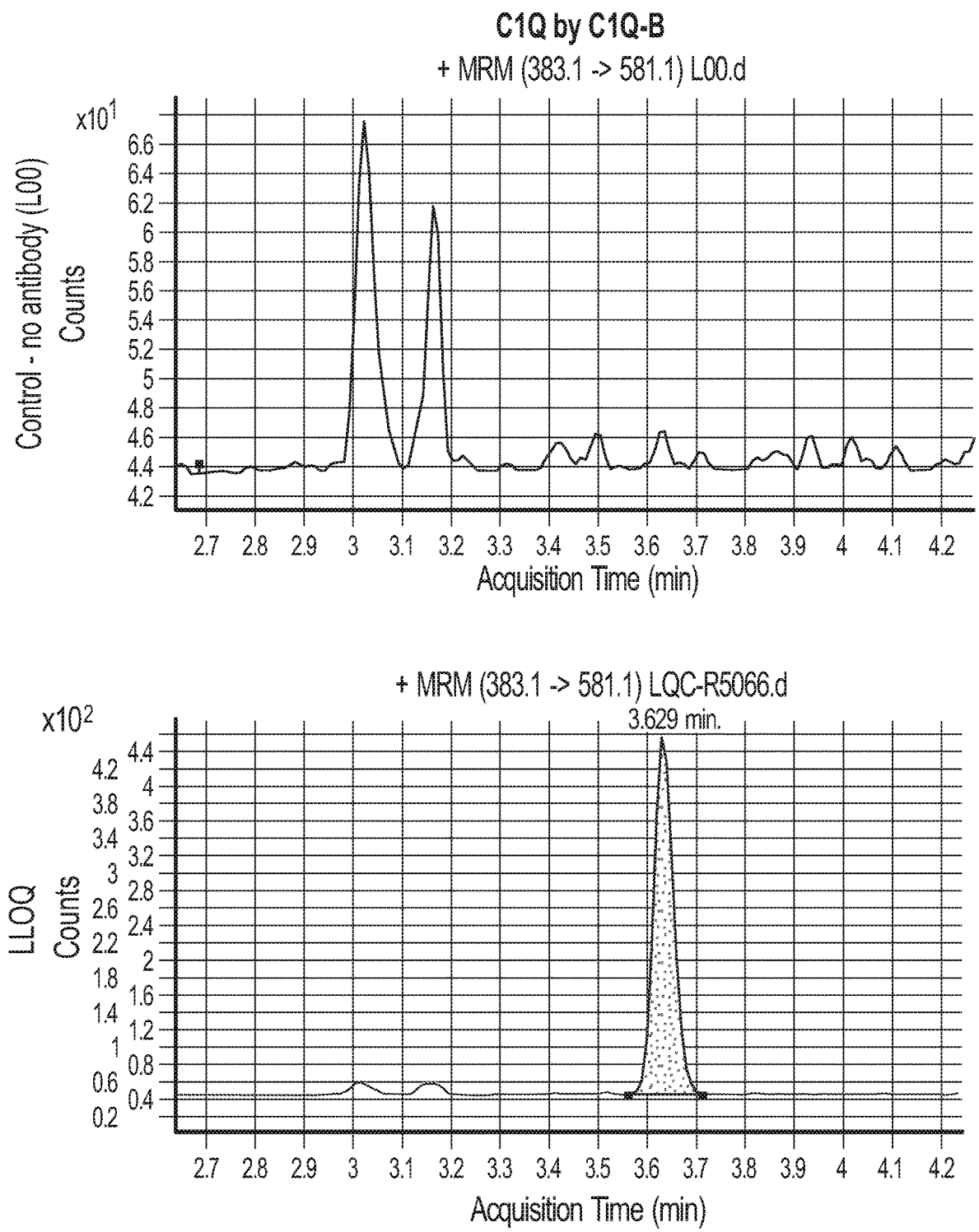
Figure 10E:
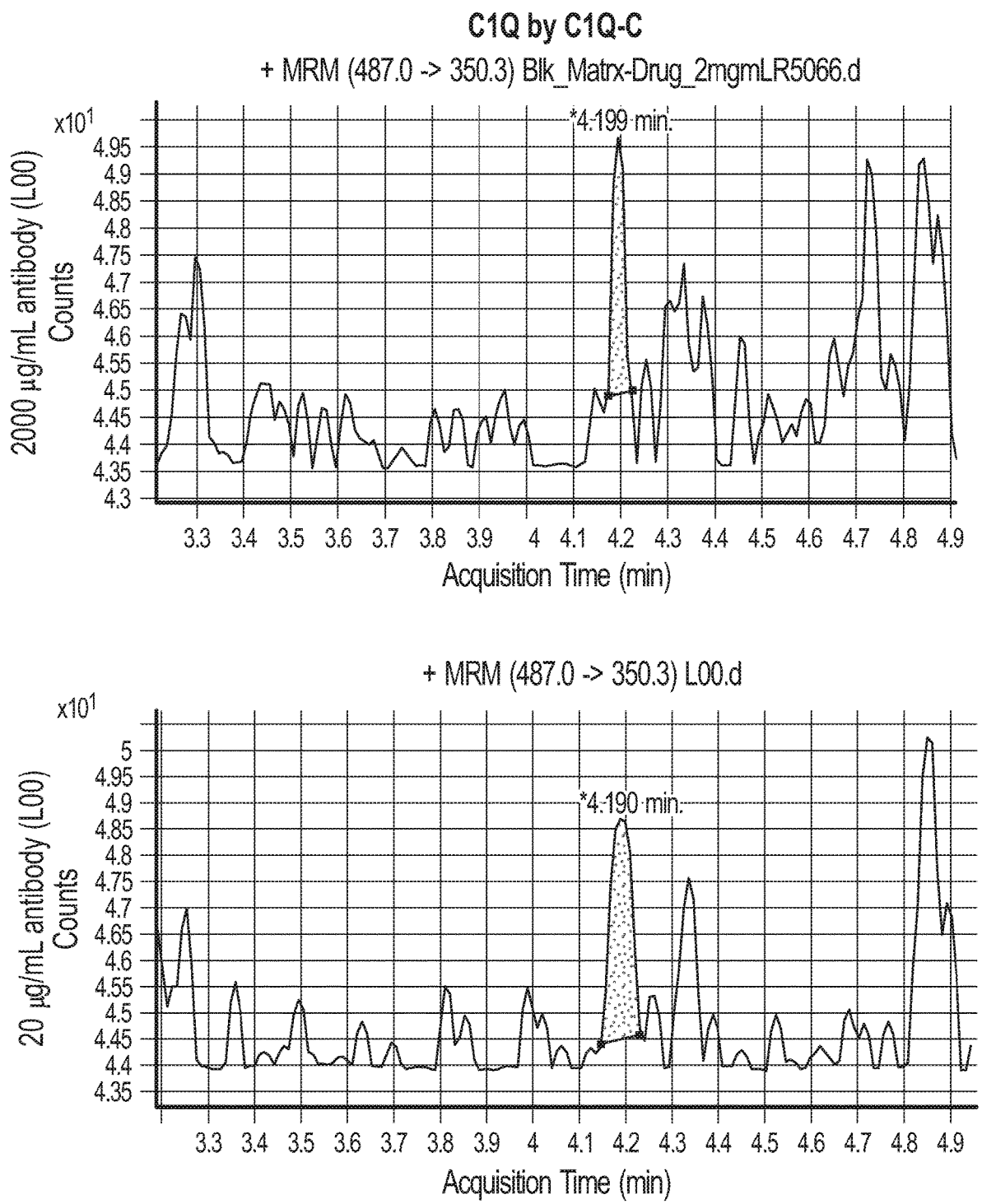
Figure 10F:
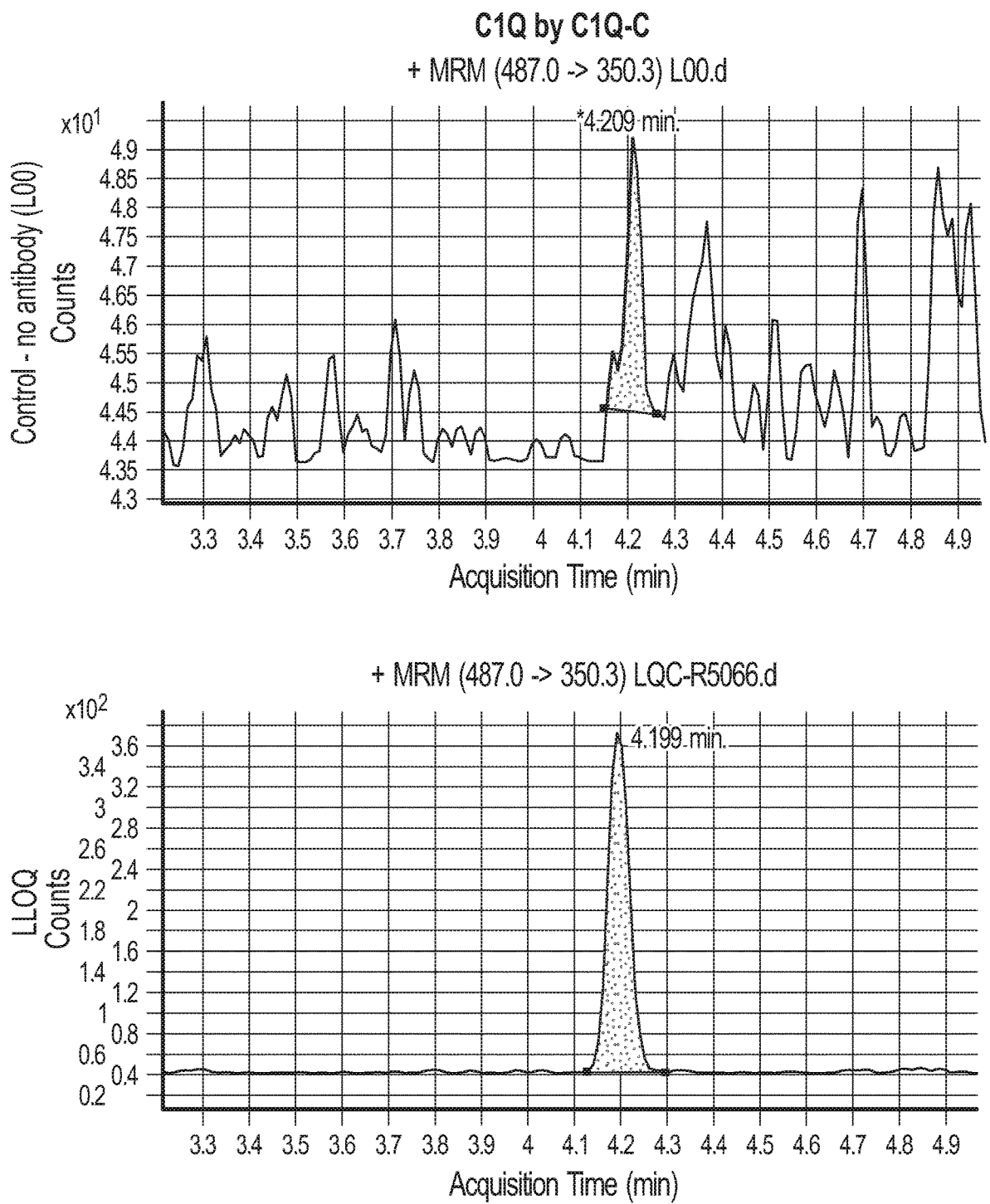

As shown in FIGS. 7A-7F, mass chromatogram recorded at the LLOQ concentration (0.27 μg/mL) for the subunit A peptide and the subunit B peptide exhibited little to no background peaks located at the same acquisition time as the peptide peaks in the blank and double blank samples. However, as show in FIGS. 7A-7F, the mass chromatogram recorded for the subunit C peptide exhibited background peaks in the blank and double blank samples. The area under curve for the background peak in the blank sample was approximately 5% of the area under curve for the sample peak. Overall, as shown in FIGS. 8A-8C, the signal to noise ratios for the subunit A peptide, the subunit B peptide and the subunit C peptide at the LLOQ concentration were 51, 36, 94, respectively and at the Limited of Detection (LOD) concentration were 7, 9 and 6 respectively.

Example 2—Testing Instrument Carryover of the Methods of the Present Disclosure

As the methods of the present disclosure may be used to perform consecutive experiments on the same instrument, it is important to make sure that the carryover from the last sample will not interfere with the assay for the next sample. The instrument carryover during the practice of the methods of the present disclosure was measured.

An LC-SRM-MS chromatogram was first recorded for a blank digest sample. Immediately after, a mass chromatogram for a C1q QC sample at the ULOQ concentration (66.7 μg/mL) was recorded on the same instrument. Finally, a second blank digest sample was analyzed on the same instrument after the analysis of the ULOQ sample. As shown in FIGS. 9A-9E, there was no significant change in the blank digest chromatograms before or after analyzing the ULOQ sample for the subunit A, subunit B or subunit C peptide. These results demonstrate that the instrument carryover for the methods of the present disclosure is minimal.

Example 3—Testing Drug Tolerance of the Methods of the Present Disclosure

To examine whether or not the presence of antibody drugs interferes with the methods of the present disclosure, different concentrations (0, 20 μg/mL, or 2000 μg/mL) of a bispecific antibody were added to C1q reference samples at the Double Blank (blank matrix only, without internal standard; L00) concentration. As shown in FIGS. 10A-10F, the addition of the bispecific antibody did not produce any significant changes in the recorded mass chromatogram.

Figure 11:
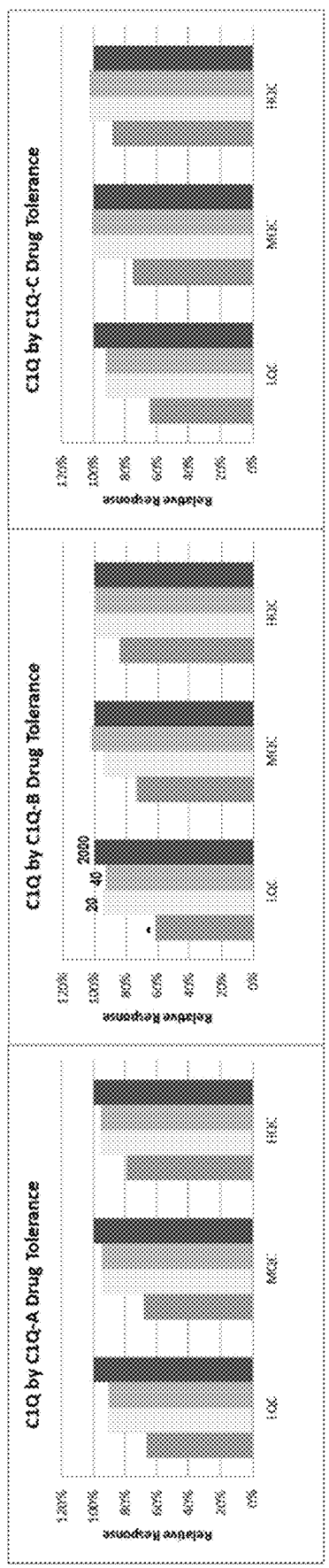
FIG. 11 is a series of charts showing the relative response of C1q in samples incubated with bispecific antibody measured using the methods of the present disclosure.

C1q reference samples at the LQC, MQC and HQC concentrations (0.8 μg/mL, 6.3 μg/mL and 50.0 μg/mL respectively) were incubated in the absence of the bispecific antibody or with either 0 μg/mL, 20 μg/mL, 40 μg/mL, or 2000 μg/mL of the bispecific antibody and analyzed using LC-SRM-MS/MS. These concentrations of the bispecific antibody in the C1q assay corresponded to 1 mg/mL, 2 mg/mL, or 100 mg/mL of the bispecific antibody in neat serum. To put these concentrations in the context of pharmacokinetics, when administered at the dosage of 50 mg/kg, the peak serum concentration ($C_{max}$) of the bispecific antibody 6 is 1.25-1.5 mg/mL. As shown in FIG. 11, the addition of the bispecific antibody actually improves the recovery of signal for the subunit A, subunit B and subunit C peptides. In FIG. 11, the pink or first bar in each group corresponds to samples incubated in the absence of the bispecific antibody; the yellow or second bar in each group corresponds to samples incubated with 20 μg/mL of the bispecific antibody; the green or third bar in each group corresponds to samples incubated with 40 μg/mL of the bispecific antibody; the blue or fourth bar in each group corresponds to samples incubated with 2000 μg/mL of the bispecific antibody.

Figure 12:
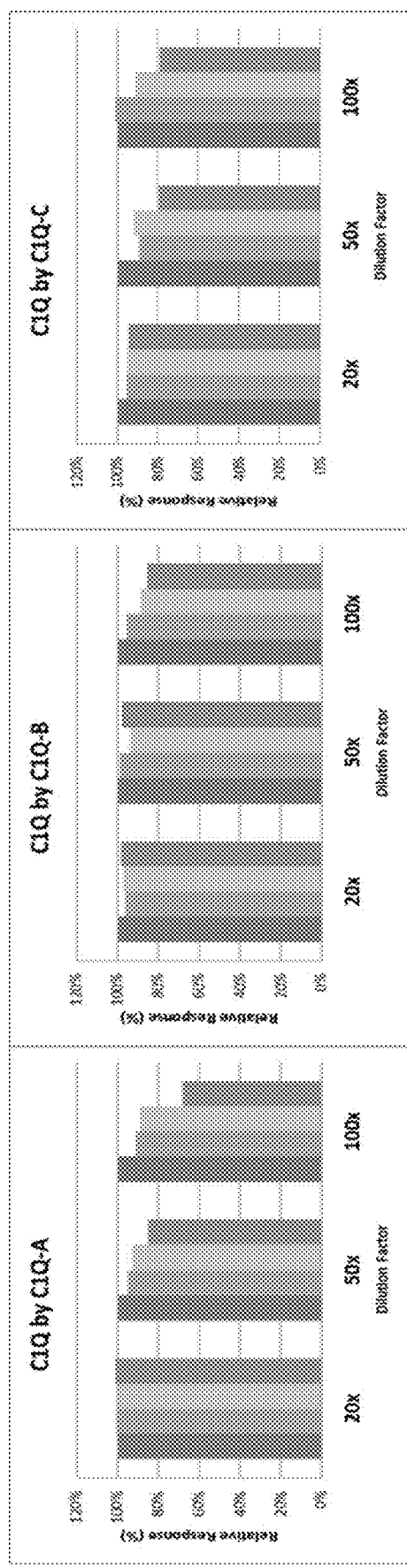
FIG. 12 is a series of charts showing the relative response measured for endogenous C1q in samples diluted at different dilution factors in different diluents using the methods of the present disclosure.

Example 4—Testing Dilution Recovery and Dilution Linearity of the Methods of the Present Disclosure The recovery of endogenous C1q signal in the methods of the present disclosure was also tested in samples diluted in different diluents and with different dilution factors. The diluents tested included 2% depleted human serum incubated with 20 μg/mL of the bispecific antibody, 2% depleted human serum, 0.1% BSA and a Tris-HCl solution. These samples were diluted 20×, 50× and 100× and LC-SRM-MS/MS was used to analyze the dilutions. As shown in FIG. 12, the addition of the bispecific antibody improves the recovery of the subunit A, subunit B and subunit C peptide signals even at higher dilution factors. There was a lower signal recovery in samples diluted with 0.1% BSA and Tris-HCl. In FIG. 12, the blue or first bar in each group corresponds to samples diluted with 2% depleted human serum incubated with 20 μg/mL of the bispecific antibody; the orange or second bar in each group corresponds to samples diluted with 2% depleted human serum; the green or third bar in each group corresponds to samples diluted with 0.1% BSA; the purple or fourth bar in each group corresponds to samples diluted with Tris-HCl.

Figure 13:
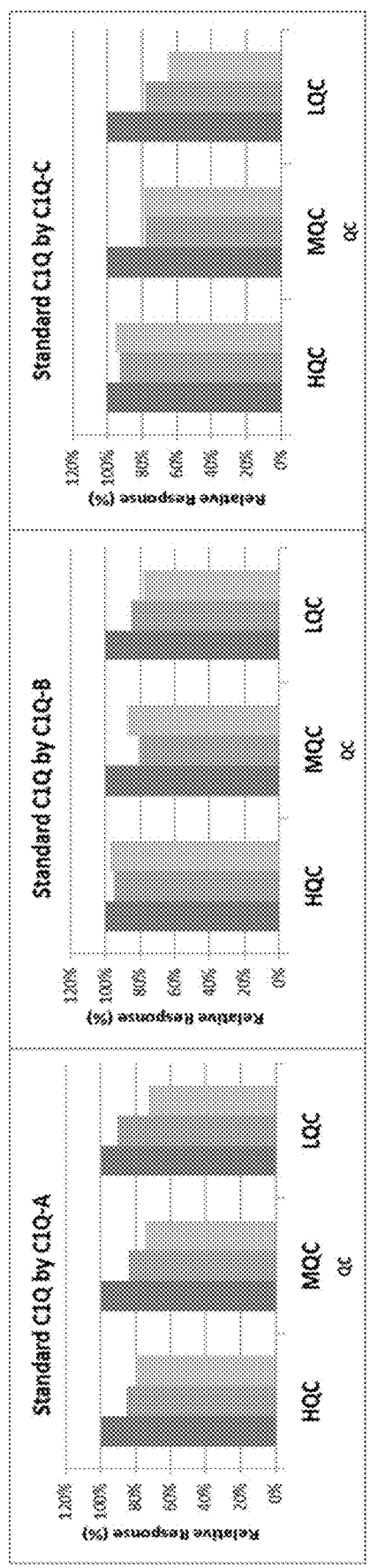
FIG. 13 is a series of charts showing the relative response measured for C1q in samples diluted at different dilution factors in different diluents using the methods of the present disclosure.

The recovery of signal from C1q reference standards using different diluents was also tested. C1q reference samples at LQC, MQC and HQC concentrations (0.8 μg/mL, 6.3 μg/mL and 50.0 μg/mL respectively) were diluted with either 2% depleted human serum incubated with 20 μg/mL of the bispecific antibody, 2% depleted human serum or 0.1% BSA. As shown in FIG. 13, the bispecific antibody improved the recovery of the subunit A, subunit B and subunit C peptide signals. In FIG. 13, the blue or first bar in each group corresponds to samples diluted with 2% depleted human serum incubated with 20 μg/mL of the bispecific antibody; the orange or second bar in each group corresponds to samples diluted with 2% depleted human serum; the green or third bar in each group corresponds to samples diluted with 0.1% BSA.

To test the dilution linearity of the methods of the present disclosure, pooled human serum, male monkey, and female monkey samples were diluted by 20 times, 50 times, and 100 times. The concentrations of endogenous C1q in these diluted samples were determined using the methods of the present disclosure. The results of this test are shown in Table 9 below.

TABLE 9

Dilution linearity test with endogenous C1q.

| | | By C1Q-A | | By C1Q-B | | By C1Q-C | |
|---|---|---|---|---|---|---|---|
| Sample | Dilution Factor | Cal. Conc. (ug/mL) | % RSD | Cal. Conc. (ug/mL) | % RSD | Cal. Conc. (ug/mL) | % RSD |
| Pooled | 100X | 89 | 12.4% | 80 | 5.3% | 78 | 6.0% |
| Human | 50X | 70 | | 72 | | 70 | |
| Serum | 20X | 87 | | 74 | | 74 | |
| Male | 100X | 87 | 8.7% | 59 | 0.8% | 61 | 2.7% |
| Monkey | 50X | 81 | | 58 | | 60 | |
| | 20X | 96 | | 58 | | 58 | |

TABLE 9-continued

Dilution linearity test with endogenous C1q.

| Sample | Dilution Factor | By C1Q-A | | By C1Q-B | | By C1Q-C | |
|---|---|---|---|---|---|---|---|
| | | Cal. Conc. (ug/mL) | % RSD | Cal. Conc. (ug/mL) | % RSD | Cal. Conc. (ug/mL) | % RSD |
| Female Monkey | 100X | 70 | 2.1% | 56 | 6.2% | 55 | 8.7% |
| | 50X | 67 | | 49 | | 50 | |
| | 20X | 69 | | 54 | | 59 | |

Example 5—Sample Preparation Repeatability and Sample Stability in Methods of the Present Disclosure Sample preparation repeatability of the methods of the present disclosure were tested using C1q QC samples at LLOQ, LQC, MQC, HQC, and ULOQ concentrations. For injection repeatability, aliquots of same QC sample were injected into the assay instrument either on same day (intra-day) or on different days (inter-day). For sample preparation repeatability, samples were prepared from QC solutions either on same day (intra-day) or on different days (inter-day). 3 samples for each condition were tested, and the relative standard deviation of the 3 samples for each condition is shown in Table 10 below.

TABLE 10

Injection and sample preparation repeatability of the methods of the present disclosure

| | | % RSD | | | |
|---|---|---|---|---|---|
| C1Q | QC (n = 3) | Intra-day Injector | Inter-day Injector | Intra-day Sample Prep | Inter-day Sample Prep |
| C1Q-A | LLOQ | 0.6 | 10.2 | 3.0 | 14.0 |
| | LQC | 7.8 | 7.1 | 9.2 | 13.7 |
| | MQC | 1.2 | 5.4 | 2.7 | 4.3 |
| | HQC | 1.2 | 1.3 | 0.9 | 1.3 |
| | ULOQ | 2.5 | 2.0 | 2.0 | 2.0 |
| C1Q-B | LLOQ | 4.8 | 5.0 | 0.8 | 6.0 |
| | LQC | 4.4 | 9.3 | 2.0 | 4.6 |
| | MQC | 1.8 | 6.2 | 1.5 | 3.9 |
| | HQC | 0.5 | 2.0 | 1.2 | 1.8 |
| | ULOQ | 0.4 | 0.8 | 1.2 | 1.7 |
| C1Q-C | LLOQ | 6.8 | 6.2 | 4.6 | 5.6 |
| | LQC | 1.3 | 1.6 | 3.3 | 5.6 |
| | MQC | 2.3 | 2.0 | 3.2 | 2.9 |
| | HQC | 1.3 | 2.2 | 1.6 | 2.5 |
| | ULOQ | 1.0 | 1.9 | 1.9 | 2.7 |

Figure 14:
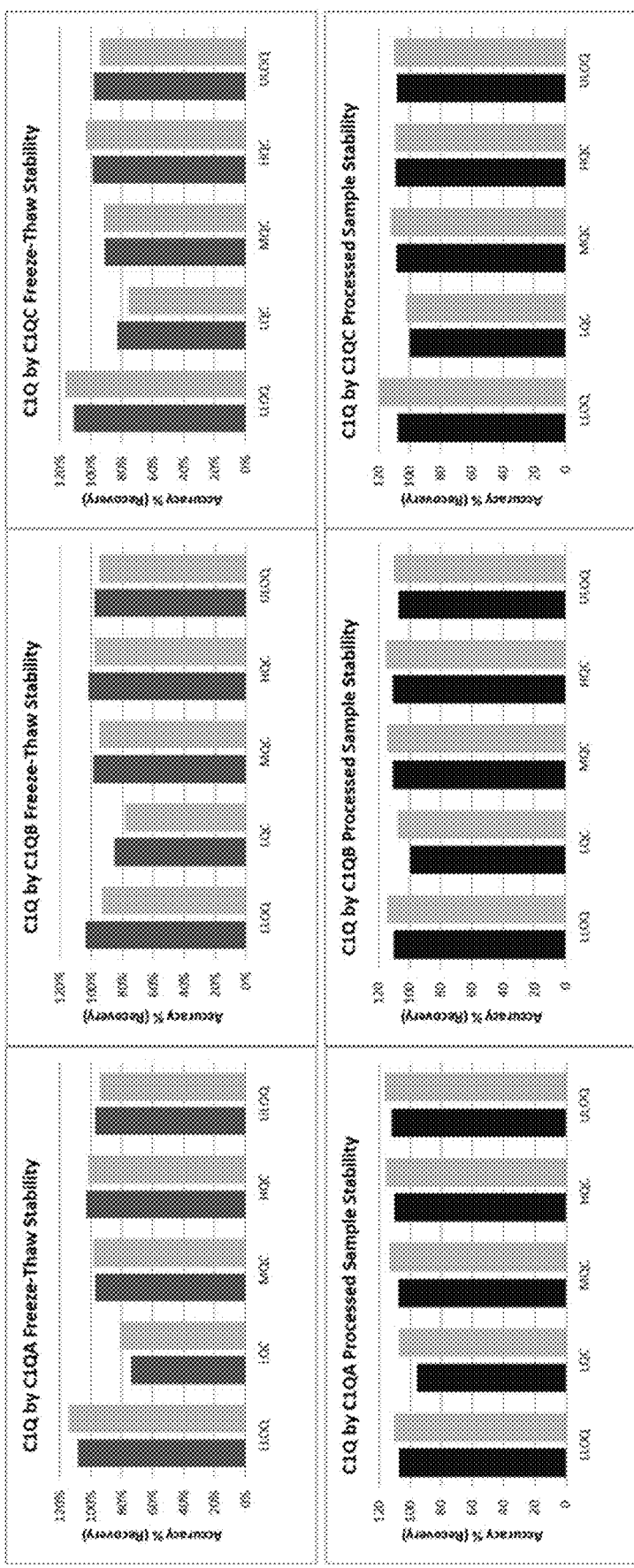
FIG. 14 is a series of charts showing the accuracy of measured concentration for C1q in samples subjected to three freeze thaw cycles or stored in an autosampler for 48 hours using the methods of the present disclosure.

For sample stability, C1q QC samples at LLOQ, LQC, MQC, HQC, and ULOQ concentrations (0.3 µg/mL, 0.8 µg/mL, 6.3 µg/mL, 50.0 µg/mL, and 66.7 µg/mL respectively) were either subjected to three freeze thaw cycles, or stored in an autosampler for 48 hours before their C1q concentrations were determined by the C1q assay. As shown FIG. 14, the accuracy of the methods of the present disclosure were not significantly affected by three freeze thaw cycles, or by 48 hours storage in an autosampler. In the top row of charts in FIG. 14, the first bar in each group corresponds to samples that were freshly analyzed before freezing; the second bar in each group corresponds to samples that were subjected to three freeze thaw cycles. In the bottom row of charts in FIG. 14, the first bar in each group corresponds to samples that were freshly analyzed; the second bar in each group corresponds to samples that were analyzed after 48 hours storage in an autosampler.

In separate experiments, 72 hours storage was also tested, and no sample degradation or loss was observed.

Example 6—Assay Variation Related to Internal Standard Peptides in Methods of the Present Disclosure Heavy isotope labelled peptides; called internal standard peptides (ISPs) have identical amino acid sequences as the subunit A, subunit B and subunit C peptides. C1q QC samples at LLOQ, LQC, MQC, HQC, and ULOQ concentrations (0.3 µg/mL, 0.8 µg/mL, 6.3 µg/mL, 50.0 µg/mL and 66.7 µg/mL respectively) were analyzed in the presence and absence of each ISP. The results of this analysis are shown in Table 11. The inclusion of the ISPs did not interfere with the analysis. Therefore, isotope labelled peptides used for retention time confirmation, instrument performance calibration, and troubleshooting purposes.

TABLE 11

C1q assay variation with or without isotope labelled internal standard peptides

| | % RSD of QC (n = 3) | | | | | |
|---|---|---|---|---|---|---|
| | C1QA | | C1QB | | C1QC | |
| QC (n = 3) | −ISP | +ISP | −ISP | +ISP | −ISP | +ISP |
| LLOQ | 8% | 12% | 4% | 2% | 2% | 8% |
| LQC | 11% | 11% | 4% | 2% | 2% | 1% |
| MQC | 2% | 6% | 3% | 5% | 2% | 4% |
| HQC | 2% | 6% | 1% | 4% | 0% | 8% |
| ULOQ | 2% | 3% | 1% | 1% | 2% | 7% |

Example 6—Quantitation of C1q in Blood Samples from Treated Monkeys Using the Methods of the Present Disclosure The methods of the present disclosure were used to quantify the concentration of C1q protein present in the blood samples of monkeys treated with a bispecific antibody. The monkey group designation and dose levels are shown in Table 12.

TABLE 12

Monkey group designation and dose levels

| Group | No. of animals (male) | Dose level (mg/kg) | Dose concentration (mg/mL) |
|---|---|---|---|
| 1 (Isotype control) | 3 | 50 | 25 |
| 2 (Low) | 3 | 2 | 1 |
| 3 (Mid) | 3 | 10 | 5 |
| 4 (High) | 3 | 50 | 25 |

Group 1 was administered diluted an isotype control antibody via slow bolus intravenous injection at a dose volume of 2 mL/kg. Groups 2, 3, and 4 were administered a diluted bispecific antibody via slow bolus intravenous injection at a dose of 2 mL/kg. 0.5 mL blood samples were collected according the following schedule: pre-dose sample and approximately 5 minutes after dose sample were collected on Day 1; subsequent samples were collected at 24 hours, 72 hours and 168 hours after dose; samples were also collected once on each of Day 14 after dose, Day 42 after dose and Day 56 after dose. Blood samples were centrifuged for 1 hours after collection, and the harvested serum samples were split into 4 aliquots, 50 µL each.

Each monkey serum sample was diluted by 50 times in 100 mM Tris-HCl, pH 7.5 and 20 µg/mL of the bispecific antibody. 5 µL of each diluted monkey serum sample was then denatured and reduced in 20 µL of 8 M urea and 10 mM tris(2-carboxyethyl)phosphine (TCEP) at 56° C. with shaking for 30 minutes. 5 µL of 50 mM iodoacetamide was then added to each sample, and the samples were then incubated in the dark at 25° C. with shaking for 30 minutes. 10 µL of the appropriate isotope-labelled internal standard peptide solution (see Example 1) was added before 100 µL of 0.01 µg/µL trypsin was added to each sample. The samples were then incubated at 37° C. in the dark with shaking for 4 hours. 5 µL of 20% of formic acid was added to the samples to quench the tryptic digestion reaction. The samples were mixed and centrifuged at 4680 rpm for 5 minutes before they were analyzed by LC-SRM-MS/MS.

For each monkey serum sample, LC-SRM-MS/MS was used to record the signal corresponding to the subunit A peptide, the subunit B peptide and the subunit C peptide, as well as the signals corresponding to the isotope-labelled internal standard peptides.

Figure 15:
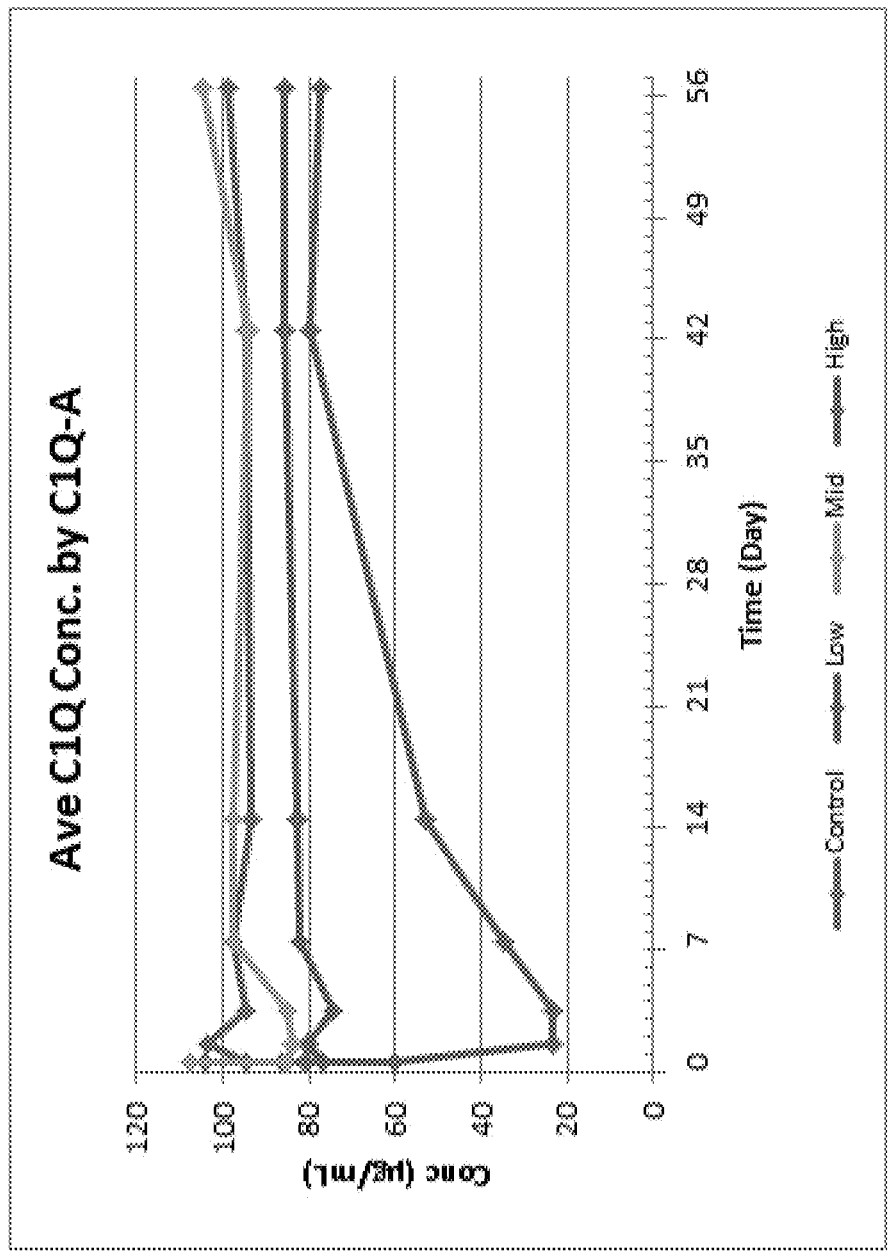
FIG. 15 shows a chart depicting the C1q concentration over time in the blood samples from dosed monkeys, determined using the methods of the present disclosure and a selected peptide derived from the A subunit of C1q.
Figure 16:
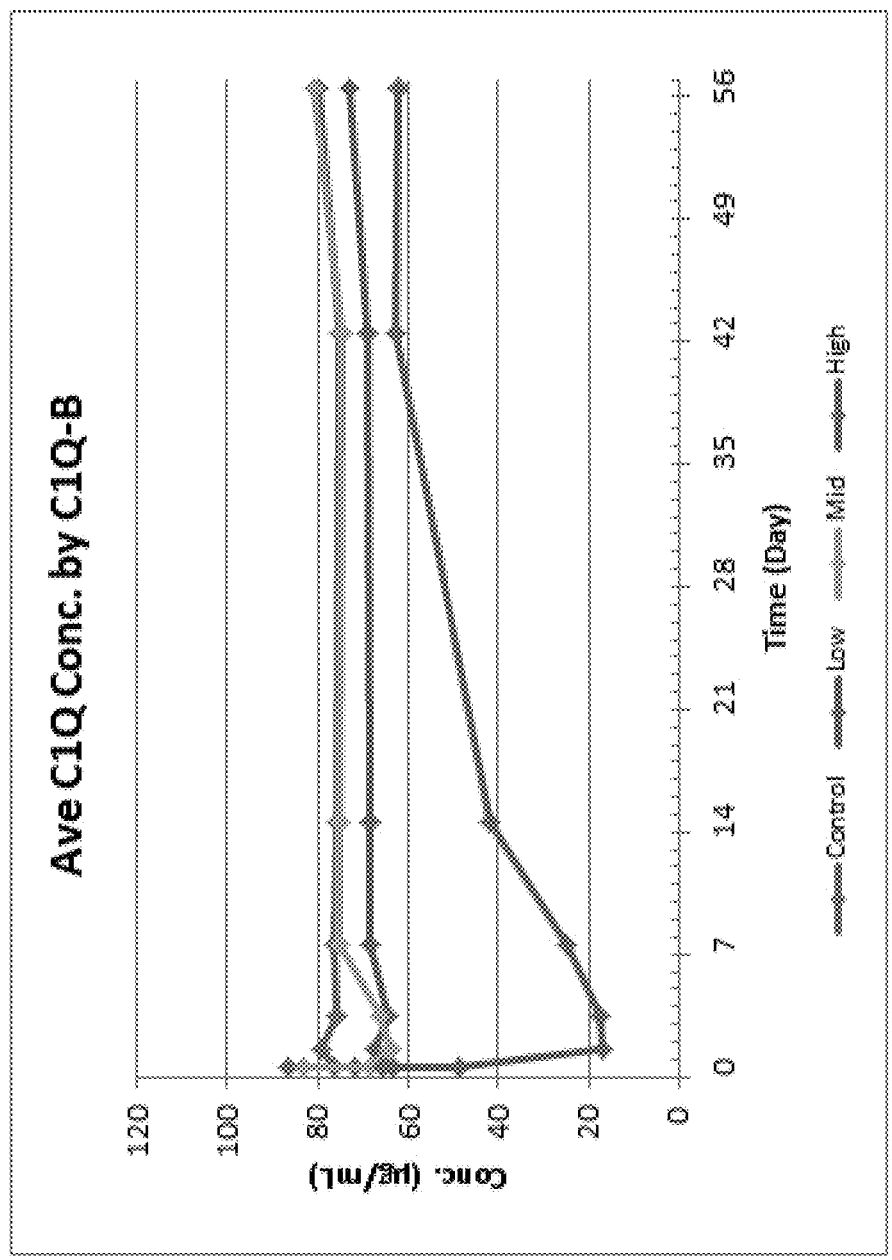
FIG. 16 shows a chart depicting the C1q concentration over time in the blood samples from dosed monkeys, determined using the methods of the present disclosure and a selected peptide derived from the B subunit of C1q.
Figure 17:
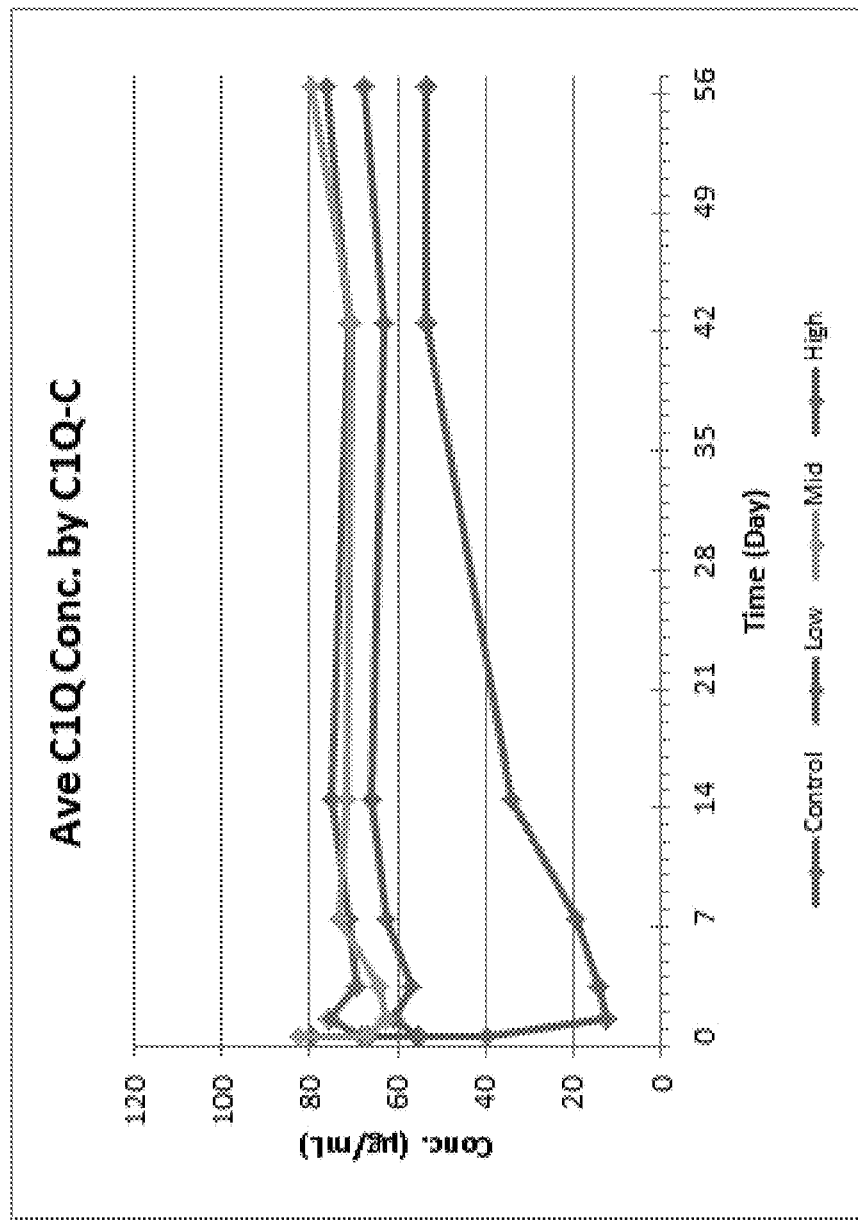
FIG. 17 shows a chart depicting the C1q concentration over time in the blood samples from dosed monkeys, determined using the methods of the present disclosure and a selected peptide derived from the C subunit of C1q.

The concentrations of C1q in each of the dosed monkey serum samples were then determined by comparing the signals of the subunit A, subunit B and subunit C peptides to calibration curves (generated as described in Example 1) The concentrations of C1q, as determined by the subunit A peptide, subunit B peptide and subunit C peptide, are shown in Tables 13-15. The post dose time course of C1q concentrations in monkey blood are depicted in FIGS. 15-17. FIG. 15 shows the concentration of C1q in the dose monkey samples quantified using the subunit A peptide. FIG. 16 shows the concentration of C1q in the dose monkey samples quantified using the subunit B peptide. FIG. 17 shows the concentration of C1q in the dose monkey samples quantified using the subunit C peptide. In FIG. 15-17, the blue line corresponds to monkeys in Group 1, the red line corresponds to monkeys in Group 2, the green line corresponds to monkeys in Group 3 and the purple line corresponds to monkeys in Group 4.

TABLE 13

Quantitation of dosed monkey blood samples for C1q concentration by target peptide SLGFCDTTNK (SEQ ID NO: 26) derived from C1q A subunit.

| | Concentration of C1q by Subunit A (µg/mL) | | | | | | | | | | | |
|---|---|---|---|---|---|---|---|---|---|---|---|---|
| Time | Group 1 (Isotype Control) | | | Group 2 (Low) | | | Group 3 (Mid) | | | Group 4 (High) | | |
| Point | P0001 | P0002 | P0003 | P0101 | P0102 | P0103 | P0201 | P0202 | P0203 | P0301 | P0302 | P0303 |
| Pre-dose | 124 | 87 | 102 | 89 | 93 | 76 | 114 | 120 | 90 | 59 | 92 | 92 |
| 5 min | 102 | 88 | 94 | 78 | 81 | 72 | 90 | 91 | 74 | 43 | 70 | 67 |
| 24 h | 118 | 83 | 108 | 78 | 89 | 74 | 84 | 102 | 66 | 4* | 58 | 9* |
| 72 h | 112 | 76 | 96 | 80 | 79 | 64 | 93 | 96 | 67 | 5* | 53 | 13* |
| 168 h | 116 | 80 | 96 | 81 | 86 | 79 | 106 | 106 | 81 | 8* | 67 | 28 |
| D14 | 105 | 77 | 99 | 78 | 100 | 70 | 120 | 93 | 79 | 25 | 71 | 63 |
| D42 | 106 | 81 | 96 | 74 | 103 | 80 | 85 | 106 | 91 | 56 | 83 | 99 |
| D56 | 109 | 91 | 96 | 79 | 104 | 74 | 105 | 117 | 92 | 53 | 86 | 94 |

*An estimated C1q concentration. Concentrafon below LLOQ (0.27 µg/mL) but above LOD (0.027 µg/mL).

TABLE 14

Quantitation of dosed monkey blood samples for C1q concentration by target peptide IAFSATR (SEQ ID NO: 29) derived from C1q B subunit.

| | Concentration of C1q by Subunit B (µg/mL) | | | | | | | | | | | |
|---|---|---|---|---|---|---|---|---|---|---|---|---|
| Time | Group 1 (Isotype Control) | | | Group 2 (Low) | | | Group 3 (Mid) | | | Group 4 (High) | | |
| Point | P0001 | P0002 | P0003 | P0101 | P0102 | P0103 | P0201 | P0202 | P0203 | P0301 | P0302 | P0303 |
| Pre-dose | 99 | 72 | 88 | 69 | 79 | 67 | 90 | 93 | 67 | 49 | 75 | 74 |
| 5 min | 82 | 67 | 80 | 61 | 69 | 59 | 71 | 77 | 58 | 34 | 58 | 55 |
| 24 h | 90 | 66 | 82 | 66 | 75 | 62 | 65 | 76 | 51 | 1* | 44 | 5* |
| 72 h | 90 | 63 | 75 | 59 | 75 | 59 | 72 | 73 | 53 | 2* | 44 | 7* |
| 168 h | 88 | 67 | 74 | 66 | 77 | 62 | 82 | 81 | 64 | 6* | 50 | 19 |
| D14 | 85 | 68 | 75 | 62 | 77 | 66 | 85 | 78 | 63 | 17 | 60 | 49 |
| D42 | 86 | 65 | 76 | 61 | 79 | 67 | 75 | 80 | 69 | 46 | 66 | 76 |
| D56 | 82 | 76 | 82 | 63 | 88 | 68 | 84 | 85 | 74 | 44 | 69 | 73 |

*An estimated C1q concentration. Concentrafon below LLOQ (0.27 µg/mL) but above LOD (0.027 µg/mL).

TABLE 15

Quantitation of dosed monkey blood samples for C1q concentration by target peptide QTHQPPAPNSLIR (SEQ ID NO: 36) derived from C1q C subunit.

| | Concentration of C1q by Subunit C (µg/mL) | | | | | | | | | | | |
|---|---|---|---|---|---|---|---|---|---|---|---|---|
| Time Point | Group 1 (Isotype Control) | | | Group 2 (Low) | | | Group 3 (Mid) | | | Group 4 (High) | | |
| | P0001 | P0002 | P0003 | P0101 | P0102 | P0103 | P0201 | P0202 | P0203 | P0301 | P0302 | P0303 |
| Pre-dose | 94 | 66 | 78 | 65 | 73 | 62 | 94 | 88 | 66 | 51 | 41 | 73 |
| 5 min | 76 | 59 | 70 | 53 | 60 | 54 | 68 | 73 | 61 | 37 | 31 | 52 |
| 24 h | 88 | 63 | 76 | 57 | 68 | 58 | 62 | 75 | 51 | 6* | 23 | 9* |
| 72 h | 87 | 58 | 64 | 57 | 61 | 54 | 69 | 70 | 54 | 7* | 24 | 12* |
| 168 h | 79 | 62 | 72 | 62 | 69 | 58 | 79 | 81 | 60 | 8* | 28 | 22 |
| D14 | 86 | 67 | 73 | 61 | 77 | 59 | 79 | 74 | 62 | 21 | 34 | 48 |
| D42 | 82 | 60 | 73 | 53 | 74 | 62 | 71 | 76 | 66 | 45 | 39 | 77 |
| D56 | 78 | 73 | 78 | 58 | 82 | 62 | 85 | 80 | 74 | 47 | 39 | 75 |

*An estimated C1q concentration. Concentration below LLOQ (0.27 µg/mL) but above LOD (0.027 µg/mL).

What is claimed is:

1. An assay comprising:
   (1) contacting a biological sample with at least one proteolytic enzyme to produce at least one peptide fragment of the protein C1q present in the biological sample, wherein the at least one peptide fragment has an amino acid sequence of SLGFCDTTNK (SEQ ID NO: 26); and
   (2) performing selected reaction monitoring mass spectrometry (SRM-MS) to measure the abundance of the at least one C1q peptide fragment having the amino acid sequence of SLGFCDTTNK (SEQ ID NO: 26), wherein the abundance of the at least C1q peptide fragment having the amino acid sequence of SLGFCDTTNK (SEQ ID NO: 26) determines the concentration of C1q in the biological sample.

2. The assay of claim 1, further comprising between step (1) and step (2), adding to the biological sample at least one labeled, synthetic C1q peptide fragment comprising an amino acid sequence identical to the amino acid sequence of the at least one C1q peptide fragment having the amino acid sequence of SLGFCDTTNK (SEQ ID NO: 26).

3. The assay of claim 1, wherein measuring the abundance of the at least one C1q peptide fragment having the amino acid sequence of SLGFCDTTNK (SEQ ID NO: 26) comprises comparing a signal corresponding to the at least one C1q peptide fragment having the amino acid sequence of SLGFCDTTNK (SEQ ID NO: 26) generated by SRM-MS to a standard curve.

4. The assay of claim 1, wherein the biological sample is a blood sample.

5. The assay of claim 1, wherein the biological sample is a human sample.

6. The assay of claim 1, wherein the biological sample is a non-human primate sample.

7. The assay of claim 1, wherein the selected reaction monitoring mass spectrometry is LC-SRM-MS/MS.

8. The assay of claim 1, wherein the at least one proteolytic enzyme is trypsin.

9. The assay of claim 3, wherein the standard curve is produced using a method comprising:
   (a) preparing at least two C1q concentration standards by mixing known quantities of purified C1q protein and C1q-depleted serum;
   (b) adding to the at least two C1q concentration standards at least one labeled, synthetic peptide fragment with an amino acid sequence of SLGFCDTTNK (SEQ ID NO: 26);
   (c) contacting the at least two labeled C1q concentration standards with a proteolytic enzyme to produce at least one peptide fragment of C1q having the amino acid sequence of SLGFCDTTNK (SEQ ID NO: 26);
   (d) performing selected reaction monitoring mass spectrometry to determine the strength of the signal that corresponds to the at least one peptide fragment of C1q having the amino acid sequence of SLGFCDTTNK (SEQ ID NO: 26) and the strength of the signal that corresponds to the at least one labeled, synthetic peptide fragment having the amino acid sequence of SLGFCDTTNK (SEQ ID NO: 26) in each of the at least two labeled C1q concentration standards; and
   (e) determining a standard curve using the signals and the known quantities of C1q protein.

10. An assay comprising:
    (1) contacting a biological sample with at least one proteolytic enzyme to produce at least one peptide fragment of the protein C1q present in the biological sample, wherein the at least one peptide fragment has an amino acid sequence of QTHQPPAPNSLIR (SEQ ID NO: 36); and
    (2) performing selected reaction monitoring mass spectrometry (SRM-MS) to measure the abundance of the at least one C1q peptide fragment having the amino acid sequence of QTHQPPAPNSLIR (SEQ ID NO: 36), wherein the abundance of the at least C1q peptide fragment having the amino acid sequence of QTHQPPAPNSLIR (SEQ ID NO: 36) determines the concentration of C1q in the biological sample.

11. The assay of claim 10, further comprising between step (1) and step (2), adding to the biological sample at least one labeled, synthetic C1q peptide fragment comprising an amino acid sequence identical to the amino acid sequence of the at least one C1q peptide fragment having the amino acid sequence of QTHQPPAPNSLIR (SEQ ID NO: 36).

12. The assay of claim 10, wherein measuring the abundance of the at least one C1q peptide fragment having the amino acid sequence of QTHQPPAPNSLIR (SEQ ID NO: 36) comprises comparing a signal corresponding to the at least one C1q peptide fragment having the amino acid sequence of QTHQPPAPNSLIR (SEQ ID NO: 36) generated by SRM-MS to a standard curve.

13. The assay of claim 10, wherein the biological sample is a blood sample.

14. The assay of claim 10, wherein the biological sample is a human sample.

15. The assay of claim 10, wherein the biological sample is a non-human primate sample.

16. The assay of claim 10, wherein the selected reaction monitoring mass spectrometry is LC-SRM-MS/MS.

17. The assay of claim 10, wherein the at least one proteolytic enzyme is trypsin.

18. The assay of claim 12, wherein the standard curve is produced using a method comprising:

(a) preparing at least two C1q concentration standards by mixing known quantities of purified C1q protein and C1q-depleted serum;

(b) adding to the at least two C1q concentration standards at least one labeled, synthetic peptide fragment with an amino acid sequence of QTHQPPAPNSLIR (SEQ ID NO: 36);

(c) contacting the at least two labeled C1q concentration standards with a proteolytic enzyme to produce at least one peptide fragment of C1q having the amino acid sequence of QTHQPPAPNSLIR (SEQ ID NO: 36);

(d) performing selected reaction monitoring mass spectrometry to determine the strength of the signal that corresponds to the at least one peptide fragment of C1q having the amino acid sequence of QTHQPPAPNSLIR (SEQ ID NO: 36) and the strength of the signal that corresponds to the at least one labeled, synthetic peptide fragment having the amino acid sequence of QTHQPPAPNSLIR (SEQ ID NO: 36) in each of the at least two labeled C1q concentration standards; and (e) determining a standard curve using the signals and the known quantities of C1q protein.

* * * * *